US011690876B2

(12) United States Patent
Goldman et al.

(10) Patent No.: US 11,690,876 B2
(45) Date of Patent: Jul. 4, 2023

(54) METHODS OF TREATING NEUROPSYCHIATRIC DISORDERS

(71) Applicant: UNIVERSITY OF ROCHESTER, Rochester, NY (US)

(72) Inventors: Steven A. Goldman, Webster, NY (US); Maiken Nedergaard, Webster, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 563 days.

(21) Appl. No.: 16/612,529

(22) PCT Filed: May 10, 2018

(86) PCT No.: PCT/US2018/031961
§ 371 (c)(1),
(2) Date: Nov. 11, 2019

(87) PCT Pub. No.: WO2018/209022
PCT Pub. Date: Nov. 15, 2018

(65) Prior Publication Data
US 2020/0197445 A1 Jun. 25, 2020

Related U.S. Application Data

(60) Provisional application No. 62/504,340, filed on May 10, 2017.

(51) Int. Cl.
A61K 35/30 (2015.01)
A61P 25/18 (2006.01)
A61K 31/495 (2006.01)
C12N 5/0735 (2010.01)
C12N 5/074 (2010.01)
A61K 9/00 (2006.01)

(52) U.S. Cl.
CPC ............ A61K 35/30 (2013.01); A61K 31/495 (2013.01); A61P 25/18 (2018.01); C12N 5/0606 (2013.01); C12N 5/0696 (2013.01); A61K 9/007 (2013.01); A61K 9/0019 (2013.01); A61K 9/0085 (2013.01)

(58) Field of Classification Search
CPC ....... A61K 35/30; A61K 9/0085; A61P 25/18; C12N 5/0606; C12N 5/0696
See application file for complete search history.

(56) References Cited

U.S. PATENT DOCUMENTS

| 3,753,357 A | 8/1973 | Schwartz |
| 4,199,022 A | 4/1980 | Senkan et al. |
| 4,559,298 A | 12/1985 | Fahy |
| 6,235,527 B1 | 5/2001 | Rao et al. |
| 6,245,564 B1 | 6/2001 | Goldman et al. |
| 6,361,996 B1 | 3/2002 | Rao et al. |
| 6,497,872 B1 | 12/2002 | Weiss et al. |
| 6,692,957 B2 | 2/2004 | Goldman et al. |
| 6,734,015 B1 | 5/2004 | Rao et al. |
| 6,787,353 B1 | 9/2004 | Rao et al. |
| 6,830,927 B2 | 12/2004 | Rao et al. |
| 6,852,532 B2 | 2/2005 | Mayer-Proschel et al. |
| 6,900,054 B2 | 5/2005 | Rao et al. |
| 7,037,720 B2 | 5/2006 | Rao et al. |
| 7,150,989 B2 | 12/2006 | Goldman et al. |
| 7,214,372 B2 | 5/2007 | Rao et al. |
| 7,517,521 B2 | 4/2009 | Mayer-Proschel et al. |
| 7,524,491 B2 | 4/2009 | Goldman et al. |
| 7,595,194 B2 | 9/2009 | Rao et al. |
| 7,795,021 B2 | 9/2010 | Rao et al. |
| 8,168,174 B2 | 5/2012 | Mayer-Proschel et al. |
| 8,206,669 B2 | 6/2012 | Goldman et al. |
| 8,206,699 B2 | 6/2012 | Goldman et al. |
| 8,227,247 B2 | 7/2012 | Zhang et al. |
| 8,263,402 B1 | 9/2012 | Goldman et al. |
| 8,658,424 B2 | 2/2014 | Zhang et al. |
| 8,673,292 B2 | 3/2014 | Rao et al. |

(Continued)

FOREIGN PATENT DOCUMENTS

| EP | 2663638 A1 | 11/2013 |
| EP | 1 480 521 B1 | 2/2015 |
| EP | 2 532 241 B1 | 5/2016 |
| EP | 2379711 B1 | 11/2016 |
| EP | 2499238 B1 | 8/2017 |
| JP | 2004-129561 | 4/2004 |
| JP | 2011-155978 A | 8/2011 |
| WO | WO 94/10292 A1 | 5/1994 |
| WO | WO 98/32879 A1 | 7/1998 |
| WO | WO 99/49014 A1 | 9/1999 |
| WO | WO 01/46384 A2 | 6/2001 |
| WO | WO 01/178753 A2 | 10/2001 |

(Continued)

OTHER PUBLICATIONS

Schizophrenia Working Group of the Psychiatric Genomics Consortium, Nature, vol. 511: 421-427, Jul. 24, 2014. (Year: 2014).*

(Continued)

Primary Examiner — Kimberly Ballard
Assistant Examiner — Stacey N MacFarlane
(74) Attorney, Agent, or Firm — Troutman Pepper Hamilton Sanders LLP (Rochester)

(57) ABSTRACT

The present disclosure is directed to a method of treating a neuropsychiatric disorder. This method involves selecting a subject having the neuropsychiatric disorder and administering to the selected subject a preparation of glial progenitor cells at a dosage effective to treat the neuropsychiatric disorder in the subject. Another aspect of the disclosure is directed to a method of treating a neuropsychiatric disorder that includes selecting a subject having the neuropsychiatric disorder and administering, to the selected subject, a potassium ($K^+$) channel activator at a dosage effective to restore normal brain interstitial glial $K^+$ levels in the selected subject and treat the neuropsychiatric disorder is also disclosed.

8 Claims, 31 Drawing Sheets

(56) References Cited

U.S. PATENT DOCUMENTS

| | | |
|---|---|---|
| 8,709,807 B2 | 4/2014 | Mayer-Proschel et al. |
| 9,371,513 B2 | 6/2016 | Goldman et al. |
| 9,709,553 B2 | 7/2017 | Goldman et al. |
| 9,724,432 B2 | 8/2017 | Goldman |
| 10,190,095 B2 | 1/2019 | Goldman et al. |
| 10,279,051 B2 | 5/2019 | Goldman |
| 10,450,546 B2 | 10/2019 | Goldman et al. |
| 10,626,369 B2 | 4/2020 | Goldman et al. |
| 11,344,582 B2 | 5/2022 | Goldman et al. |
| 2002/0012653 A1 | 1/2002 | Pang et al. |
| 2002/0012903 A1 | 1/2002 | Goldman et al. |
| 2002/0061586 A1 | 5/2002 | Goldman et al. |
| 2003/0049234 A1 | 3/2003 | Goldman et al. |
| 2004/0253719 A1 | 12/2004 | Goldman et al. |
| 2005/0084963 A1 | 4/2005 | Chang-Ling |
| 2005/0169902 A1 | 8/2005 | Borlongan et al. |
| 2006/0292128 A1 | 12/2006 | Allen et al. |
| 2010/0159595 A1 | 6/2010 | Zhang et al. |
| 2011/0059055 A1 | 3/2011 | Goldman et al. |
| 2012/0100113 A1 | 4/2012 | Tesar et al. |
| 2012/0177614 A1 | 7/2012 | Kido |
| 2012/0207744 A1 | 8/2012 | Mendlein et al. |
| 2012/0230963 A1 | 9/2012 | Sandrock et al. |
| 2013/0004467 A1 | 1/2013 | Goldman et al. |
| 2015/0328339 A1 | 11/2015 | Goldman et al. |
| 2015/0352154 A1 | 12/2015 | Goldman et al. |
| 2016/0264937 A1 | 9/2016 | Goldman et al. |
| 2016/0317681 A1 | 11/2016 | Goldman |
| 2017/0159015 A1 | 6/2017 | Goldman et al. |
| 2017/0182098 A1 | 6/2017 | Goldman |
| 2017/0198255 A1 | 7/2017 | Goldman et al. |
| 2017/0209494 A1 | 7/2017 | Goldman et al. |
| 2020/0048604 A1 | 2/2020 | Goldman et al. |
| 2020/0048605 A1 | 2/2020 | Goldman et al. |
| 2020/0197445 A1 | 6/2020 | Goldman et al. |
| 2021/0260002 A1 | 8/2021 | Goldman et al. |
| 2022/0025379 A1 | 1/2022 | Goldman et al. |
| 2022/0062378 A1 | 3/2022 | Goldman et al. |
| 2022/0267737 A1 | 8/2022 | Goldman et al. |
| 2022/0273728 A1 | 9/2022 | Goldman et al. |
| 2022/0290099 A1 | 9/2022 | Goldman et al. |

FOREIGN PATENT DOCUMENTS

| | | |
|---|---|---|
| WO | 01/88104 A2 | 11/2001 |
| WO | 03/018782 A2 | 3/2003 |
| WO | WO 03/070171 A2 | 8/2003 |
| WO | WO 2004/007696 A2 | 1/2004 |
| WO | 2004/063356 A2 | 7/2004 |
| WO | 2006/097441 A1 | 9/2006 |
| WO | 2009/133142 A1 | 11/2009 |
| WO | 2010/010380 A1 | 1/2010 |
| WO | 2011/066168 A1 | 6/2011 |
| WO | WO 2012/095730 A1 | 7/2012 |
| WO | 2012/112340 A2 | 8/2012 |
| WO | 2014/058866 A2 | 4/2014 |
| WO | 2017/152081 A1 | 9/2017 |
| WO | WO 2018/209022 | 11/2018 |

OTHER PUBLICATIONS clinicaltrials.gov: NCT01217008, published 2010. (Year: 2010).*
Yandava et al., "'Global' Cell Replacement is Feasible via Neural Stem Cell Transplantation: Evidence from the Dysmyelinated Shiverer Mouse Brain," Proc. Natl. Acad. Sci. USA 96:7029-7034 (1999).
Warrington et al., "Differential Myelinogenic Capacity of Specific Developmental Stages of the Oligodendrocyte Lineage Upon Transplantation Into Hypomyelinating Hosts," J. Neurosci. Res.34:1-13 (1993).
Gumpel et al., "Transplantation of Human Embryonic Oligodendrocytes into Shiverer Brain," Ann. NY Acad. Sci. 495:71-85 (1987).
Lokker et al., "Functional Importance of Platelet-derived Growth Factor (PDGF) Receptor Extracellular Immunoglobulin-like Domains," J. Biol. Chem. 272(52):33037-44 (1997).
Search result of PDGFRA at the Human Protein Atlas (www.Proteinatlas.org).
Notice of Reasons for Rejections for JP 2015-557053 dated Nov. 12, 2018.
Akiyama et al., "Transplantation of Clonal Neural Precursor Cells Derived from Adult Human Brain Establishes Functional Peripheral Myelin in the Rat Spinal Cord," Exp. Neuro. 167:27-39 (2001).
Alenzi et al., "Stem Cells: Biology and Clinical Potential," African Journal of Biotechnology 10(86): 19929-19940 (2011).
Auvergne et al., "Transcriptional Differences Between Normal and Glioma-Derived Glial Progenitor Cells Identity a Core Set of Dysregulated Genes," Cell Reports 3:2127-2141 (2013).
Benraiss et al., "Sustained Mobilization of Endogenous Neural Progenitors Delays Disease Progression in a Transgenic Model of Huntington's Disease," Cell Stem Cell 12:787-799 (2013).
Blakemore et al., "Extensive Oligodendrocyte Remyelination Following Injection of Cultured Central Nervous System Cells into Demyelinating Lesions in Adult Central Nervous System," Dev. Neurosci. 10:1-11 (1988).
Cao et al., "Stem Cell Repair of Central Nervous System Injury," Journal of Neuroscience Research 68:501-510 (2002).
Database Accession No. PREV200100486585 (2001).
Emerich et al., "Recent Efforts to Overcome the Blood-Brain Barrier for Drug Delivery," Exp. Opin. Ther. Patents 10(3):279-287 (2000).
Espinosa De Los Monteros et al., "Remyelination of the Adult Demyelinated Mouse Brain by Grafted Oligodendrocyte Progenitors and the Effect of B-104 Cografts," Neurochemical Res. 26(6):673-682 (2001).
Franklin, "Why Does Remyelination Fail in Multiple Sclerosis?" Nature Rev. Neurosci. 3(9):705-714 (2002).
Gallo et al., "Oligodendrocyte Progenitor Cell Proliferation and Lineage Progression are Regulated by Glutamate Receptor-Mediated K+ Channel Block," J. Neurosci. 16(8): 2659-2670 (1996).
Gensert et al., "Endogenous Progenitors Remyelinate Demyelinated Axons in the Adult CNS," Neuron 19:197-203 (1997).
Godfraind et al., "In Vivo Analysis of Glial Cells Phenotypes During a Viral Demyelinating Disease in Mice," J. Cell Biol. 109:2405-2416 (1989).
Goldman and Windrem, "Stem Cell-Based Strategies for Treating Pediatric Disorders of Myelin," Human Molecular Genetics 17(10): R76-R83 (2008).
Goldman et al., "How to Make an Oligodendrocyte," Development 142:3983-3995 (2015).
Gout et al., "Remvelination by Transplanted Oligodendrocytes of a Demyelinated Lesion in the Spinal Cord of the Adult Shiverer Mouse." Neurosci. Lett. 87:195-199 (1988).
Gumpel et al., "Myelination and Remyelination in the Central Nervous System by Transplanted Oligodendrocytes Using the Shiverer Model," Dev. Neurosci. 11:132-139 (1989).
Izrael et al., "Human Oligodendrocytes Derived From Embryonic Stem Cells: Effect of Noggin on Phenotypic Differentiation In Vitro and on Myelination In Vivo," Mol Cell Neurosci. 34(3):310-23 (2007).
Jeffery et al., "Behavioural Consequences of Oligodendrocyte Progenitor Cell Transplantation into Experimental Demyelinating Lesions in the Rat Spinal Cord," Eur. J. Neurosci. 11:1508-1514 (1999).
K.A. Nave, "Neurological Mouse Mutants and the Genes of Myelin," J. Neurosci. Res. 38(6):607-12 (1994).
Keirstead et al., "Human Embryonic Stem Cell-Derived Oligodendrocyte Progenitor Cell Transplants Remyelinate and Restore Locomotion After Spinal Cord Injury," J Neurosci. 25(19):4694-705 (2005).
Kennea et al., "Neural Stem Cells," Journal of Pathology 197:536-550 (2002).
Kolf et al., "Biology of Adult Mesenchymal Stem Cells: Regulation of Niche, Self-Renewal and Differentiation," Arthritis Research & Therapy 9(204):204-213 (2007).
Lachapelle et al., "Transplantation of CNS Fragments into the Brain of Shiverer Mutant Mice: Extensive Myelination by Implanted Oligodendrocytes," Dev. Neurosci. 6:325-334 (1983).
Learish et al., "Intraventricular Transplantation of Oligodendrocyte Progenitors into a Fetal Myelin Mutant Results in Widespread Formation of Myelin," Annals of Neurology 46(5):716-722 (1999).

(56) References Cited

OTHER PUBLICATIONS

Mehler et al., "Progenitor Cell Biology: Implications for Neural Regeneration," Archives of Neurology 56(7):780-784 (1999).
Milward et al., "Isolation and Transplantation of Multipotential Populations of Epidermal Growth Factor-Responsive, Neural Progenitor Cells from the Canine Brain," Journal of Neuroscience Research 50:862-871 (1997).
Office Action for U.S. Appl. No. 15/427,986 (dated Apr. 18, 2018).
Rossi et al., "Neural Stem Cell Therapy for Neurological Diseases: Dreams and Reality," Nature Reviews Neuroscience 3:401-409 (2002).
Scolding et al., "Identification of A2B5-Positive Putative Oligodendrocyte Progenitor Cells and A2B5-Positive Astrocytes in Adult Human White Matter," Neurosci. 89(1):1-4 (1999).
Seilhean et al., "Myelination by Transplanted Human and Mouse Central Nervous System Tissue After Long-term Cryopreservation," Acta Neuropathologica 91(1):82-88 (1996).
Talan J., "Human Glial Progenitor Cells Remyelinate in Shiverer Mouse: Plans to Study Cell Grafts in Children with Myelin Disease," Neurology Today 8(14):1 (2008).
Tyszka et al., "Statistical Diffusions Tensor Histology Reveals Regional Dysmyelination Effects in the Shiverer Mouse Mutant," NeuroImage 29(4):1058-65 (2006).
Wang et al., "Isolation of Neuronal Precursors by Sorting Embryonic Forebrain Transfected with GFP Regulated by the Tal Tubulin Promoter," Nature Biotechnology 16:196-201 (1998).
Yang et al., "A Novel Approach for Amplification and Purification of Mouse Oligodendrocyte Progenitor Cells," Frontiers in Cellular Neuroscience 10:article 203, p. 1-10 (2016).
Notice of Reasons for Rejections for JP 2015-557053 dated Dec. 4, 2017.
Alsanie et al., "Human Embryonic Stem Cell-Derived Oligodendrocytes: Protocols and Perspectives," Stem Cells and Developments 22(18):2459-2476 (2013).
Hatch et al., "Derivation of High-Purity Oligodendroglial Progenitors," Methods in Molecular Biology 549:59-74 (2009).
Totonchi et al., 2010, Int. J. Dev. Biol., vol. 54, p. 877-886.
International Preliminary Report on Patentability for International Application No. PCT/US14/15019 (dated Aug. 11, 2015).
Sim et al., "Fate Determination of Adult Human Glial Progenitor Cells," Neuron Glia Biol. 5(3/4): 45-55 (2009).
UniProt, UniProtKB-P16234 (PDGFRA_Human), available at http://www.uniprot.org/uniprot/P16234, accessed Jan. 20, 2016.
Office Action for Canadian Patent Application No. 2,723,382, 6 pages (dated May 27, 2015).
International Preliminary Report on Patentability for International Application No. PCT/US2009/043140 (dated Nov. 9, 2016).
Summons to Attend Oral Proceedings for corresponding European Patent Application No. 09743660.4, 5 pages (Sep. 28, 2015).
European Search Report for European Patent Application No. 09743660.4 (dated Dec. 12, 2011).
Communication for European Patent Application No. 09743660.4 (dated Mar. 21, 2014).
Chung et al., "Human Embryonic Stem Cell Lines Generated without Embryo Destruction," Cell Stem Cell 2(2):113-117 (2008).
Li et al., "Oligodendrocyte Progenitor Cells in the Adult Rat CNS Express Myelin Oligodendrocyte Glycoprotein (MOG)," Brain Pathol. 12(4):463-471 (2002).
Crang et al., "The Demonstration by Transplantation of the Very Restricted Remyelinating Potential of Post-Mitotic Oligodendrocytes," J. Neurocytol. 27(7):541-553 (1998).
http://www.pierce-antibodies.com/PDGF-RA--CD140a-antibody-Polyclonal--PA532545.html.
Scolding et al., "Oligodendrocyte Progenitors are Present in the Normal Adult Human CNS and in the Lesions of Multiple Sclerosis," Brain 121:2221-8 (1998).
PE anti-human CD140a (PDGFRalpha) antibody http://www/biolegend.com/pe-anti-human-cd140a-pdgfralpha-antibody-3727.html.

Berry et al., "Cytology and Lineage of NG2-Positive Glia," Journal of Neurocytology 31:457-467 (2002).
Terada et al., "The Tetraspanin Protein, CD9, Is Expressed by Progenitor Cells Committed to Oligodendrogenesis and Is Linked to β1 Integrin, CD81, and Tspan-2," GLIA 40:350-359 (2002).
Armstrong et al., "Pre-Oligodendrocvtes from Adult Human CNS," J. Neurosci. 12(4):1538-47 (1992).
Dennis et al., "DAVID: Database for Annotation, Visualization, and Integrated Discovery," Genome Biol. 4:R60 (2003).
Gentleman et al., "Bioconductor: Open Software Development for Computational Biology and Bioinformatics," Genome Biol. 5(10):R80-R80.16 (2004).
Hall et al., "Spinal Cord Oligodendrocytes Develop from Ventrally Derived Progenitor Cells that Express PDGF alpha-Receptors," Development 122:4085-94 (1996).
Irizarry et al., "Exploration, Normalization, and Summaries of High Density Oligonucleotide Array Probe Level Data," Biostatistics 4(2):249-64 (2003).
Keyoung et al., "High-Yield Selection and Extraction of Two Promoter-Defined Phenotypes of Neural Stem Cells from the Fetal Human Brain," Nature Biotechnology 19:843-50 (2001).
Kirschenbaum et al., "In vitro Neuronal Production and Differentiation by Precursor Cells Derived from the Adult Human Forebrain," Cerebral Cortex 4(6):576-89 (1994).
LaRochelle et al., "Inhibition of Platelet-Derived Growth Factor Autocrine Growth Stimulation by a Monoclonal Antibody to the Human alpha Platelet-Derived Growth Factor Receptor," Cell Growth Differ. 4(7):547-53 (1993).
Linner et al., "A New Technique for Removal of Amorphous Phase Tissue Water Without Ice Crystal Damage: A Preparative Method for Ultrastructural Analysis and Immunoelectron Microscopy," J. Histochem. Cytochem. 34(9):1123-35 (1986).
Matsui et al., "Independent Expression of Human α or β Platelet-Derived Growth Factor Receptor cDNAs in a Naïve Hematopoietic Cell Leads to Functional Coupling with Mitogenic and Chemotactic Signaling Pathways," Proc. Natl. Acad. Sci. USA 86:8314-18 (1989).
Mazur, "The Role of Intracellular Freezing in the Death of Cells Cooled at Supraoptimal Rates," Cryobiology 14:251-72 (1977).
Munson et al. "Ligand: A Versatile Computerized Approach for Characterization of Ligand-Binding Systems," Anal. Biochem. 107:220-39 (1980).
Nunes et al., "Identification and Isolation of Multipotent Neural Progenitor Cells from the Subcortical White Maher of the Adult Human Brain," Nature Medicine 9(4):439-47 (2003).
Pringle et al., "PDGF Receptors in the Rat CNS: During Late Neurogenesis, PDGF Alpha-Receptor Expression Appears to be Restricted to Glial Cells of the Oligodendrocyte Lineage," Development 115:535-51 (1992).
Rasband et al., "Developmental Clustering of ion Channels at and Near the Node of Ranvier," Dev. Biol., 236(1):5-16 (2001).
Readhead et al., "Expression of a Myelin Basic Protein Gene in Transgenic Shiverer Mice: Correction ofthe Dysmyelinating Phenotype," Cell 48:703-12 (1990).
Roy et al., "Identification, Isolation, and Promoter-Defined Separation of Mitotic Oligodendrocyte Progenitor Cells from the Adult Human Subcortical White Matter," J. Neurosci., 19(22) 9986-95 (1999).
Roy et al., "In vitro Neurogenesis by Progenitor Cells Isolated from the Adult Human Hippocampus," Nature Med. 6:271-7 (2000).
Roy et al.. "Telomerase-Immortalization of Neuronally Restricted Progenitor Cells Derived from the Human Fetal Spinal Cord," Nature Biotechnol., 22:297-305 (2004).
Schafer et al., "Glial Regulation of the Axonal Membrane at Nodes of Ranvier," Curr. Opinion in Neurobiology 16:508-14 (2006).
Sherman et al., "Mechanisms of Axon Ensheathment and Myelin Growth," Nature Rev. Neurosci. 6:683-90 (2005).
Shinkai et al., "RAG-2 Deficient Mice Lack Mature Lymphocytes Owing to Inability to Initiate V(D)J Rearrangement," Cell 68(5): 855-67 (1992).
Sim et al., "Complementary Patterns of Gene Expression by Human Oligodendrocyte Progenitors and their Environment Predict Determinants of Progenitor Maintenance and Differentiation," Ann. Neurol. 59(5):763-79 (2006).

(56) References Cited

OTHER PUBLICATIONS

Smyth, "Linear Models and Empirical Bayes Methods for Assessing Differential Expression in Microarray Experiments," Stat. Appl. Genel. Mol. Bio. 3:Article 3 (2004).
Takahashi et al., "Induction of Pluripotent Stem Cells from Mouse Embryonic and Adult Fibroblast Cultures by Defined Factors," Cell 126(4):663-76 (2006).
Windrem et al., "Progenitor Cells Derived from the Adult Human Subcortical White Matter Disperse and Differentiate as Oligodendrocytes within Demyelinated Lesions of the Rat Brain," J. Neurosci. Res. 69(6):966-75 (2002).
Windrem et al., "Fetal and Adult Human Oligodendrocyte Progenitor Cell Isolates Myelinate the Congenitally Dysmyelinated Brain," Nature Medicine 10(1):93-7 (2004).
Yang et al., "βIV Spectrin is Recruited to Axon Initial Segments and Nodes of Ranvier by Ankyrin G," J. Cell Biol. 176:509-19 (2007).
Yu et al., "Induced Pluripotent Stem Cell Lines Derived from Human Somatic Cells," Science 318(5858):1917-20 (2007).
Office Action in U.S. Appl. No. 12/990,874 (dated Nov. 10, 2016).
Office Action in U.S. Appl. No. 12/990,874 (dated May 4, 2016).
Office Action in U.S. Appl. No. 12/990,874 (dated Oct. 20, 2015).
Office Action in U.S. Appl. No. 12/990,874 (dated May 14, 2014).
Office Action in U.S. Appl. No. 12/990,874 (dated Mar. 15, 2013).
Hu et al., "Neural Differentiation of Human Induced Pluripotent Stem Cells Follows Developmental Principles But With Variable Potency," Proc Natl Acad Sci USA 107(9):4335-40 (2010).
Hu et al., "Differentiation of Human Oligodendrocytes From Pluripotent Stem Cells," Nat Protoc. 4(11):1614-22 (2009).
Hu et al., "Human Oligodendrocytes From Embryonic Stem Cells: Conserved SHH Signaling Networks and Divergent FGF Effects," Development 136(9):1443-52 (2009).
Sullivan et al., "Induced Pluripotent Stem Cells: Epigenetic Memories and Practical Implications," Mol Hum Reprod 16(12):880-5 (2010).
Chin et al., "Induced Pluripotent Stem Cells and Embryonic Stem Cells are Distinguished by Gene Expression Signatures," Cell Stem Cell 5(1):111-23 (2009).
Vaskova et al., ""Epigenetic Memory" Phenomenon in Induced Pluripotent Stem Cells," Acta Naturae. Oct. 2013;5(4):15-21.
Allegrucci et al., 2006, Human Reproduction Update, vol. Advance Access published on Aug. 26, 2006, p. 1-18.
Rao, M., 2004, Developmental Biology, vol. 275, p. 269-286.
Abeyta et al., 2004, Human Molecular Genetics, vol. 13, No. 6, p. 601-608.
Narsinh et al., 2011, Molecular therapy, vol. 9, No. 4, p. 635-638.
Bellin et al., 2012, Nature reviews/Molecular Cell Biology, vol. 13, p. 713-726.
Burridge et al., 2011, PLoS ONE, vol. 6, No. 4, e18293, p. 1-16.
Abbaszadeh et al., "Bone Marrow Stromal Cell Transdifferentiation into Oligodendrocyte-Like Cells Using Triiodothyronine as a Inducer with Expression of Platelet-Derived Growth Factor Alpha as a Maturity Marker," Iranian Biomedical Journal 17(2):62-70 (2013).
Han et al., "Direct Reprogramming of Fibroblasts into Neural Stem Cells by Defined Factors," Cell Stem Cell 10:465-472 (2012).
Chua et al., "Neural Progenitors, Neurons and Oligodendrocytes from Human Umbilical Cord Blood Cells in a Senim-Free, Feeder-Free Cell Culture," Biochemical and Biophysical Research Communications 379:217-221 (2009).
Ben-Hur et al., "Prospects of Cell Therapy for Disorders of Myelin," Ann. N.Y. Acad. Sci. 1142:218-249 (2008).
Windrem et al., "Neonatal Chimerization with Human Glial Progenitor Cells Can Both Remyelinate and Rescue the Otherwise Lethally Hypomyelinated Shiverer Mouse," Cell Stem Cell 2:553-565 (2008).
Supplementary Search Report and Search Opinion for EP 14749594.9 dated Jun. 20, 2016.
Goldman et al., "Glial Progenitor Cell-Based Treatment and Modeling of Neurological Disease," Science 338:491-495 (2012).
Sim et al., "CD140a Identifies a Population of Highly Myelinogenic, Migration-Competent and Efficiently Engrafting Human Oligodendrocyte Progenitor Cells," Nature Biotechnology 29(10):934-942 (2011).
Pouya et al., "Human Induced Pluripotent Stem Cells Differentiation into Oligodendrocyte Progenitors and Transplantation in a Rat Model of Optic Chiasm Demyelination," PLos ONE 6(11):e27925 (2011).
Wang et al., "Human iPSC-Derived Oligodendrocyte Progenitor Cells Can Myelinate and Rescue a Mouse Model of Congenital Hypomyelination," Cell Stem Cell 12:252-264 (2013).
International Search Report and Written Opinion for corresponding application No. PCT/US14/15019 dated May 7, 2014.
European Examination Report for EP Patent Application 14749594.9 (dated Oct. 11, 2019).
European Examination Report for EP Patent Application 14749594.9 (dated Dec. 3, 2020).
Extended European Search Report for European Patent Application No. 12176576.2 (dated Nov. 14, 2012).
Supplementary Partial Search Report for European Patent Application No. 03742750.7 (dated Jan. 26, 2006).
Supplementary European Search Report for European Patent Application No. 03742750.7 (dated Nov. 14, 2006).
Examination Report for European Patent Application No. 03742750.7 (dated Jul. 7, 2010).
Examination Report for European Patent Application No. 03742750.7 (dated Oct. 13, 2011).
Examination Report for European Patent Application No. 03742750.7 (dated Nov. 16, 2012).
Examination Report for European Patent Application No. 03742750.7 (dated Aug. 26, 2013).
Notice of Reasons for Rejection for Japanese Patent Application No. 2019-108327 (dated May 18, 2020) with English Translation.
First Office Action for corresponding China Patent Application No. 201880045819.6 (dated May 24, 2021).
International Search Report for International Application No. PCT/US03/04501 (dated Sep. 12, 2003).
Office Action in U.S. Appl. No. 14/764,507 (dated Dec. 22, 2016).
Office Action in U.S. Appl. No. 14/764,507 (dated Aug. 2, 2017).
Office Action in U.S. Appl. No. 14/764,507 (dated Jul. 10, 2018).
Office Action in U.S. Appl. No. 15/427,986 (dated Oct. 9, 2018).
Office Action in U.S. Appl. No. 12/111,839 (dated Dec. 29, 2009).
Office Action in U.S. Appl. No. 12/111,839 (dated Oct. 28, 2010).
Office Action in U.S. Appl. No. 12/111,839 (dated Jul. 27, 2011).
Office Action in U.S. Appl. No. 15/432,341 (dated May 29, 2018).
Restriction Requirement in U.S. Appl. No. 15/432,341 (dated Feb. 23, 2018).
Office Action in U.S. Appl. No. 15/161,917 (dated Sep. 27, 2017).
Restriction Requirement in U.S. Appl. No. 15/161,917 (dated Jun. 20, 2017).
Restriction Requirement in U.S. Appl. No. 13/527,099 (dated Apr. 24, 2013).
Office Action in U.S. Appl. No. 13/527,099 (dated Oct. 9, 2013).
Office Action in U.S. Appl. No. 13/527,099 (dated Sept. 3, 2014).
Office Action in U.S. Appl. No. 13/527,099 (dated Oct. 29, 2015).
Official Action in Canadian Patent Application No. 2476376 (dated Sep. 24, 2009).
Official Action in Canadian Patent Application No. 2476376 (dated Feb. 3, 2011).
Official Action in Canadian Patent Application No. 2476376 (dated May 30, 2012).
Official Action in Canadian Patent Application No. 2476376 (dated May 22, 2013).
Extended European Search Report for European Patent Application 18798072.7 (dated Mar. 3, 2021).
Lyketsos et al., "Neuropsychiatric Symptoms in Alzheimer's Disease," Alzheimer's & Dementia: The Journal of the Alzheimer's Association 7(5):532-539 (2011).
Mendez et al., "Neuropsychiatric Features of Frontotemporal Dementia : Evaluation of Consensus Criteria and Review," Journal of Neuropsychiatry and Clinical Neuroscience 14(4):424-429 (2002).

(56) References Cited

OTHER PUBLICATIONS

Paulsen et al., "Neuropsychiatric Aspects of Huntington's Disease," Journal of Neurology Neurosurgery & Psychiatry 71(3):310-314 (2001).
Kolarik et al., "Transplantation of Human Embryonic Nerve Tissue into a Schizophrenic's Brain," Zentralbl Neurochir 49(3):147-150 (1988).
Windrem et al., "Human iPSC Glial Mouse Chimeras Reveal Glial Contributions to Schizophrenia," Cell Stem Cell 21(2):195-208 (2017).
Benraiss et al., "Human Glia can both Induce and Rescue Aspects of Disease Phenotype in Huntington Disease," Nature Communications 7(1) (2016).
Wang et al., "Human iPSC-Derived Oligodendrocyte Progenitor Cells Can Myelinate and Rescue a Mouse Model of Congenital Hypomyelination." Cell Stem Cell 12(2):252-264 (2013).
Cassoli et al., "Disturbed Macro-Connectivity in Schizophrenia linked to Oligodendrocyte Dysfunction: from Structural Findings to Molecules," NPJ Schizophrenia 1(1):1-10 (2015).
Donegan et al., "Stem Cell-Derived Interneuron Transplants as a Treatment for Schizophrenia: Preclinical Validation in a Rodent Model," Molecular Psychiatry 22(10):1492-1501 (2017).
Goudriaan et al., "Specific Glial Functions Contribute to Schizophrenia Susceptibility," Schizophrenia Bulletin 40(4):925-935 (2013).
Jacobs, Benjamin Meir, "A dangerous method? The use of induced pluripotent stem cells as a model for schizophrenia," Schizophrenia Research 168(1):563-568 (2015).
Takahashi et al., "Linking Oligodendrocyte and Myelin Dysfunction to Neurocircuitry Abnormalities in Schizophrenia," Progress in Neurobiology 93(1):13-24 (2010).
International Search Report and Written Opinion of the International Searching Authority for corresponding International Application No. PCT/US2018/031961 (dated Oct. 19, 2018).
Second Office Action for China Application Serial No. 201880045819.6 dated Jan. 6, 2022 (English Translation).
Notice of Reasons for Rejection for corresponding Japan Application Serial No. 2019-561753 dated Mar. 9, 2022 (English Translation).
Tomimoto, H., "Role of Glial Cells in Vascular Dementia," Medical Science Digest 39(5):219-222 (2013) (English translation of Introduction).
Supplementary Partial European Search Report for European Patent Application 18798072.7 (dated Nov. 27, 2020).
Wang et al., "Navigation for Psychological Growth of Undergraduate Students," Suzhou University Press, 1st Edition, pp. 47-48 (Dec. 2017).
Third Office Action in Corresponding China Application No. 201880045819.6 dated Jun. 13, 2022 (with English Translation).
Second Office Action in Corresponding JP Patent Application No. 2019-561753 dated Oct. 11, 2022 (with English Machine Translation).
Franklin and Bullmore, "Do Not Adjust Your Mind: The Fault Is in Your Glia," Cell Stem Cell 21:155-156 (Aug. 3, 2017).
U.S. Appl. No. 17/430,768, filed Aug. 13, 2021, first named inventor Steven A. Goldman, accessible to the USPTO.
Dietrich et al., "Characterization of A2B5+ Glial Precursor Cells From Cryopreserved Human Fetal Brain Progenitor Cells," Glia 40:65-77 (2002).
Zhang et al., "Oligodendrocyte Progenitor Cells Derived From Human Embryonic Stem Cells Express Neurotrophic Factors," Stem Cells and Development 15:943-952 (2006).
Shin et al., "Whole Genome Analysis of Human Neural Stem Cells Derived From Embryonic Stem Cells and Stem and Progenitor Cells Isolated From Fetal Tissue," Stem Cells 25:1298-1306 (2007).
Dib et al., "Cell Therapy for Cardiovascular Disease: A Comparison of Methods of Delivery," J. of Cardiovasc. Trans. Res. 4:177-181 (2011).
Wu et al., "Cell Delivery in Cardiac Regenerative Therapy," Aging Research Reviews 11:32-40 (2012).
Agrahari et al., "How Are We Improving the Delivery to Back of the Eye? Advances and Challenges of Novel Therapeutic Approaches," Expert Opinion on Drug Delivery 14(10):1145-1162 (2017).
Ikonomou et al., "Unproven Stem Cell Treatments for Lung Disease—An Emerging Public Health Problem," Am. J. Respir. Crit. Care Med. 195:13-14 (2017).
Ikehara S., "Grand Challenges in Stem Cell Treatments," Frontiers in Cell and Developmental Biology 1(2):1-2 (2013).
Cooper et al., "Immunobiological Barriers to Xenotransplantation," International Journal of Surgery 23:211-216 (2015).
Liu et al., "The Immunogenicity and Immune Tolerance of Pluripotent Stem Cell Derivatives," Frontiers in Immunology 8(645):1-6 (2017).

* cited by examiner

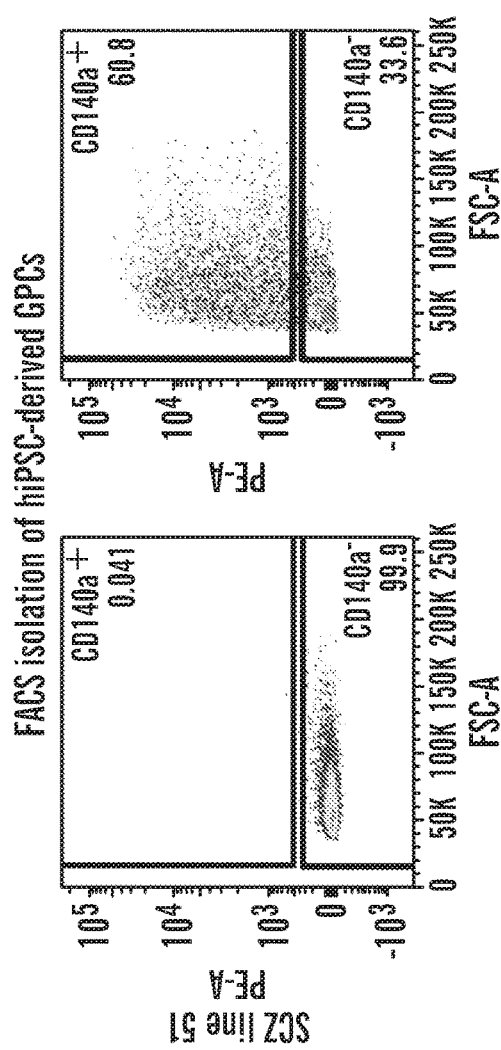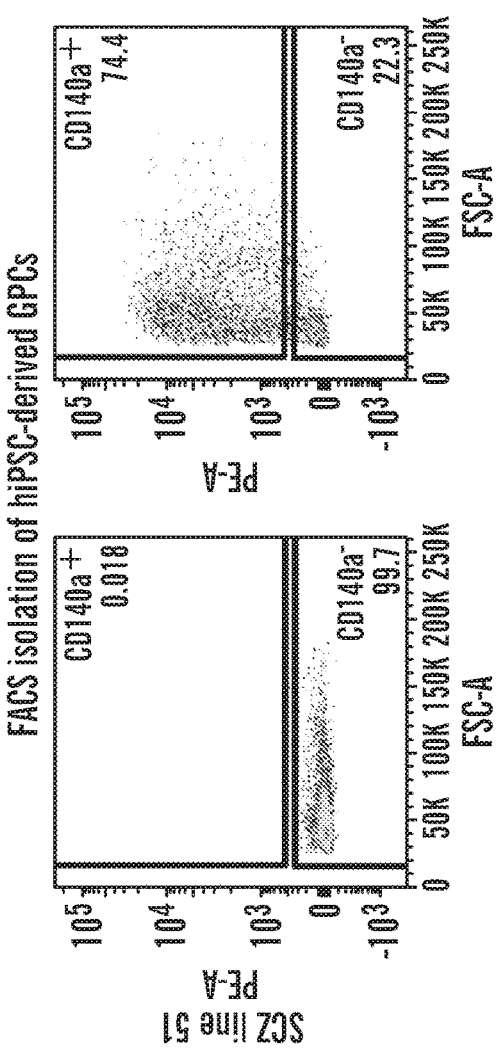
FIG. 2C
FIG. 2D

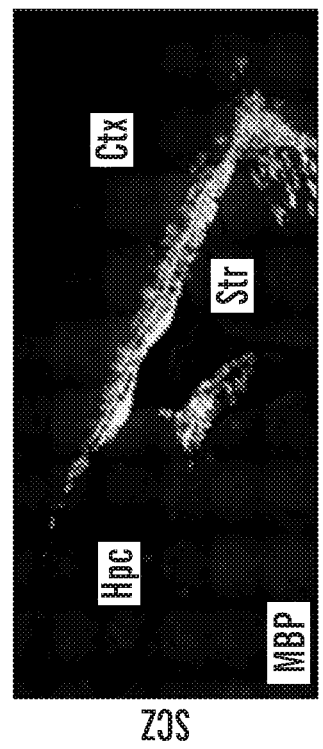
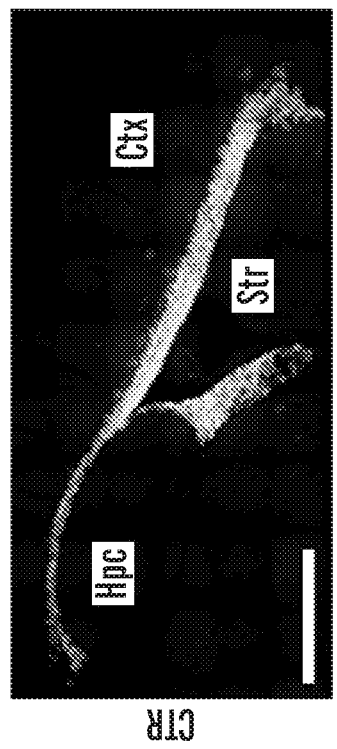
FIG. 3C
FIG. 3D
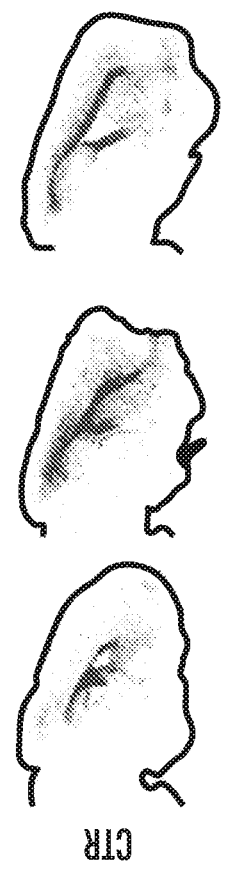
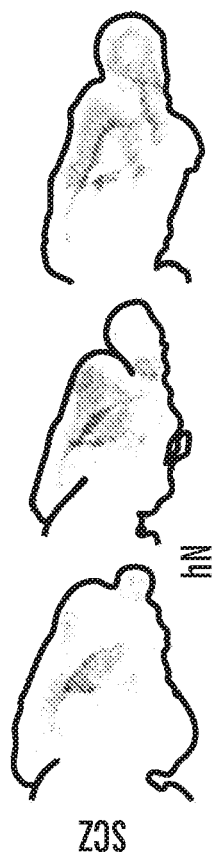
FIG. 3A
FIG. 3B

| # | Annotation Term | P-Value |
|---|---|---|
| 1 | neurotransmitter receptor activity | <1.00E-10 |
|   | extracellular ligand-gated ion channel activity | 1.58E-06 |
|   | ionotropic glutamate receptor activity | 1.72E-06 |
| 2 | anterograde trans-synaptic signaling | <1.00E-10 |
|   | chemical synaptic transmission | <1.00E-10 |
|   | modulation of synaptic transmission | <1.00E-10 |
| 3 | central nervous system development | <1.00E-10 |
|   | oligodendrocyte differentiation | <1.00E-10 |
|   | glial cell differentiation | <1.00E-10 |
| 4 | myelination | 1.68E-06 |
|   | ensheathment of neurons | 1.88E-06 |
|   | galactolipid biosynthesis process | 2.18E-05 |

*FIG. 6C*

METHODS OF TREATING NEUROPSYCHIATRIC DISORDERS

This application is a national stage application under 35 U.S.C. § 371 of PCT Application No. PCT/US2018/031961, filed May 10, 2018, which claims the benefit of U.S. Provisional Patent Application Ser. No. 62/504,340, filed May 10, 2017, which is hereby incorporated by reference in its entirety.

This invention was made with government support under MH099578 and MH104701 awarded by National Institutes of Health. The government has certain rights in the invention.

FIELD

The present application relates to methods of treating neuropsychiatric disorders.

BACKGROUND

There are a number of uniquely human neurological disorders, whose phylogenetic appearance parallels that of human glial evolution, which accelerated with the appearance of hominids (Oberheim et al., "Astrocytic Complexity Distinguishes the Human Brain," *Trends in Neurosciences* 29:1-10 (2006); Oberheim et al., "Uniquely Hominid Features of Adult Human Astrocytes," *The Journal of Neuroscience: The Official Journal of the Society for Neuroscience* 29:3276-3287 (2009); Horrobin, D. F., "Schizophrenia: The Illness That Made Us Human," *Med Hypotheses* 50:269-288 (1998)). In particular, astroglial complexity and pleomorphism increased significantly with hominid evolution, which suggests an association between human glial evolution and the development of human-selective neurological disorders. Indeed, a number of both genome-wide association and differential expression studies have highlighted the frequent dysregulation of glial-selective genes, both astrocytic and oligodendrocytic, in, for example, schizophrenia (Walsh et al., "Rare Structural Variants Disrupt Multiple Genes in Neurodevelopmental Pathways in Schizophrenia," *Science* 320:539-543 (2008); Aberg et al., "Human QKI, A Potential Regulator of mRNA Expression of Human Oligodendrocyte-Related Genes Involved in Schizophrenia," *Proceedings of the National Academy of Sciences of the United States of America* 103:7482-7487 (2006); Roy et al., "Loss of erbB Signaling in Oligodendrocytes Alters Myelin and Dopaminergic Function, A Potential Mechanism for Neuropsychiatric Disorders," *Proceedings of the National Academy of Sciences of the United States of America* 104:8131-8136 (2007); Takahashi et al., "Linking Oligodendrocyte and Myelin Dysfunction to Neurocircuitry Abnormalities in Schizophrenia," *Prog Neurobiol* 93:13-24 (2011); Georgieva et al., "Convergent Evidence That Oligodendrocyte Lineage Transcription Factor 2 (OLIG2) and Interacting Genes Influence Susceptibility to Schizophrenia," *Proceedings of the National Academy of Sciences of the United States of America* 103:12469-12474 (2006); Hof et al., "Molecular and Cellular Evidence for an Oligodendrocyte Abnormality in Schizophrenia," *Neurochem Res* 27:1193-1200 (2002); Hakak et al., "Genome-Wide Expression Analysis Reveals Dysregulation of Myelination-Related Genes in Chronic Schizophrenia," *Proceedings of the National Academy of Sciences of the United States of America* 98:4746-4751 (2001)).

Patients with schizophrenia are typically characterized by a relative paucity of white matter and often frank hypomyelination (Takahashi et al., "Linking Oligodendrocyte and Myelin Dysfunction to Neurocircuitry Abnormalities in Schizophrenia," *Prog Neurobiol* 93:13-24 (2011); Connor et al., "White Matter Neuron Alterations in Schizophrenia and Related Disorders," *International Journal of Developmental Neuroscience: The Official Journal of the International Society for Developmental Neuroscience* 29:325-334 (2011); McIntosh et al., "White Matter Tractography in Bipolar Disorder and Schizophrenia," *Biological Psychiatry* 64:1088-1092 (2008); Maniega et al., "A Diffusion Tensor MRI Study of White Matter Integrity in Subjects at High Genetic Risk of Schizophrenia," *Schizophrenia Research* 106:132-139 (2008); Fields, R. D., White Matter in Learning, Cognition and Psychiatric Disorders," *Trends in Neurosciences* 31:361-370 (2008); Gogtay et al., "Three-Dimensional Brain Growth Abnormalities in Childhood-Onset Schizophrenia Visualized by Using Tensor-Based Morphometry," *Proceedings of the National Academy of Sciences of the United States of America* 105:15979-15984 (2008)). A number of both pathological and neuroimaging studies have highlighted deficiencies in both oligodendroglial density and myelin structure in affected patients (Fields, R. D., White Matter in Learning, Cognition and Psychiatric Disorders," *Trends in Neurosciences* 31:361-370 (2008); Xia et al., "Behavioral Sequelae of Astrocyte Dysfunction: Focus on Animal Models of Schizophrenia," *Schizophrenia Research* (2014); Rapoport et al., "The Neurodevelopmental Model of Schizophrenia: Update 2005," *Molecular Psychiatry* 10:434-449 (2005); Langmead et al., "Fast Gapped-Read Alignment with Bowtie 2," *Nature Methods* 9:357-359 (2012)), including at the ultrastructural level (Uranova et al., "Ultrastructural Alterations of Myelinated Fibers and Oligodendrocytes in the Prefrontal Cortex in Schizophrenia: A Postmortem Morphometric Study," *Schizophrenia Research and Treatment* 2011:325789 (2011); Uranova et al., "The Role of Oligodendrocyte Pathology in Schizophrenia," *Int J Neuropsychopharmacol* 10:537-545 (2007); Pruitt et al., "NCBI Reference Sequences (RefSeq): A Curated Non-Redundant Sequence Database of Genomes, Transcripts and Proteins," *Nucleic Acids Research* 35:D61-65 (2007)). Furthermore, recent studies have emphasized the role of oligodendrocytes in the metabolic support of neurons, suggesting myelin-independent mechanisms whereby oligodendrocytic dysfunction might yield neuronal pathology (Lee et al., "Oligodendroglia Metabolically Support Axons and Contribute to Neurodegeneration," *Nature* 487:443-448 (2012); Simons et al., "Oligodendrocytes: Myelination and Axonal Support," *Cold Spring Harb Perspect Biol.* (2015)). Yet despite genetic, cellular, pathological, and radiological studies that have correlated glial and myelin pathology with schizophrenia, the prevailing view is that that clinical hypomyelination among schizophrenics is secondary to neuronal pathology. Thus, the contribution of cell-autonomous glial dysfunction to schizophrenia has not been well studied, and consequently therapies targeting such dysfunctions have yet to be proposed.

The present disclosure is directed to overcoming these and other deficiencies in the art.

SUMMARY

One aspect of the present disclosure relates to a method of treating a neuropsychiatric disorder. This method involves selecting a subject having the neuropsychiatric disorder and administering to the selected subject a preparation of glial progenitor cells at a dosage effective to treat the neuropsychiatric disorder in the subject.

Another aspect of the present disclosure relates to a method of treating a neuropsychiatric disorder. This method includes selecting a subject having the neuropsychiatric disorder and administering, to the selected subject, a K$^+$ channel activator at a dosage effective to restore normal brain interstitial glial K$^+$ levels in the selected subject and treat the neuropsychiatric disorder.

Another aspect of the present disclosure relates to a non-human animal model of a neuropsychiatric disorder. This non-human mammal has at least 30% of all of its glial cells in its corpus callosum being human glial cells derived from a human patient with a neuropsychiatric disorder and/or at least 5% of all of its glial cells in the white matter of its brain and/or brain stem being human glial cells derived from a human patient with a neuropsychiatric disorder.

Applicants have established that the contribution of cell autonomous glial dysfunction neurological disease can be investigated using a novel model of human glial chimeric mice (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008); Han et al., "Forebrain Engraftment by Human Glial Progenitor Cells Enhances Synaptic Plasticity and Learning in Adult Mice," *Cell Stem Cell* 12:342-353 (2013); Goldman et al., "Modeling Cognition and Disease Using Human Glial Chimeric Mice," *Glia* 63:1483-1493 (2015), which are hereby incorporated by reference in their entirety) paired with the development of protocols for generating bipotential astrocyte-oligodendrocyte glial progenitor cells (GPCs) from patient-specific human induced pluripotent stem cells (hiPSCs) (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety). In these human glial chimeric mouse brains, the majority of resident glia are replaced by human glia and their progenitors (Windrem et al., "A Competitive Advantage by Neonatally Engrafted Human Glial Progenitors Yields Mice Whose Brains are Chimeric for Human Glia," *The Journal of Neuroscience: The Official Journal of the Society for Neuroscience* 34:16153-16161 (2014), which is hereby incorporated by reference in its entirety), allowing human glial physiology, gene expression, and effects on neurophysiological function to be assessed in vivo, in live adult mice (Han et al., "Forebrain Engraftment by Human Glial Progenitor Cells Enhances Synaptic Plasticity and Learning in Adult Mice," *Cell Stem Cell* 12:342-353 (2013), which is hereby incorporated by reference in its entirety). As described herein, the glial chimeric model was used to assess the contribution of human glia to schizophrenic disease phenotype. To this end, hGPCs were prepared from iPSCs derived from fibroblasts taken from either juvenile-onset schizophrenic (SCZ) patients or their normal controls. Differential gene expression of SCZ hGPCs was assessed relative to those of normal subjects, and the cells were transplanted into immunodeficient neonatal mice to produce patient-specific human glial chimeric mice. The glial chimeric mice were then analyzed in regard to the effects of SCZ derivation on astrocytic and oligodendrocytic differentiations in vivo, as well as on behavioral phenotype, and the data thereby obtained correlated to disease-associated gene expression. Using this model of human specific neuropsychiatric disease, applicants have identified novel therapeutic approaches for the treatment of human neuropsychiatric disorders and conditions that are described herein.

BRIEF DESCRIPTION OF THE DRAWINGS

FIGS. 2A-2H show CD140a+ glial progenitor cells are efficiently produced from both SCZ and normal hiPSCs. Flow cytometry for CD140a/PDGFαR+ glial progenitor cells (right plots, compared to unstained gating controls on left), reveals dominant proportions of CD140a-defined cells in both normal control patient-derived (top, FIGS. 2A-2B) and SCZ-derived (bottom, FIGS. 2C-2D) preparations. FIGS. 2A-2C and 2B-2D were run as matched pairs; FIGS. 2A and 2C show 177 and 168 days in vitro (DIV); FIGS. 2B and 2D show 188 and 196 DIV. FIGS. 2E-2H show a representative post-FACS preparation of CD140a-sorted cells. FIG. 2E is a phase image of cells immunostained for both olig2 (FIG. 2F, red) and PDGFRα (FIGS. 2G; 2H, merged). These plots were typical of GPC cultures of both normal and SCZ-derived hiPSC lines. The sorted populations were used for genomics assessment, while both sorted and unsorted cells were used for transplantation, with no evident performance differences between the two.

FIGS. 3A-3J show schizophrenia-derived hGPCs exhibit aberrant dispersal and relative hypomyelination. Human iPSC GPC chimeras were established by neonatal hGPC injection into shiverer mice. Chimeric mice were sacrificed at 19 weeks. GPCs derived from a control subject (FIG. 3A) dispersed primarily in the major white matter tracts, whereas SCZ-derived GPCs (15 year old male) (FIG. 3B) showed less white matter residence and more rapid cortical infiltration. FIGS. 3C-3D are sagittal sections that reveal callosal myelination by SCZ GPCs (FIG. 3D) was less dense than that by control hGPCs (FIG. 3C). FIGS. 3E-3F show higher power images from chimeric mice engrafted with hGPCs from 4 control patients (FIG. 3E) vs. chimeric mice engrafted with hGPCs from 4 different SCZ patients (FIG. 3F). FIG. 3G shows MBP luminance confirmed the greater callosal myelination of CTRL GPC-engrafted vs. SCZ GPC-engrafted mice at 19 weeks (means of 4 different SCZ and CTRL patients each, n>3 mice/patient) (p=0.0002, t-test). FIG. 3H shows that absolute donor cell densities were lower in SCZ than control hGPC-engrafted corpus callosum (p<0.0001, t-test), as were the densities of olig2$^+$ hGPCs and oligodendroglia (FIG. 3I) (p=0.0064, t-test) and transferrin (TFN)$^+$ oligodendroglia (FIG. 3J) (p<0.0001, t-test).

FIGS. 4A-4B show 4 mice each implanted with either control subject-derived (line 22) or SCZ patient-derived (line 51) hGPCs. All SCZ hGPC-engrafted mice show disproportionate hGPC entry into the cortical and striatal gray matter, with less expansion and hence less net engraftment in the forebrain white matter tracts. This difference in hGPC dispersal pattern was noted consistently in all 4 SCZ lines assessed in vivo, each derived from a different patient, relative to their matched 4 control lines, similarly obtained from distinct patients (see FIG. 3).

FIGS. 5A-5B are representative images of the corpus callosum of mice neonatally injected with iPSC GPCs derived from either control (FIG. 5A, line 22) or schizophrenic (FIG. 5B, line 164) subjects (human nuclear antigen, green; glial fibrillary acidic protein, red). FIG. 5A shows control hiPSC GPCs from all tested patients rapidly differentiated as GFAP+ astrocytes with dense fiber arrays in both callosal white and cortical gray matter. FIG. 5B, in contrast, shows SCZ GPCs were slow to mature, with delayed GFAP expression. At 19 weeks, GFAP+ astrocyte densities were significantly greater in mice chimerized with control than SCZ-derived GPCs, both as a group (FIG. 5C), and when analyzed line-by-line (FIG. 5D). This was not just a function of less callosal engraftment, as the proportion of human donor cells that developed GFAP and astrocytic phenotype was significantly lower in SCZ– than control GPC-engrafted mice (FIG. 5E). Sholl analysis of individual astroglial morphologies (Sholl, D. A., "Dendritic Organization in the Neurons of the Visual and Motor Cortices of the Cat," *J. Anat.* 87:387-406 (1953), which is hereby incorporated by reference in its entirety), as imaged in 150 μm sections and reconstructed in 3D by Neurolucida (FIG. 5J), revealed that astrocytes in SCZ hGPC chimeras differed significantly from their control hGPC-derived counterparts, with fewer primary processes (FIG. 5F), less proximal branching (FIG. 5G), and longer distal fibers (FIG. 5H). When the 3-D tracings (FIG. 5J) were assessed by Fan-in radial analysis (MBF Biosciences) (Dang et al., "Formoterol, a Long-acting Beta2 Adrenergic Agonist, Improves Cognitive Function and Promotes Dendritic Complexity in a Mouse Model of Down Syndrome," *Biol. Psychiatry* 75:179-188 (2014), which is hereby incorporated by reference in its entirety), control astrocytic processes were noted to extend uniformly in all directions, but SCZ astrocyte processes left empty spaces, indicative of a discontiguous domain structure (FIG. 5I). *$p<0.0001$, by t-test (FIGS. 5C, 5E, 5F, 5H; by 2-way ANOVA in FIG. 5D; $p<0.002$ in FIG. 5I; $p<0.0001$ by non-linear comparison in FIG. 5G. Scale, FIGS. 5A-5B=50 μm, FIG. 5J=25 μm.

FIGS. 6A-6G show schizophrenia-derived hGPCs suppress glial differentiation-associated gene expression. RNA sequence analysis reveals differential gene expression by SCZ hGPCs. FIG. 6A shows an intersection of lists of differentially expressed genes (DEGs) (log 2-fold change >1.00, FDR 5%) obtained by comparison of hGPCs derived from 4 different schizophrenia patients, compared to pooled control hGPCs. FIG. 6B is a network representation of functional annotations for the intersection gene list shown in FIG. 6A. In the upper network, green and red nodes represent down- and up-regulated genes, respectively, and white nodes represent significantly associated annotation terms (FDR-corrected $p<0.01$; annotation terms include GO:BP, GO:MF, pathways, and gene families, and nodes are sized by degree). Lower network highlights 4 highly interconnected modules identified by community detection. FIG. 6C shows top annotation terms identified for each module in FIG. 6B. FIG. 6D is a heatmap representation of 12 conserved differentially expressed genes that are associated to module 1 (grey in FIG. 6B, 32.4%), which includes annotations related to neurotransmitter receptor and gated channel activity. FIG. 6E is a heatmap representation of 15 conserved differentially expressed genes that are associated to module 2 (orange in FIG. 6B, 28.7%), which comprises annotations related to cell-to-cell signaling and synaptic transmission. FIG. 6F is a heatmap representation of 21 conserved differentially expressed genes that are associated to module 3 (dark blue in FIG. 6B, 28.7%); annotations related to CNS and glial differentiation and development. FIG. 6G is a heatmap representation of 4 conserved differentially expressed genes that are associated to module 4 (light blue in FIG. 6B, 10.2%), with annotations related to myelination and lipid biosynthesis. The absolute expression in heatmaps is shown in UQ-normalized, log 2-transformed counts (Li et al., "Comparing the Normalization Methods for the Differential Analysis of Illumina High-Throughput RNA-Seq Data," *BMC Bioinformatics* 16:347 (2015), which is hereby incorporated by reference in its entirety).

(FIG. 7A) transcription regulators, zinc finger proteins, and other nucleus-associated proteins; (FIG. 7R) unannotated genes, open reading frames, and long intergenic non-coding RNAs.

FIGS. 10A-10E show behavioral tests that were performed in mice chimerized with one of 3 SCZ or 3 control hGPC lines, each line from a different patient. 7-20 recipient mice were tested per cell line, males and females equally. FIG. 10A shows prepulse inhibition studies. Normally-myelinated rag1−/− mice engrafted with SCZ hGPCs had reduced auditory pre-pulse inhibition (PPI) at all volumes of pre-pulse (FIG. 10A). The extent of PPI differed significantly between control (n=13) and SCZ (n=27) hGPC-engrafted animals (p=0.0008 by ANOVA, F=11.76 [1,114]). FIG. 10B shows elevated plus maze studies. The left panel shows representative heat maps of the cumulated movement of a mouse engrafted with SCZ hGPCs, relative to its matched normal hGPC-engrafted control, in the elevated plus maze, a test designed to assess anxiety, in which preference for enclosed space and avoidance of open height suggests greater anxiety. The right panel shows mice engrafted with hGPCs from 3 SCZ patients (12 implanted mice each, for n=36 mice total) spent more time in the closed maze arms than did control-engrafted mice (n=36, also derived from 3 patients) (p=0.036, 2-tailed t test). FIG. 10C shows sucrose preference studies. SCZ GPC-engrafted mice were less likely to prefer sweetened water, suggesting relative anhedonia (p=0.02, Mann-Whitney t-test; n=30 mice derived from 3 SCZ lines; n=17 mice from 3 control lines). FIG. 10D shows 3-chamber socialization test studies. Mice engrafted with hGPCs were placed into the middle chamber of a box divided into 3 compartments, one holding an empty cage (bottom, "X" in FIG. 10D) and one containing an unfamiliar mouse (top, filled white circle), then video-tracked for 10 minutes. Mice engrafted with SCZ hGPCs (right heat-map) avoided strangers more than controls (left heat-map) (p=0.02; 3 SCZ lines, 34 mice; 3 control lines, 36 mice). FIG. 10E shows novel object recognition studies. Mice engrafted with SCZ hGPCs showed significantly poorer novel object recognition (p=0.0006; 3 SCZ lines, 19 mice; 3 control lines, 28 mice). FIGS. 10F-10G demonstrate the diurnal activity and sleep patterns of adult mice (70-80 weeks old) engrafted neonatally with either SCZ or CTRL hGPCs were assessed for 72 hrs in closed chambers (Noldus Ethovision), under continuous video recording. FIG. 10F shows the average distance traveled in meters/hr over a 72 hr period calculated and compared between CTRL mice (gray fill, n=8 mice; lines 22 and 17) and SCZ mice (purple fill; n=10, line 52). Time of day is shown as a 24-hour cycle, with the dark phase indicated by gray background shading. The SCZ mice were significantly more active throughout the observation period than CTRL-engrafted mice (p<0.0001, ANOVA, F=19.32 [1,851]. FIG. 10G shows, on the left, sample heat-maps of one hour of activity during the light phase (16:00 hrs, 2nd day in box), the normal period of sleep for mice. The control mouse (left) remains inactive for the entire hour, while the SCZ mouse moves about the cage during much of the hour. As shown on the right, the SCZ mice exhibited sleep patterns that were fragmented into bouts of shorter duration than their normal hGPC-chimeric controls (p=0.0026 by ANOVA, F=12.08 [1,24]. Means±SEM; unpaired, two-tailed Welch-corrected t-tests.

DETAILED DESCRIPTION

Figure 1:
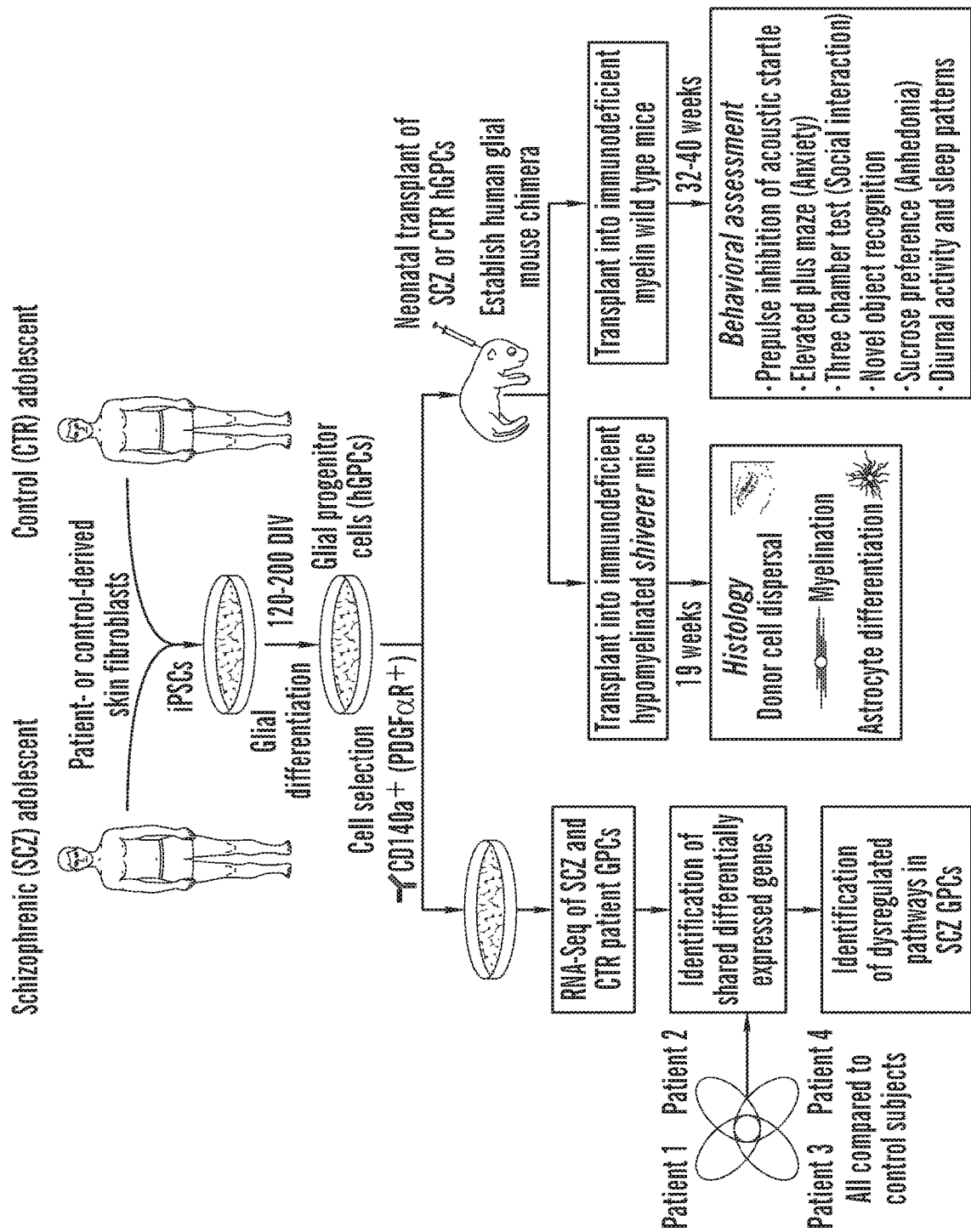
FIG. 1 shows the functional and genomic assessment of schizophrenia-derived glial progenitor cells. This schematic summarizes the steps involved in the analysis of glial progenitor cells derived from individuals with juvenile-onset schizophrenia, compared to GPCs derived from behaviorally-normal controls. The major output data include effects of SCZ origin on in vivo oligodendrocyte maturation and myelination (FIG. 3); in vivo astrocyte differentiation and phenotype (FIG. 5); in vitro differential gene expression (FIG. 6); and behavioral phenotype of the human glial chimeric host animals (FIG. 10).
Figure 2A:
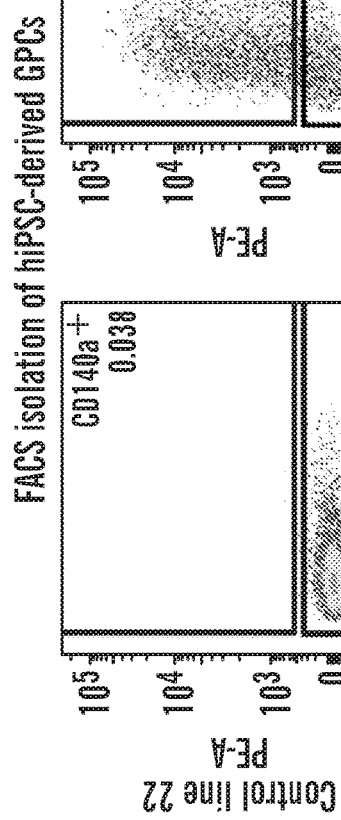
Figure 2B:
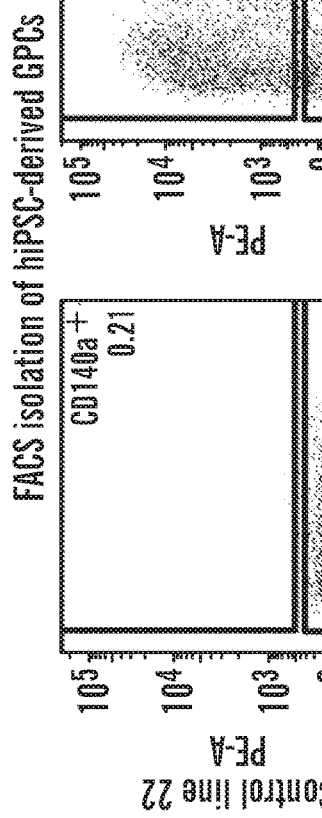
Figure 2E:
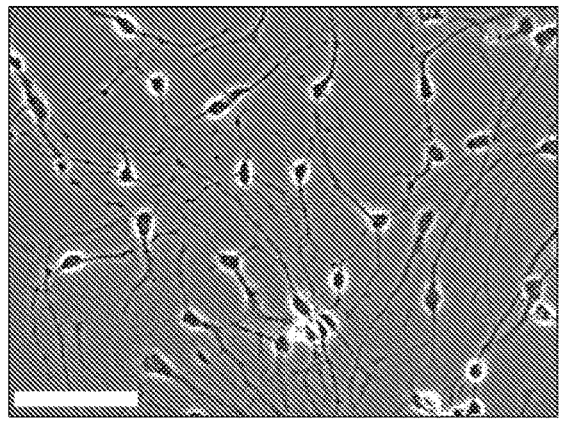
Figure 2F:
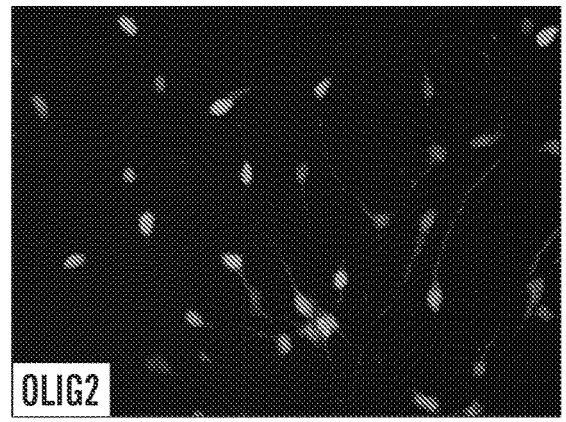
Figure 2G:
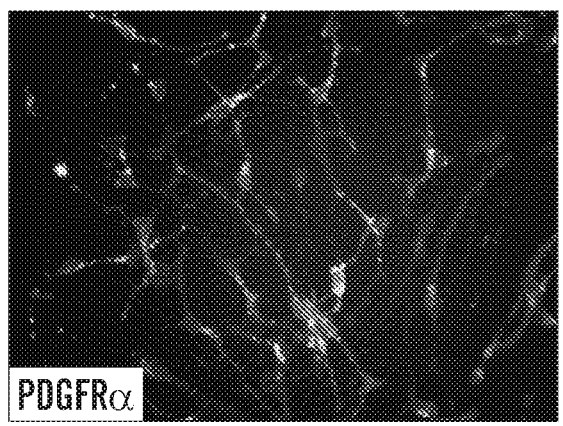
Figure 2H:
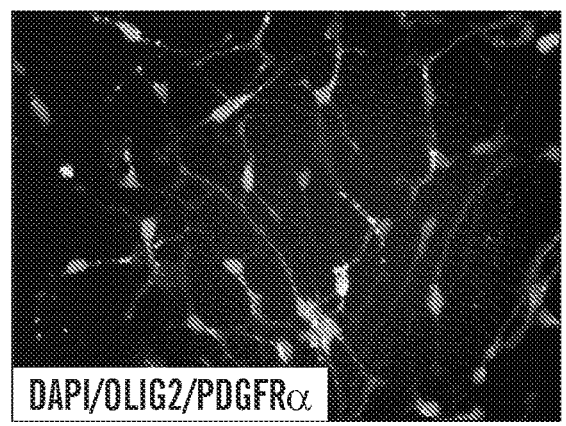

One aspect of the present disclosure relates to a method of treating a neuropsychiatric disorder. This method involves selecting a subject having the neuropsychiatric disorder and administering to the selected subject a preparation of glial progenitor cells at a dosage effective to treat the neuropsychiatric disorder in the subject.

A "neuropsychiatric disorder" as referred to herein, includes any brain disorder with psychiatric symptoms including, but not limited to, dementia, amnesic syndrome, and personality-behavioral changes. Exemplary neuropsychiatric disorders to be treated using the methods described herein include, without limitation, schizophrenia, autism spectrum disorders, and bipolar disorder.

Schizophrenia is a chronic and severe mental disorder that affects how a person thinks, feels, and behaves. To date, there have been several suggested staging models of the disorder (Agius et al., "The Staging Model in Schizophrenia, and its Clinical Implications," *Psychiatr. Danub.* 22(2):211-220 (2010); McGorry et al., "Clinical Staging: a Heuristic Model and Practical Strategy for New Research and Better Health and Social Outcomes for Psychotic and Related Disorders," *Can. J Psychiatry* 55(8):486-497 (2010); Fava and Kellner, "Staging: a Neglected Dimension in Psychiatric Classification," *Acta Psychiatr. Scand.* 87:225-230 (1993), which are hereby incorporated by reference in their entirety). However, generally, schizophrenia develops in at least three stages: the prodromal phase, the first episode, and the chronic phase. There is also heterogeneity of individuals at all stages of the disorder, with some individuals considered ultra-high risk, clinical-high risk, or at-risk for the onset of psychosis (Fusar-Poli et al., "The Psychosis High-Risk State: a Comprehensive State-of-the-Art Review," *JAMA Psychiatry* 70:107-120 (2013), which is hereby incorporated by reference in its entirety).

The methods described herein are suitable for treating a subject in any stage of schizophrenia, and at any risk level of psychosis. For example, in one embodiment, a subject treated in accordance with the methods described herein is a subject that is at risk for developing schizophrenia. Such a subject may have one or more genetic mutations in one or more genes selected from ABCA13, ATK1, C4A, COMT, DGCR2, DGCR8, DRD2, MIR137, NOS1AP, NRXN1, OLIG2, RTN4R, SYN2, TOP3B YWHAE, ZDHHC8, or chromosome 22 (22q11) that have been associated with the development of schizophrenia and may or may not be exhibiting any symptoms of the disease. In another embodiment, the subject may be in the prodromal phase of the disease and exhibiting one or more early symptoms of schizophrenia, such as anxiety, depression, sleep disorders, and/or brief intermittent psychotic syndrome. In another embodiment, the subject being treated in accordance with the methods described herein is experiencing psychotic symptoms, e.g., hallucinations, paranoid delusions, of schizophrenia.

As referred to herein, "Autism Spectrum Disorder" encompasses a group of conditions including Autistic disorder, Asperger's disorder, Pervasive Developmental Disorder—Not Otherwise Specified, Childhood Disintegrative Disorder, and Rett's Disorder, which vary in the severity of symptoms including difficulties in social interaction, communication, and unusual behaviors (McPartland et al., "Autism and Related Disorders," *Handb Clin Neurol* 106: 407-418 (2012), which is hereby incorporated by reference in its entirety). The methods described herein are suitable for the treatment of each one of these conditions included in the autism spectrum.

As referred to herein "bipolar disorder" is a group of conditions characterized by chronic instability of mood, circadian rhythm disturbances, and fluctuations in energy level, emotion, sleep, and views of self and others. "Bipolar disorders" encompasses bipolar disorder type I, bipolar disorder type II, cyclothymic disorder, and bipolar disorder not otherwise specified. Individuals at greatest risk for developing a bipolar disorder are those with a family history of the condition. To date, there have been several suggested staging models of the disorders (McGorry et al., "Clinical Staging: a Heuristic Model and Practical Strategy for New Research and Better Health and Social Outcomes for Psychotic and Related Disorders," *Can. J. Psychiatry* 55(8): 486-497 (2010); McNamara et al., "Preventative Strategies for Early-Onset Bipolar Disorder: Towards a Clinical Staging Model," *CNS Drugs* 24:983-996 (2010); Kapczinski et al., "Clinical Implications of a Staging Model for Bipolar Disorders," *Expert Rev Neurother* 9:957-966 (2009), which are hereby incorporated by reference in their entirety). However, generally, bipolar disorders are progressive conditions which develop in at least three stages: the prodromal phase, the symptomatic phase, and the residual phase.

The methods described herein are suitable for treating subjects having any of the aforementioned bipolar disorders and subjects in any stage of a particular bipolar disorder. The methods described herein are suitable for treating subjects having any of the aforementioned bipolar disorders and subjects in any stage of a particular bipolar disorder. For example, in one embodiment, the subject treated in accordance with the methods described herein is a subject at the early prodromal phase exhibiting symptoms of mood lability/swings, depression, racing thoughts, anger, irritability, physical agitation, and anxiety. In another embodiment, the subject treated in accordance with the methods described herein is a subject at the symptomatic phase or the residual phase.

As used herein, the term "subject" expressly includes human and non-human mammalian subjects. The term "non-human mammal" as used herein extends to, but is not restricted to, household pets and domesticated animals. Non-limiting examples of such animals include primates, cattle, sheep, ferrets, mice, rats, swine, camels, horses, poultry, fish, rabbits, goats, dogs and cats.

In accordance with aspects illustrated herein, the preparation of glial progenitor cells to be administered to the selected subject may be human or non-human. In one embodiment, the preparation of glial progenitor cells is a preparation of human glial progenitor cells.

Preferably the glial progenitor cells are bi-potential glial progenitor cells. In one embodiment, the glial progenitor cells are biased to producing oligodendrocytes. In another embodiment, the glial progenitor cells are biased to producing astrocytes. Methods and markers for producing and distinguishing astrocyte-biased and oligodendrocyte-biased glial progenitor cells are described herein.

Glial progenitor cells suitable for use in the methods described here can be derived from multipotent (e.g., neural stem cells) or pluripotent cells (e.g., embryonic stem cells or induced pluripotent stem cells) using methods known in the art or described herein.

In one embodiment, glial progenitor cells are derived from embryonic stem cells. Embryonic stem cells are derived from totipotent cells of the early mammalian embryo and are capable of unlimited, undifferentiated proliferation in vitro. As used herein, the term "embryonic stem cells" refer to a cells isolated from an embryo, placenta, or umbilical cord, or an immortalized version of such a cells, i.e., an embryonic stem cell line. Suitable embryonic stem cell lines include, without limitation, lines WA-01 (H1), WA-07, WA-09 (H9), WA-13, and WA-14 (H14) (Thomson et al., "Embryonic Stem Cell Lines Derived from Human Blastocytes," *Science* 282 (5391): 1145-47 (1998) and U.S. Pat. No. 7,029,913 to Thomson et al., which are hereby incorporated by reference in their entirety). Other suitable embryonic stem cell lines includes the HAD-C100 cell line (Tannenbaum et al., "Derivation of Xeno-free and GMP-grade Human Embryonic Stem Cells—Platforms for Future Clinical Applications," *PLoS One* 7(6):e35325 (2012), which is hereby incorporated by reference in its entirety, the WIBR4, WIBR5, WIBR6 cell lines (Lengner et al., "Derivation of Pre-x Inactivation Human Embryonic Stem Cell Line in Physiological Oxygen Conditions," *Cell* 141(5):872-83 (2010), which is hereby incorporated by reference in its entirety), and the human embryonic stem cell lines (HUES) lines 1-17 (Cowan et al., "Derivation of Embryonic Stem-Cell Lines from Human Blastocytes," *N. Engl. J. Med.* 350:1353-56 (2004), which is hereby incorporated by reference in its entirety).

In one embodiment, glial progenitor cells are derived from induced pluripotential cells (iPSCs). "Induced pluripotent stem cells" as used herein refers to pluripotent cells that are derived from non-pluripotent cells, such as somatic cells or tissue stem cells. For example, and without limitation, iPSCs can be derived from embryonic, fetal, newborn, and adult tissue, from peripheral blood, umbilical cord blood, and bone marrow (see e.g., Cai et al., "Generation of Human Induced Pluripotent Stem Cells from Umbilical Cord Matrix and Amniotic Membrane Mesenchymal Cells," *J Biol. Chem.* 285(15): 112227-11234 (2110); Giorgetti et al., "Generation of Induced Pluripotent Stem Cells from Human Cord Blood Cells with only Two Factors: Oct4 and Sox2," *Nature Protocols,* 5(4):811-820 (2010); Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/eurheartj/ehs203 (Jul. 12, 2012); Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-07-298331 (Feb. 4, 2011); Sommer et al., "Generation of Human Induced Pluripotent Stem Cells from Peripheral Blood using the STEMCCA Lentiviral Vector," *J. Vis. Exp.* 68: e4327 doi:10.3791/4327 (2012), which are hereby incorporated by reference in their entirety). Exemplary somatic cells that can be used include fibroblasts, such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/eurheartj/ehs203 (2012), which is hereby incorporated by reference in its entirety). Although skin and cheek provide a readily available and easily attainable source of appropriate cells, virtually any cell can be used. Exemplary stem or progenitor cells that are suitable for iPSC production include, without limitation, myeloid progenitors, hematopoietic stem cells, adipose-derived stem cells, neural stem cells, and liver progenitor cells.

Autologous, allogenic, or xenogenic non-pluripotent cells can be used in to produce the iPSCs used to generate the therapeutic glial progenitor cells. Allogenic cells for production of iPSCs, for example, are harvested from healthy donors (i.e., donors not having a neuropsychiatric disorder) and/or donor sources having suitable immunohistocompatibility. Xenogeneic cells can be harvested from a pig, monkey, or any other suitable mammal for the production if iPSCs. Autologous non-pluripotent cells can also be harvested from the same subject to be treated. However, such autologous cells require genetic manipulation and/or other treatment prior to therapeutic administration. In particular, as described herein expression of a number of genes (see Table 2) are dysregulated in neuropsychiatric disorders. Accordingly, autologous cells are preferably genetically modified and/or otherwise treated to correct the dysregulation so that they exhibit normal, non-disease related expression and/or activity levels prior to administration.

Induced pluripotent stem cells can be produced by expressing a combination of reprogramming factors in a somatic cell. Suitable reprogramming factors that promote and induce iPSC generation include one or more of Oct4, Klf4, Sox2, c-Myc, Nanog, C/EBPα, Esrrb, Lin28, and Nr5a2. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell.

iPSCs may be derived by methods known in the art including the use of integrating viral vectors (e.g., lentiviral vectors, inducible lentiviral vectors, and retroviral vectors), excisable vectors (e.g., transposon and floxed lentiviral vectors), and non-integrating vectors (e.g., adenoviral and plasmid vectors) to deliver the aforementioned genes that promote cell reprogramming (see e.g., Takahashi and Yamanaka, *Cell* 126:663-676 (2006); Okita. et al., *Nature* 448:313-317 (2007); Nakagawa et al., *Nat. Biotechnol.* 26:101-106 (2007); Takahashi et al., *Cell* 131:1-12 (2007); Meissner et al. *Nat. Biotech.* 25:1177-1181 (2007); Yu et al. *Science* 318:1917-1920 (2007); Park et al. *Nature* 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/118820, U.S. Patent Application Publication Nos. 2011/0200568 to Ikeda et al., 2010/0156778 to Egusa et al., 2012/0276070 to Musick, and 2012/0276636 to Nakagawa, Shi et al., *Cell Stem Cell* 3(5): 568-574 (2008), Kim et al., *Nature* 454: 646-650 (2008), Kim et al., *Cell* 136(3):411-419 (2009), Huangfu et al., *Nature Biotechnology* 26: 1269-1275 (2008), Zhao et al., *Cell Stem Cell* 3: 475-479 (2008), Feng et al., *Nature Cell Biology* 11: 197-203 (2009), and Hanna et al., *Cell* 133(2): 250-264 (2008), which are hereby incorporated by reference in their entirety.

Integration free approaches, i.e., those using non-integrating and excisable vectors, for deriving iPSCs free of transgenic sequences are particularly suitable in the therapeutic context. Suitable methods of iPSC production that utilize non-integrating vectors include methods that use adenoviral vectors (Stadtfeld et al., "Induced Pluripotent Stem Cells Generated without Viral Integration," *Science* 322: 945-949 (2008), and Okita et al., "Generation of Mouse Induced Pluripotent Stem Cells without Viral Vectors," *Science* 322: 949-953 (2008), which are hereby incorporated by reference in their entirety), Sendi virus vectors (Fusaki et al., "Efficient Induction of Transgene-Free Human Pluripotent Stem Cells Using a Vector Based on Sendi Virus, an RNA Virus That Does Not Integrate into the Host Genome," *Proc Jpn Acad.* 85: 348-362 (2009), which is hereby incorporated by reference in its entirety), polycistronic minicircle vectors (Jia et al., "A Nonviral Minicircle Vector for Deriving Hyman iPS Cells," *Nat. Methods* 7: 197-199 (2010), which is hereby incorporated by reference in its entirety), and self-replicating selectable episomes (Yu et al., "Human Induced Pluripotent Stem Cells Free of Vector and Transgene Sequences," *Science* 324: 797-801 (2009), which is hereby incorporated by reference in its entirety). Suitable methods for iPSC generation using excisable vectors are described by Kaji et al., "Virus-Free Induction of Pluripotency and Subsequent Excision of Reprogramming Factors," *Nature* 458: 771-775 (2009), Soldner et al., "Parkinson's Disease Patient-Derived Induced Pluripotent Stem Cells Free of Viral Reprogramming Factors," *Cell* 136:964-977 (2009), Woltjen et al., "PiggyBac Transposition Reprograms Fibroblasts to Induced Pluripotent Stem Cells," *Nature* 458: 766-770 (2009), and Yusa et al., "Generation of Transgene-Free Induced Pluripotent Mouse Stem Cells by the PiggyBac Transposon," *Nat. Methods* 6: 363-369 (2009), which are hereby incorporated by reference in their entirety. Suitable methods for iPSC generation also include methods involving the direct delivery of reprogramming factors as recombinant proteins (Zhou et al., "Generation of Induced Pluripotent Stem Cells Using Recombinant Proteins," *Cell Stem Cell* 4: 381-384 (2009), which is hereby incorporated by reference in its entirety) or as whole-cell extracts isolated from ESCs (Cho et al., "Induction of Pluripotent Stem Cells from Adult Somatic Cells by Protein-Based Reprogramming without Genetic Manipulation," *Blood* 116: 386-395 (2010), which is hereby incorporated by reference in its entirety).

The methods of iPSC generation described above can be modified to include small molecules that enhance reprogramming efficiency or even substitute for a reprogramming factor. These small molecules include, without limitation, epigenetic modulators such as the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as TGF-β inhibitors and kinase inhibitors (e.g., kenpaullone) (see review by Sommer and Mostoslaysky, "Experimental Approaches for the Generation of Induced Pluripotent Stem Cells," *Stem Cell Res. Ther.* 1:26 doi:10.1186/scrt26 (2010), which is hereby incorporated by reference in its entirety).

Suitable iPSCs derived from adult fibroblasts can be obtained following the procedure described in Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/eurheartj/ehs203 (2012), which is hereby incorporated by reference in its entirety). iPSCs derived from umbilical cord blood cells can be obtained as described in Cai et al., "Generation of Human Induced Pluripotent Stem Cells from Umbilical Cord Matrix and Amniotic Membrane Mesenchymal Cells," *J. Biol. Chem.* 285(15): 112227-11234 (2110) and Giorgetti et al., "Generation of Induced Pluripotent Stem Cells from Human Cord Blood Cells with only Two Factors: Oct4 and Sox2," *Nature Protocols,* 5(4):811-820 (2010), which are hereby incorporated by reference in their entirety. iPSCs derived from bone marrow cells can be obtained using methods described in Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/ eurheartj/ehs203 (Jul. 12, 2012), and Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-

07-298331 (Feb. 4, 2011) which are hereby incorporated by reference in their entirety). iPSCs derived from peripheral blood can be obtained following the methods described in Sommer et al., "Generation of Human Induced Pluripotent Stem Cells from Peripheral Blood using the STEMCCA Lentiviral Vector," *J. Vis. Exp.* 68: e4327 doi:10.3791/4327 (2012), which is hereby incorporated by reference in its entirety. iPS cells contemplated for use in the methods described herein are not limited to those described in the above references, but rather includes cells prepared by any method as long as the cells have been artificially induced from cells other than pluripotent stem cells.

Methods of obtaining highly enriched preparations of oligodendrocyte progenitor cells from the iPSCs or embryonic stem cells (e.g., human embryonic stem cells) that are suitable for treating a neuropsychiatric disorder as described herein are disclosed in WO2014/124087 to Goldman and Wang, and Wang et al., "Human iPSC-Derived Oligodendrocyte Progenitors Can Myelinate and Rescue a Mouse Model of Congenital Hypomyelination," *Cell Stem Cell* 12(2):252-264 (2013), which are hereby incorporated by reference in their entirety.

Briefly, oligodendrocyte progenitor cells are derived from a pluripotent population of cells, i.e., iPSCs or embryonic stem cells, using a protocol that directs the pluripotent cells through serial stages of neural and glial progenitor cell differentiation. Each stage of lineage restriction is characterized and identified by the expression of certain cell proteins. Stage 1 of this process involves culturing the pluripotent cell population under conditions effective to induce embryoid body formation. As described herein, the pluripotent cell population may be maintained in co-culture with other cells, such as embryonic fibroblasts, in an embryonic stem cell (ESC) media (e.g., DMEM/F12 containing a suitable serum replacement and bFGF). The pluripotent cells are passaged before reaching 100% confluence, e.g., 80% confluence, when colonies are approximately 250-300 µm in diameter. The pluripotential state of the cells is readily assessed using markers to SSEA4, TRA-1-60, OCT-4, NANOG, and/or SOX2.

To generate embryoid bodies (EBs) (Stage 2), which are complex three-dimensional cell aggregates of pluripotent stem cells, pluripotent cell cultures are dissociated once they achieved ~80% confluence with colony diameters at or around 250-300 µm. The EBs are initially cultured in suspension in ESC media without bFGF, and then switched to neural induction medium supplemented with bFGF and heparin. To induce neuroepithelial differentiation (Stage 3) EBs are plated and cultured in neural induction medium supplemented with bFGF, heparin, laminin, then switched to neural induction media supplemented with retinoic acid. Neuroepithelial differentiation is assessed by the co-expression of PAX6 and SOX1, which characterize central neural stem and progenitor cells.

To induce pre-oligodendrocyte progenitor cell ("pre-OPCs") differentiation, neuroepithelial cell colonies are cultured in the presence of additional factors including retinoic acid, B27 supplement, and a sonic hedgehog (shh) agonist (e.g., purmophamine). The appearance of pre-OPC colonies is assessed by the presence of OLIG2 and/or NKX2.2 expression. While both OLIG2 and NKX2.2 are expressed by central oligodendrocyte progenitor cells, NKX2.2 is a more specific indicator of oligodendroglial differentiation. Accordingly, an early pre-oligodendrocyte progenitor cell stage is marked by OLIG$^+$/NKX2.2$^-$ cell colonies. OLIG$^+$/NKX2.2$^-$ early pre-OPCs are differentiated into later-stage OLIG$^+$/NKX2.2$^+$ pre-OPCs by replacing retinoic acid with bFGF. At the end of Stage 5, a significant percentage of the cells are pre-OPCs as indicated by OLIG2$^+$/NKX2.2$^+$ expression profile.

Pre-OPCs are further differentiated into bipotential oligodendrocyte progenitor cells by culture in glial induction media supplemented with growth factors such as triiodothyronine (T3), neurotrophin 3 (NT3), insulin growth factor (IGF-1), and platelet-derived growth factor-AA (PDGF-AA) (Stage 6). These culture conditions can be extended for 3-4 months or longer to maximize the production of myelinogenic oligodendrocyte progenitor cells when desired. Cell preparations suitable for transplantation into an appropriate subject are identified as containing PDGFRα$^+$ oligodendrocyte progenitor cells.

Alternative methods of obtaining preparations of oligodendrocyte progenitor cells from the iPSCs or embryonic stem cells that are known in the art can also be used to produce a therapeutic population of cells suitable for treating a neuropsychiatric disorder as described herein. In yet another embodiment, glial progenitor cells can be extracted from embryonic tissue, fetal tissue, or adult brain tissue containing a mixed population of cells directly by using the promoter specific separation technique, as described in U.S. Patent Application Publication Nos. 20040029269 and 20030223972 to Goldman, which are hereby incorporated by reference in their entirety. In accordance with this embodiment, the glial progenitor cells are isolated from ventricular or subventricular zones of the brain or from the subcortical white matter.

In some embodiments, it may be preferable to enrich a cell preparation comprising oligodendrocyte progenitor cells to increase the concentration and/or purity of the therapeutic oligodendrocyte progenitor cells prior to administration. Accordingly, in one embodiment, the A2B5 monoclonal antibody (mAb) that recognizes and binds to gangliosides present on glial progenitor cells early in the developmental or differentiation process can be used to separate glial progenitor cells from a mixed population of cells (Nunes et al., "Identification and Isolation of Multipotential Neural Progenitor Cells From the Subcortical White Matter of the Adult Human Brain.," *Nat Med.* 9(4):439-47 (2003), which is hereby incorporated by reference in its entirety). Using the A2B5 mAb, glial progenitor cells can be separated, enriched, or purified from a mixed population of cell types. In another embodiment, selection of CD140α/PDGFRα positive cells is employed to produce a purified or enriched preparation of bipotential glial progenitor cells. In another embodiment, selection of CD9 positive cells is employed to produce a purified or enriched preparation of oligodendrocyte-biased progenitor cells. In yet another embodiment, both CD140α/PDGFRα and CD9 positive cell selection is employed to produce a purified or enriched preparation of oligodendrocyte progenitor cells. In a further embodiment, selection of CD44 positive cells is employed to produce a purified or enriched preparation of astrocyte-biased progenitor cells (Liu et al., "CD44 Expression Identifies Astrocyte-Restricted Precursor Cells," *Dev. Biol.* 276(1):31-46 (2004), which is hereby incorporated by reference in its entirety.) In another embodiment, both CD140α/PDGFRα and CD44 positive cell selection is employed to produce a purified or enriched preparation of oligodendrocyte progenitor cells. In another embodiment, CD140α/PDGFRα, CD9, and CD44 positive cell selection is employed to produce a purified or enriched preparation of oligodendrocyte progenitor cells.

The administered glial progenitor cell preparation is optionally negative for a PSA-NCAM marker and/or other neuronal lineage markers, and/or negative for one or more inflammatory cell markers, e.g., negative for a CD11 marker, negative for a CD32 marker, and/or negative for a CD36 marker (which are markers for microglia). Optionally, the preparation of glial progenitor cells is negative for any combination or subset of these additional markers. Thus, for example, the preparation of glial progenitor cells is negative for any one, two, three, or four of these additional markers.

In accordance with the method of treating a neuropsychiatric disorder as described herein, the selected preparation of administered glial progenitor cells comprises at least about 80% glial progenitor cells, including, for example, about 80%, 85%, 90%, 95%, 96%, 97%, 98%, 99%, 100% glial progenitor cells. The selected preparation of glial progenitor cells can be relatively devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, multipotent cells, and pluripotential stem cells (like ES cells). Optionally, exemplary cell populations are substantially pure populations of glial progenitor cells.

Positive and/or negative selection for cell markers of interest (e.g., PDGFRα marker, A2B5 marker, and/or a CD44 marker) can be carried out serially or sequentially and can be performed using conventional methods known in the art such as immunopanning. The selection methods optionally involve the use of fluorescence sorting (FACS), magnetic sorting (MACS), or any other method that allows rapid, efficient cell sorting. Examples of methods for cell sorting are taught for example in U.S. Pat. No. 6,692,957 to Goldman, which is hereby incorporated by reference in its entirety, at least for compositions and methods for cell selection and sorting.

Generally, cell sorting methods use a detectable moiety. Detectable moieties include any suitable direct or indirect label, including, but not limited to, enzymes, fluorophores, biotin, chromophores, radioisotopes, colored beads, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes or derivatives thereof.

One of skill in the art readily appreciates how to select for or against a specific marker. Thus, by way of example, a population of cells sorted for a particular marker includes identifying cells that are positive for that particular marker and retaining those cells for further use or further selection steps. A population of cells sorted against a specific marker includes identifying cells that are positive for that particular marker and excluding those cells for further use or further selection steps.

The glial progenitor cell preparations of described herein, including the enriched preparations can be optionally expanded in culture to increase the total number of cells for therapeutic administration. The cells can be expanded by either continuous or pulsatile exposure to PDGF-AA or AB as mitogens that support the expansion of oligodendrocyte progenitor cells; they can be exposed to fibroblast growth factors, including FGF2, FGF4, FGF8 and FGF9, which can support the mitotic expansion of the glial progenitor cells, but which can bias their differentiation to a mixed population of astrocytes as well as oligodendrocytes. The cells can also be expanded in media supplemented with combinations of FGF2, PDGF, and NT3, which can optionally be supplemented with either platelet-depleted or whole serum (see Nunes et al. "Identification and Isolation of Multipotent Neural Progenitor Cells from the Subcortical White Matter of the Adult Human Brain," *Nature Medicine* 9:239-247; Windrem et al., "Fetal and Adult Human Oligodendrocyte Progenitor Cell Isolates Myelinate the Congenitally Dysmyelinated Brain," *Nature Medicine* 10:93-97 (2004), which are incorporated by reference for the methods and compositions described therein).

In accordance with the methods described herein, the glial progenitor cell population is administered bilaterally into multiple sites of the subject being treated as described in Han et al., "Forebrain Engraftment by Human Glial Progenitor Cells Enhances Synaptic Plasticity and Learning Adult Mice," *Cell Stem Cell* 12:342-353 (2013) and Wang et al., "Human iPSCs-Derived Oligodendrocyte Progenitor Cells Can Myelinate and Rescue a Mouse Model of Congenital Hypomyelination," *Cell Stem Cell* 12: 252-264 (2013), which are hereby incorporated by reference in their entirety). Methods for transplanting nerve tissues and cells into host brains are described by Bjorklund and Stenevi (eds), *Neural Grafting in the Mammalian CNS*, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intracerebral, intraventricular, intrathecal, and intracisternal administration.

The glial progenitor cell preparation can be delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g. a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

Delivery of the cells to the subject can include either a single step or a multiple step injection directly into the nervous system. Although adult and fetal oligodendrocyte precursor cells disperse widely within a transplant recipient's brain, for widespread neuropsychiatric disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

In one embodiment, the oligodendrocyte progenitor cell preparation is injected as dissociated cells. In another embodiment, the oligodendrocyte progenitor cell preparation is provided as non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Hank's Balanced Salt Solution, Ringer's solution, dextrose solution, and culture media. The pH of the solution is preferably from about 5 to about 8, and more preferably from about 7 to about 7.5.

The injection of the dissociated cellular transplant can be a streaming injection made across the entry path, the exit path, or both the entry and exit paths of the injection device. Suitable injection devices include cannula, needle, insertion tube, cannula guided by an insertion tube. Automation and stereotactic positioning systems can be used to provide precise delivery to targeted regions with a uniform entry and exit speed and an injection speed and volume.

The number of glial progenitor cells administered to the subject can range from about $10^2$-$10^9$ at each administration (e.g., injection site), depending on the size and species of the recipient, and the volume of tissue requiring cell replacement. Single administration (e.g., injection) doses can span ranges of $1 \times 10^3$-$9 \times 10^3$, $1 \times 10^4$-$9 \times 10^4$, $1 \times 10^5$-$9 \times 10^5$, $1 \times 10^6$-$9 \times 10^6$, $1 \times 10^7$-$9 \times 10^7$, $1 \times 10^8$-$9 \times 10^8$, $1 \times 10^9$-$9 \times 10^9$, $1 \times 10^3$-$9 \times 10^3$, or any amount in total for a transplant recipient patient. In one embodiment, the administered dose is $1 \times 10^7$-$4 \times 10^7$ cells. To achieve such doses, cell preparation having a concentration of 1-$2 \times 10^3$ cells/μl, 1-$2 \times 10^4$ cells/μl, 1-$2 \times 10^5$ cells/μl, 1-$2 \times 10^6$ cells/μl, 1-$2 \times 10^7$ cells/μl of pharmaceutically acceptable carrier are prepared. In one embodiment, the cell preparation for administration has a concentration of $1 \times 10^5$-$2 \times 10^5$ cells/μl in a total volume of about 25 μl to about 50 μl.

Since the CNS is an immunologically privileged site, administered cells, including xenogeneic, can survive and, optionally, no immunosuppressant drugs or a typical regimen of immunosuppressant agents are used in the treatment methods. However, optionally, an immunosuppressant agent may also be administered to the subject prior to and after receiving the cell therapy. Immunosuppressant agents and their dosing regimens are known to one of skill in the art and include such agents as Azathioprine, Azathioprine Sodium, Cyclosporine, Daltroban, Gusperimus Trihydrochloride, Sirolimus, Mycophenolate mofetil (MMF), and Tacrolimus. In one embodiment, a combination of any of the aforementioned immunosuppressant agents are administered to the subject. In one embodiment, a combination of MMF and tacrolimus are administered to the subject. Dosages ranges and duration of the regimen can be varied with the disorder being treated; the extent of rejection; the activity of the specific immunosuppressant employed; the age, body weight, general health, sex and diet of the subject; the time of administration; the route of administration; the rate of excretion of the specific immunosuppressant employed; the duration and frequency of the treatment; and drugs used in combination. One of skill in the art can determine acceptable dosages for and duration of immunosuppression. The dosage regimen can be adjusted by the individual physician in the event of any contraindications or change in the subject's status.

In one embodiment, one or more immunosuppressant agents are administered to the subject starting at 10 weeks prior to cell administration. In one embodiment, the one or more immunosuppressant agents are administered to the subject starting at 9 weeks, 8 weeks, 7 weeks, 6 weeks, 5 weeks, 4 weeks, 3 weeks, 2 weeks, 1 week, 7 days, 6 days, 5 days, 4 days, 3 days, 2 days, 1 day, <24 hours prior to cell administration. In one embodiment, one or more immunosuppressant agents are administered to the subject starting on the day of cell administration and continuing for 1, 2, 3, 4, 5, 6, 7, 8, 9, 10, 11, 12 months post administration. In one embodiment, the one or more immunosuppressant agents are administered to the subject for >1 year following administration.

As used herein, "treating" or "treatment" refers to any indication of success in amelioration of an injury, pathology, or condition, including any objective or subjective parameter such as abatement; remission; diminishing of symptoms or making the injury, pathology, or condition more tolerable to the patient; slowing the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" includes the administration of glial progenitor cells to prevent or delay, to alleviate, or to arrest or inhibit development of the symptoms or conditions associated with schizophrenia, autism spectrum disorder, bipolar disorder, or any other neuropsychiatric disorder. "Therapeutic effect" refers to the reduction, elimination, or prevention of the disease, symptoms of the disease, or side effects of a disease, condition or disorder in the subject. Treatment may be prophylactic (to prevent or delay the onset or worsening of the disease, condition or disorder, or to prevent the manifestation of clinical or subclinical symptoms thereof) or therapeutic suppression or alleviation of symptoms after the manifestation of the disease, condition or disorder.

A "dosage effective to treat," as used herein refers to the amount of cells that is effective for production of a desired result. This amount varies, for example, depending upon the health and physical condition of the individual to be treated, the mental and emotional capacity of the individual, the degree of protection desired, the formulation, the attending physician's assessment of the medical situation, and other relevant factors.

Another aspect of the present disclosure relates to a method of treating a neuropsychiatric disorder. This method includes selecting a subject having the neuropsychiatric disorder and administering, to the selected subject, a potassium ($K^+$) channel activator at a dosage effective to restore normal brain interstitial glial $K^+$ levels in the selected subject and treat the neuropsychiatric disorder.

Suitable subjects as well as neuropsychiatric disorders suitable for treatment in accordance with this aspect of the disclosure are disclosed supra. Exemplary neuropsychiatric disorders to be treated using the methods described herein include, without limitation, schizophrenia, autism spectrum disorders, and bipolar disorder.

As described herein, neuropsychiatric disorders, such as schizophrenia, involve the dysregulated expression of numerous glial progenitor cell genes that contribute and/or cause impaired glial cell differentiation. In particular, the expression levels of numerous potassium channel genes are significantly downregulated in the disease state. These results indicate a role for dysregulated glial potassium channel function and glial potassium levels in neuropsychiatric disorders like schizophrenia, autism disorders, and bipolar disorders. Accordingly, a subject having a neuropsychiatric disorder will benefit therapeutically from the administration of one or more $K^+$ channel activators to restore normal, healthy brain interstitial glial $K^+$ levels.

As used herein, a "$K^+$ channel" refers to a protein or polypeptide that is involved in receiving, conducting, and transmitting signals in an excitable cell. Potassium channels are typically expressed in electrically excitable cells, including glial cells, and can form heteromultimeric structures, e.g., composed of pore-forming and regulatory subunits. Examples of potassium channels include: (1) the voltage-gated potassium channels, (2) the inwardly rectifying channels, (3) the tandem pore channels, and (3) the ligand-gated channels. For a detailed description of potassium channels, see Kandel E. R. et al., *Principles of Neural Science*, second edition, (Elsevier Science Publishing Co., Inc., N.Y. (1985)), which is hereby incorporated by reference in its entirety.

Potassium regulation in the central nervous system is mediated by net potassium uptake and potassium spatial buffering (Kofuji and Newman., "Regulation of Potassium by Glial Cells in the Central Nervous System," *Springer Science & Business Media* (2008), which is hereby incorporated by reference in its entirety). For $K^+$ uptake, excess extracellular $K^-$ is taken up and sequestered within glial cells by the action of the $Na^-$, $K^+$-ATPase, or by $K^+$ flux through transporters or $K^+$ channels (Kofuji and Newman., "Regulation of Potassium by Glial Cells in the Central Nervous System," *Springer Science & Business Media* (2008), which is hereby incorporated by reference in its entirety). In spatial buffering, $K^+$ is transferred from regions of elevated $K^+$ concentration to regions of lower $K^+$ concentration by a current flow through glial cells (i.e., glial $K^+$ conductance) (see Orkand et al., "Effect of Nerve Impulses on the Membrane Potential of Glial Cells in the Central Nervous System of Amphibia," *J Neurophysiol* 29:788-806 (1966), which is hereby incorporated by reference in its entirety).

In accordance with this aspect of the disclosure, the selected subject having the neuropsychiatric disorder has dysregulated glial $K^+$ channel function characterized by defective glial $K^+$ conductance, defective glial $K^+$ uptake, and/or defective glial $K^+$ channel expression.

Several $K^+$ channel activators that act either specifically or non-specifically on $K^+$ channels are known in the art and are suitable for use in the present invention to restore channel activity. Such $K^+$ activators include, without limitation, ethyl [2-amino-4-[[(4-fluorophenyl)methyl]amino]phenyl]carbamate (retigabine), N-[2-Amino-6-[[4-fluorophenyl)methyl]amino]-3-pyridinyl]carbamic acid ethyl ester maleate (flupirtine), N-[3,5-Bis(trifluoromethyl)phenyl]-N'-[2,4-dibromo-6-(2H-tetrazol-5-yl)phenyl]urea (NS 5806), N-(2-Chloro-5-pyrimidinyl)-3,4-difluorobenzamide (ICA 69673), 4-Chloro-N-(6-chloro-3-pyridinyl)benzamide (ICA 110381), 5-(2-Fluorophenyl)-1,3-dihydro-3-(1H-indol-3-ylmethyl)-1-methyl-2H-1,4-benzodiazepin-2-one (L-364373), N-(2,4,6-Trimethylphenyl)-bicyclo[2.2.1]heptane-2-carboxamide (ML 213), (2R)—N-[4-(4-Methoxyphenyl)-2-thiazolyl]-1-[(4-methylphenyl)sulfonyl]-2-piperidinecarboxamide (ML 277), N,N-Bis[2-hydroxy-5-(trifluoromethyl)phenyl]urea (NS 1643), N-[4-Bromo-2-(1H-tetrazol-5-yl)phenyl]-N'-[3-(trifluoromethyl)phenyl]-urea (NS 3623), 5-(2,6-Dichloro-5-fluoro-3-pyridinyl)-3-phenyl-2-(trifluoromethyl)-pyrazolo[1,5-a]pyrimidin-7(4H)-one (QO58), 2-[[4-[2-(3,4-Dichlorophenyl)ethyl]phenyl]amino]benzoic acid (PD 118057), trans-3,4-dihydro-3-hydroxy-2,2-dimethyl-4-(2-oxo-1-pyrrolidinyl)-2H-1-benzopyran-6-carbonitrile (cromakalim), 7-Chloro-3-methyl-2H-1,2,4-benzothiadiazine 1,1-dioxide (diazoxide), (3S,4R)-3,4-dihydro-3-hydroxy-2,2-dimethyl-4-(2-oxo-1-pyrrolidinyl)-2H-1-benzopyran-6-carbonitrile (levcromakalim), 6-(1-Piperidinyl)-2,4-pyrimidinediamine 3-oxide (minoxidil), N-(3,4-Difluorophenyl)-N'-(3-methyl-1-phenyl-1H-pyrazol-5-yl)urea (ML 297), N-[2-(Nitrooxy)ethyl]-3-pyridinecarboxamide (nicorandil), N-cyano-N'-(1,1-dimethylpropyl)-N"-3-pyridylguanidine (P1075), (Z)-5-Chloro-2,3-dihydro-3-(hydroxy-2-thienylmethylene)-2-oxo-1H-indole-1-carboxamide (tenidap), N-[(3S,4R)-6-Cyano-3,4-dihydro-3-hydroxy-2,2-dimethyl-2H-1-benzopyran-4-yl]-N-hydroxyacetamide (Y-26763), N-[(3S,4R)-6-Cyano-3,4-dihydro-3-hydroxy-2,2-dimethyl-2H-1-benzopyran-4-yl]-N-(phenylmethoxy)acetamide (Y-27152), N-(4-Phenylsulfonylphenyl)-3,3,3-trifluoro-2-hydroxy-2-methylpropanamide (ZM 226600), N-(6-chloro-pyridin-3-yl)-3,4-difluoro-benzamide (ICA-27243), ICA-105665, 2-(2,6-dichloranilino) phenylacetic acid (diclofenac) and its structural analogs (e.g., NH6), (3R,4R)-4-[3-(6-methoxyquinolin-4-yl)-3-oxo-propyl]-1-[3-(2,3,5-trifluoro-phenyl)-prop-2-ynyl]-piperidine-3-carboxylic acid (RPR260243), 2-[[2-(3,4-Dichlorophenyl)-2,3-dihydro-1H-isoindol-5-yl]amino]nicotinic acid (PD307243), nitrous oxide, halothane, 17β-estradiol, dithiothreitol, naringin, (3S)-(+)-(5-Chloro-2-methoxyphenyl)-1,3-dihydro-3-fluoro-6-(trifluoromethyl)-2H-indole-2-one (BMS 204352), isoflurane, 2-halogenated ethanols, halogenated methanes, sevoflurane, and desflurane.

In one embodiment of this aspect of the disclosure, the administered $K^+$ channel activator increases the activity of glial G protein-activated inward rectifier $K^+$ channels. The G-protein activated inward rectifying potassium ($K^+$) channels, GIRKs, are members of a larger family of inward-rectifying potassium channels, Kirs. As the name suggests, GIRK channels can be activated by pertussis toxin-sensitive G-protein-coupled receptors of the Gi subtype through interactions with the G-protein's β/γ subunits1-3. However, GIRK regulation is complex and both positive and negative modulation has been observed through Gs and Gq GPCRs as well as via other indirect mechanisms. GIRK regulation by GPCRs is believed to be linked to biological effects of a variety of GPCR agonists including opioids, acetylcholine, and the GABA receptor agonist, baclofen.

The GIRK channels are comprised of four subunits, GIRK1-4 (aka Kir3.1-3.4), encoded by the genes KCNJ3, KCNJ6, KCNJ9, and KCNJ5, respectively. These four subunits can form homo and heterotetramers with unique biophysical properties, regulation, and distribution. GIRKs are found widely expressed in the brain with the GIRK1/2 subunit combination being the most common and widespread within the cortex, hippocampus, cerebellum, and various other brain regions, while other subunit combinations, such as GIRK1/4, show very limited expression in the brain.

Exemplary agents that activate glial G protein-activated inward rectifier $K^+$ channels (either specifically or non-specifically) that are suitable for use in the treatment of a neuropsychiatric disorder include, without limitation, flupirtine, nitrous oxide, halothane, 17β-estradiol, dithiothreitol, naringin, and derivatives and analogues thereof.

In another embodiment, the administered $K^+$ channel activator increases the activity of glial $K^+$ voltage-gated channels. The $K^+$ voltage-gated (Kv) family of channels includes, among others: (1) the delayed-rectifier potassium channels, which repolarize the membrane after each action potential to prepare the cell to fire again; and (2) the rapidly inactivating (A-type) potassium channels, which are active predominantly at subthreshold voltages and act to reduce the rate at which excitable cells reach firing threshold. In addition to being critical for action potential conduction, Kv channels also control the response to depolarizing, e.g., synaptic, inputs and play a role in neurotransmitter release. As a result of these activities, voltage-gated potassium channels are key regulators of neuronal excitability (Hille B., *Ionic Channels of Excitable Membranes*, Second Edition, Sunderland, M A: Sinauer, (1992), which is hereby incorporated by reference in its entirety).

There is tremendous structural and functional diversity within the Kv potassium channel superfamily. This diversity is generated both by the existence of multiple genes and by alternative splicing of RNA transcripts produced from the same gene. Nonetheless, the amino acid sequences of the known Kv potassium channels show high similarity. All appear to be comprised of four, pore forming a-subunits and some are known to have four cytoplasmic (β-subunit) polypeptides (Jan L. Y. et al. *Trends Neurosci* 13:415-419 (1990); Pongs, O. et al. *Sem Neurosci* 7:137-146 (1995), which are hereby incorporated by reference in their entirety).

Thus, in one embodiment, the administered $K^+$ channel activator increases the activity of glial A-type voltage-gated $K^+$ channels. Exemplary agents that activate glial A-type voltage-gated $K^+$ channels (either specifically or non-specifically) that are suitable use in the treatment of a neuropsychiatric disorder include, without limitation, N-[3,5-Bis(trifluoromethyl)phenyl]-N'-[2,4-dibromo-6-(2H-tetrazol-5-yl)phenyl]urea (NS5806) and derivatives and analogues thereof.

In another embodiment, the administered $K^+$ channel activator increases the activity of glial delayed rectifier $K^+$ channels. Exemplary delayed rectifier $K^+$ channel activators for use in this aspect of the present disclosure include, without limitation, retigabine and derivatives and analogues thereof.

The $K^+$ channel activator may also affect glial tandem pore domain $K^+$ channels. Tandem pore domain $K^+$ channels comprise a family of 15 members from what is known as "leak channels." These channels allow the constant passage of $K^+$ and are encoded by KCNK1 and KCNK18.

Thus, in one embodiment, the administered $K^+$ channel activator increases the activity of glial tandem pore domain $K^+$ channels, including the potassium leak channels encoded by KCNK1 through KCNK18 inclusive. Exemplary agents that activate tandem pore domain $K^+$ channels (either specifically or non-specifically) that are suitable for use in the treatment of a neuropsychiatric disorder include, without limitation halothane, isoflurane, 2-haolgenated ethanols, halogenated methanes, sevoflurane, and desflurane and derivatives and analogues thereof.

In one embodiment, the $K^+$ channel activator is not a Kv7 (KCNQ) $K^+$ channel activator. In another embodiment, the $K^+$ channel activator is specific for glial KCNQ channels, i.e., a KCNQ channel activator that is selective for or targeted to activating KCNQ channels on glial cells, but does not activate KCNQ channels on non-glial cells.

In accordance with the method of treating a subject having a neuropsychiatric disorder, the $K^+$ channel activator can be administered to the subject either as a free base or as a pharmaceutically acceptable acid addition salt. In the latter case, the hydrochloride salt is generally preferred but other salts derived from organic or inorganic acids may be also used. Examples of such acids include, without limitation, hydrobromic acid, phosphoric acid, sulphuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like.

The total daily dosage of the $K^+$ channel activator that is administered to a subject should be at least the amount required to prevent, reduce or eliminate one or more of the symptoms associated with the neuropsychiatric disorder. The typical daily dosage will be between 20 and 400 mg and, in general, the daily dosage should not exceed 1600 mg. Higher doses are tolerated by some patients and daily dosages of 2,000 mg or more may be considered in a subject receiving concomitant drug treatment with agents that may lower the concentration and half-life of the $K^+$ channel activator. These dosages are simply guidelines and the actual dose selected for an individual subject will be determined by the attending physician based upon clinical conditions and using methods well-known in the art. The suitable $K^+$ channel activator may be provided in either single or multiple dosage regimens or on an as needed regime. For example, a subject may be administered a $K^+$ channel activator daily, weekly, or monthly. Alternatively, the subject may need to be administered the $K^+$ channel activator once, twice, or greater than twice daily depending on the particular neuropsychiatric condition, the stage or progression of the condition, individual symptoms, and the extent and duration of relief achieved.

Suitable routes of administration of the $K^+$ channel activator include, without limitation, subcutaneous, intramuscular, intravenous, or inhalation. Accordingly, suitable dosage forms include powders, aerosols, parenteral aqueous suspensions, solutions and emulsions. Sustained release dosage forms may also be used. The K+ channel activator may be administered as either the sole active agent or in combination with other therapeutically active drugs used to treat the neuropsychiatric disorder or to reduce the progression of the neuropsychiatric disorder.

Another aspect of the present disclosure relates to a non-human mammal model of a neuropsychiatric disorder. This non-human mammal has at least 30% of all of its glial cells in its corpus callosum being human glial cells derived from a human patient with a neuropsychiatric disorder and/or at least 5% of all of its glial cells in the white matter of its brain and/or brain stem being human glial cells derived from a human patient with a neuropsychiatric disorder.

The non-human mammal comprising human glial cells derived from a patient with a neuropsychiatric disorder exhibits the behavioral characteristics and phenotypes associated with the neuropsychiatric disorder. For example, when the neuropsychiatric disorder is schizophrenia, the non-human mammal exhibits the behavioral phenotype of schizophrenia which is characterized by diminished pre-pulse inhibition, higher anxiety, and social avoidance as described in the Examples herein.

In one embodiment, the human glial cells constitute at least 50%, of all glial cells in the corpus callosum of the non-human mammal. In another embodiment, the human glial cells constitute at least 70%, of all glial cells in the corpus callosum of the non-human mammal. In another embodiment, the human glial cells constitute at least 90%, of all glial cells in the corpus callosum of the non-human mammal. In one embodiment, at least 10% of all glial cells in the white matter of the non-human mammal's brain and/or brain stem are human glial cells. In another embodiment, at least 15% of all glial cells in the white matter of the non-human mammal's brain and/or brain stem are human glial cells. In another embodiment, at least 20% or more of all glial cells in the white matter of the non-human mammal's brain and/or brain stem are human glial cells. In another embodiment, at least 50% of all glial cells in the cerebellar white matter are human glial cells.

The human neuropsychiatric disorder specific glial cells of the non-human mammal model described herein may be derived from any suitable source of glial cells, such as, for example and without limitation, human induced pluripotent stem cells (iPSCs) derived from a subject having a neuropsychiatric disorder, or from glial progenitor cells isolated from brain tissue of a subject having a neuropsychiatric disorder using the methods described above.

In accordance with the method of producing the non-human mammal model of a human neuropsychiatric disorder, the selected preparation of administered human neuropsychiatric disorder specific glial cells comprise at least about 80% glial cells, including, for example, about 80%, 85%, 90%, 95%, 96%, 97%, 98%, 99%, 100% glial cells. The selected preparation of glial cells can be relatively devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, and pluripotential stem cells (like ES cells). Optionally, example cell populations are substantially pure populations of glial cells.

Another aspect relates to a method of producing non-human mammal model of a neuropsychiatric disorder with human diseased glial cells replacing native glial cells in the non-human mammal brain. This method involves providing a population of isolated human glial cells derived from a patient with a neuropsychiatric disorder, introducing the population of isolated human glial cells into multiple locations within the forebrain and/or brain stem of a non-human mammal, and recovering a non-human mammal with human glial cells replacing native glial cells in the brain.

Methods of making a non-human mammal using human fetal cells are described in U.S. Pat. No. 7,524,491 to Goldman, and Windrem et al., "Neonatal Chimerization With Human Glial Progenitor Cells Can Both Remyelinate and Rescue the Otherwise Lethally Hypomyelinated Shiverer Mouse," Cell Stem Cell 2:553-565 (2008), which are hereby incorporated by reference in their entirety. See also US Patent Application Publication No. US20160317681 to Goldman, which is hereby incorporated by reference in its entirety.

The non-human mammal can be any neonatal, juvenile, or adult non-human mammal. Exemplary non-human mammals include, without limitation, mice, rats, guinea pigs and other small rodents, dogs, cats, sheep, goats, and monkeys. In one embodiment the non-human mammal is a mouse. Suitable strains of mice commonly used as models of disease include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SIL mice, B6C3F1 mice, BDF1 mice, CDF1 mice, CB6F1 mice, CF-1 mice, Swiss Webster mice, SKH1 mice, PGP mice, and B6SJL mice.

The human neuropsychiatric disorder specific glial cells can be introduced into multiple locations within the forebrain and/or brain stem of a non-human mammal. Suitable methods of administration include, without limitation intracerebral, intraventricular, intrathecal, and intracisternal administration. The neuropsychiatric disorder specific glial cells may alternatively be administered via intraparenchymal or intracallosal transplantation. The number of human neuropsychiatric disorder specific glial cells to be introduced into the non-human mammal can range between $10^3$-$10^5$ cells.

It is desirable that the non-human mammal host accepts the human glial cells with little or no adverse immune recognition. Therefore, in some embodiments, the non-human mammal is immuno-incompetent, immuno-deficient, or immuno-suppressed.

Immunosuppression can be achieved either through the administration of immunosuppressive drugs such as cyclosporin, sirolimus, or tacrolimus, or through strategies employing locally applied immunosuppressants. Local immunosuppression is disclosed by Gruber, Transplantation 54:1-11 (1992), which is hereby incorporated by reference in its entirety. U.S. Pat. No. 5,026,365 to Rossini, which is hereby incorporated by reference in its entirety, discloses encapsulation methods also suitable for local immunosuppression.

As an alternative to employing immunosuppression techniques, methods of gene replacement or knockout using homologous recombination, as taught by Smithies et al. Nature 317:230-234 (1985), which is hereby incorporated by reference in its entirety, can be applied to donor glial cells for the ablation of major histocompatibility complex (MHC) genes. Donor glial cells lacking MHC expression would allow for the transplantation of an enriched glial cell population across allogeneic and perhaps even xenogenic, histocompatibility barriers without the need to immunosuppress the recipient. General reviews and citations for the use of recombinant methods to reduce antigenicity of donor cells are also disclosed by Gruber, Transplantation 54:1-11 (1992), which is hereby incorporated by reference in its entirety. Exemplary approaches to reduce immunogenicity of transplants by surface modification are disclosed in WO92/04033 to Faustman, which is hereby incorporated by reference in its entirety.

Alternatively, the immunogenicity of the transplanted cells may be reduced by using any non-human mammal host that possesses a genetic mutation rendering it immunodeficient. Exemplary animal models include those having a mutation which disrupts the recombination activating gene 2 (Rag2) (Shinkai et al., Cell 68:855-867 (1992), which is hereby incorporated by reference in its entirety) or the Rag1 gene (Mombaerts et al., Cell 68:869-877 (1992) and Schultz et al., Transplantation 76:1036-42 (2003), which are hereby incorporated by reference in their entirety). Other immunodeficient animal models useful for practicing the producing the non-human mammals described herein include any of the severe combined immunodeficient mice (SCID), having a mutation in the Prkdc gene. Preferred SCID mouse models for use in aspect include the NOD-SCID, the NOD-SCID-IL2rg, and the NOG (NOD-SCID/$\gamma c^{null}$) mouse models. Additionally, the Nude mouse models, carrying a mutation in the Foxn1 gene are also useful for producing the non-human mammal model of a human neuropsychiatric disorder.

After the population of isolated human neuropsychiatric disorder specific glial cells is introduced into the forebrain and/or brain stem of the non-human mammal, the non-human mammal is recovered. As used herein, the term "recovering the non-human mammal" refers to a process or means by which the introduced human glial cells are allowed to functionally engraft into the brain of the non-human mammal. Exemplary percentages of human glial cells present in the white matter and/or corpus callosum of the brain and brain stem of the recovered non-human mammal model are described supra.

Another aspect of the present disclosure relates to a method of identifying an agent suitable for treating a neuropsychiatric disorder that involves providing a non-human mammal model of the neuropsychiatric disorder as described supra and providing a candidate agent. The method further includes administering the candidate agent to the non-human mammal and assessing, as a result of said administering, the therapeutic potential of the candidate agent as suitable for treating the neuropsychiatric disorder.

EXAMPLES

The examples below are intended to exemplify the practice of embodiments of the disclosure but are by no means intended to limit the scope thereof.

Materials and Methods for Examples

Patient identification, protection and sampling. Patients from which these lines were derived were diagnosed with disabling degrees of schizophrenia with onset in early adolescence; all patients and their guardians were consented by a child psychiatrist (RLF) under an approved protocol of Case Western School of Medicine, blinded as to subsequent line designations, and no study investigators had access to patient identifiers.

iPSC line derivation and production of GPCs. Punch biopsies of the skin were obtained from patients with juvenile onset schizophrenia (ages 10 to 17 years old) and controls (ages 24 to 32 years old). Induced pluripotent stem cells (iPSC) lines were derived from the patient samples using an excisable floxed polycistronic hSTEMCCA lentiviral vector. Short tandem repeat (STR)-based DNA fingerprinting was used to confirm iPSC identity, as a match to original patient or control donor. Additional genotyping was performed using Illumina Omni5 SNP arrays. The iPSCs were then driven toward a glial progenitor cell (GPC) fate using previously described protocols (Wang et al., "Human iPSC-Derived Oligodendrocyte Progenitor Cells can Myelinate and Rescue a Mouse Model of Congenital Hypomyelination," *Cell Stem Cell* 12:252-264 (2013), which is hereby incorporated by reference in its entirety). Cells were harvested between 160-240 DIV, by which time most typically expressed the bipotential GPC marker PDGFαR/CD140a, while the remainder were A2B5+/CD140a– astrocytes. The karyotypes of all iPSC lines were assessed during glial differentiation to ensure genotypic stability of the cells utilized in all experiments presented here (karyotyping by WiCell, Madison, Wis.). All iPSCs showed a normal karyotype, except for line 51, which was found to have a balanced Robertsonian translocation of chromosome 13, an anomaly previously associated with juvenile-onset schizophrenia (Graw et al., "Isochromosome 13 in a Patient with Childhood-Onset Schizophrenia, ADHD, and Motor Tic Disorder," *Mol Cytogenet* 5:2 (2012), which is hereby incorporated by reference in its entirety).

Host transplantation. Homozygous shiverer mice (The Jackson Laboratory, Bar Harbor, Me.) were crossed with homozygous rag2-null immunodeficient mice (Shinkai et al., "RAG2-Deficient Mice Lack Mature Lymphocytes Owing to Inability to Initiate V(D)J Rearrangement," *Cell* 68:855-867 (1992), which is hereby incorporated by reference in its entirety) on the C3h background (Taconic, Germantown, N.Y., USA) to generate shi/shi×rag2$^{-/-}$ myelin-deficient, immunodeficient mice (Windrem et al., "Neonatal Chimerization with Human Glial Progenitor Cells can both Remyelinate and Rescue the Otherwise Lethally Hypomyelinated Shiverer Mouse," *Cell Stem Cell* 2:553-565 (2008), which is hereby incorporated by reference in its entirety). In addition, rag1$^{-/-}$ normally-myelinated immunodeficient mice (B6.129S7-Rag1$^{tm1Mom}$/J), were obtained from the Jackson Laboratory and bred in the lab. Suspensions of single-cells or small clusters of hiPSC-derived GPCs were spun down to 100,000 cells/μl. Neonates were anesthetized by cooling, and transplanted bilaterally in the corpus callosum with a total of 200,000 cells, as described (Windrem et al., "Fetal and Adult Human Oligodendrocyte Progenitor Cell Isolates Myelinate the Congenitally Dysmyelinated Brain," *Nat. Med.* 10:93-97 (2004), which is hereby incorporated by reference in its entirety). At 3 months of age (shi/shi×rag2$^{-/-}$) or after completion of behavioral testing at 6-9 months (rag1$^{-/-}$ only), transplanted mice were anesthetized with pentobarbital, then perfusion fixed with cold HBSS$^{+/+}$ followed by 4% paraformaldehyde (PF) with a 2 hour post-fixation in cold PF. All procedures were approved by the University of Rochester's Committee on Animal Resources.

Immunolabeling. Brains were cryopreserved, embedded in OCT (Tissue-Tek OCT, Sakura Finetek, Torrance, Calif.) and sectioned at 20 μm, either sagittally or coronally, on a cryostat. Human cells were identified with mouse antihuman nuclei, clone 235-1 at 1:800 (MAB1281, EMD Millipore, Billerica, Mass.). Myelin basic protein was labeled with rat anti-MBP at 1:25 (Ab7349, Abcam, Cambridge, Mass.), oligodendrocyte progenitors with anti-human-specific PDGF Receptor a (D13C6, XP® rabbit mAb 5241, 1:300, Cell Signaling Technology), oligodendrocytes with mouse anti-human-specific transferrin (clone HT1/13.6.3, 08691231, MP Biomedicals), astrocytes with anti-human-specific GFAP (SMI 21 at 1:1000, Covance, Princeton, N.J.). Alexa Fluor secondary antibodies, goat anti-mouse, rat, and rabbit 488, 568, 594, and 647 were used at 1:400 (Life Technologies, Carlsbad, Calif.).

Antibodies and Dilutions Used

| Antigen | Name | Dilution | Catalog | Company |
| --- | --- | --- | --- | --- |
| hGFAP | Mouse anti-human (specific) GFAP | 1:500 | SMI-21R | Covance |
| hNA | Mouse anti-human nuclear antigen, cl. 235-1 | 1:800 | MAB1281 | Millipore |
| hNG2 | Mouse anti-NG2, clone 9.2.27 | 1:200 | MAB2029 | Millipore |
| MBP | Rat anti-Myelin Basic Protein | 1:25 | ab7349 | Abcam |
| Olig2 | Rabbit anti-Olig2 | 1:500 | RA25017 | Neuromics |
| PDGFRα | Rabbit anti-PDGFRα, clone D13C6 | 1:300 | 5241S | Cell Signl |
| Transferrin | Mouse anti-human transferrin | 1:800 | ab9538 | Abcam |
| Secondary antibodies | AlexaFluor 568 Goat anti-Mouse IgG (H + L) | 1:400 | A-11031 | Invitrogen |
| | AlexaFluor 568 Goat anti-Mouse IgG1 | 1:400 | A-21124 | Invitrogen |
| | AlexaFluor 488 Goat anti-Mouse IgG (H + L) | 1:400 | A-11029 | Invitrogen |
| | AlexaFluor 488 Goat anti-Mouse IgG1 | 1:400 | A-21121 | Invitrogen |
| | AlexaFluor 568 Goat anti-Rabbit IgG (H + L) | 1:400 | A-11036 | Invitrogen |
| | AlexaFluor 488 Goat anti-Rabbit IgG (H + L) | 1:400 | A-11034 | Invitrogen |
| | Cy5 Goat anti-Rat | 1:400 | A10525 | Invitrogen |
| | AlexaFluor 568 Goat anti-Rat IgG (H + L) | 1:400 | A-11077 | Invitrogen |
| | AlexaFluor 488 Goat anti-Rat IgG (H + L) | 1:400 | A-11006 | Invitrogen |

Western blots. GPCs derived from CWRU22 and CWRU51 were sorted by FACS for CD140a at DIV160-200, directly into cell lysis buffer (NP40, Invitrogen, FNN0021) with protease inhibitor (Roche, 183617025) on ice. The insoluble fraction was removed by centrifugation at 12,000 g for 5 minutes at 4° C., and the supernatant analyzed for total protein with BCATM Protein Assay Kit (Thermo, 23227). 10 μg sample aliquots were separated on 4-12% gradient gels by SDS-PAGE electrophoresis (XCell Sure-Lock, Invitrogen, 071210). Separated protein was transferred to PVDF membranes, which were blocked with 5% dry milk and incubated sequentially with a rabbit polyclonal anti-neurexin-1 antisera (Millipore, ABN161-1, 1:1000) at 4° C. overnight, then washed and followed serially by a mouse monoclonal anti-ß actin (Abcam, ab173838, 1:5000) at RT for 1 h, and anti-mouse and anti-rabbit secondary antibodies (GE Healthcare, 95107-322 and 95107-328, 1:10000) at RT for 1 h. Membranes were visualized by chemiluminescence (Mix ECLTM Reagent, GE Healthcare, RPN2236) through exposure of X-ray film. Experiments were repeated 3 times, with 3 different sets of cells.

Imaging and Quantitative histology. For mapping the distribution of human nuclei, or photographing gross distribution of myelin at low power, whole brain sections were imaged on a Leica LMD 6500. Imaging for phenotypic counts was performed on an Olympus BX51 driven by Stereo Investigator software (MBF, Williston, Vt.).

Astrocyte morphometrics. Shiverer×rag2-null mice were sacrificed at 4.5 months of age and their white matter astrocyte morphologies assessed. 150 μm thick coronal slices were taken by Vibratome at Bregma −1.0 mm from control (22, 37 and C27) or SCZ (51, 164, 193) hGPC-engrafted mice, incubated in mouse anti-hGFAP for 1 week, then 4 hrs in Alexa 568 goat anti-mouse. The slices were mounted on slides and imaged at 100× by confocal (Leica SP8). The images were traced using Neurolucida 360 (MicroBrightfield, Inc.). Individual astrocytes were selected from the middle of the corpus callosum at mid-depth so as to capture cells and their processes in their entirety. Nine cells/brain were analyzed by Neurolucida with Sholl analysis, as 3 cells/slice and 3 slices/brain, taken at 500, 1000, and 1500 μm lateral of the midline. Two or three brains were assessed for each of three lines produced from separate patients, for a total of 8 brains and 72 traced cells/condition, for both CTRL and SCZ-engrafted groups. For Sholl analysis, concentric shells placed at successively increasing diameters of 5 μm were centered on the cell body, and the number of intersections between cell processes and shells counted (Sholl, D A., "Dendritic Organization in the Neurons of the Visual and Motor Cortices of the Cat," *J. Anat.* 87:387-406 (1953), which is hereby incorporated by reference in its entirety). For the assessment and quantitative description of astrocytic fiber 3D architecture, Fan-in analysis (MBF Biosciences) was used as previously described for studies of dendritic topology (Dang et al., "Formoterol, a Long-Acting Beta2 Adrenergic Agonist, Improves Cognitive Function and Promotes Dendritic Complexity in a Mouse Model of Down Syndrome," *Biol. Psychiatry* 75:179-188 (2014), which is hereby incorporated by reference in its entirety).

Myelin luminance analysis. To measure forebrain myelination, luminance analysis based on measurement of myelin basic protein (MBP) immunofluorescence. Evenly-spaced and uniformly sampled coronal sections were stained for MBP as described, and images taken at 10× using a Nikon Ni-E and Nikon DS-Fi1 camera. The corpus callosum was selected as region of interest, and mean intensity values were obtained using NIS Elements v.4.5.

Behavior. Behavioral tests were scored using either ANY-maze (Stoelting, Wood Dale, Ill.) or EthoVision (Noldus). Behavioral testing began at either 25 weeks (for pre-pulse inhibition) or 30-36 weeks (all other tests), and typically lasted 3 weeks; starting age was matched between experimentals and controls. A total of 6-12 recipient mice were engrafted and tested per cell line, or 17-36 mice per group for each behavioral comparison, with a roughly equal balance of male (M) and female (F) recipients. Tests were performed in the same sequence for all mice, and included:

1) Elevated Plus Maze. Each test mouse was placed in the center of a raised, plus-shaped apparatus, consisting of 2 enclosed arms and 2 open arms, facing an open arm (Walf et al., "The Use of the Elevated Plus Maze as an Assay of Anxiety-Related Behavior in Rodents," *Nat Protoc* 2:322-328 (2007), which is hereby incorporated by reference in its entirety). Each tested mouse was videotaped and scored for time spent in the open vs. closed arms. 2) Three chamber social choice. The test apparatus is a plexiglass enclosure divided into thirds with connecting doors (Ugo Basile, Italy) (Yang et al., "Automated Three-Chambered Social Approach Task for Mice," *Curr Protoc Neurosci*, Chapter 8, Unit 8, 26 (2011), which is hereby incorporated by reference in its entirety). Each test mouse was first acclimated to the central chamber or 5 minutes. The doors to the outer chambers were then removed, and the test mouse allowed to explore all three chambers for 10 minutes. The test mouse was then guided back to the central chamber, and a same sex and age stranger mouse was placed in a cylindrical container in one side chamber, while an empty cylindrical container was placed in the opposite side chamber. The mouse was then recorded for 10 minutes, and scored with respect to the amount of time it spent with the stranger mouse vs. the empty compartment. 3) Novel Object Recognition. Each test mouse was placed in an empty 1 ft$^2$ testing chamber for 5 minutes to acclimate, then removed, and two identical objects were placed in the chamber. The mouse was returned to the chamber with the objects, placed facing directly away from them, recorded for 10 minutes and scored for time spent in proximity to each object (Bevins et al., "Object Recognition in Rats and Mice: A One-Trial Non-Matching-to-Sample Learning Task to Study 'Recognition Memory'," *Nat Protoc* 1:1306-1311 (2006), which is hereby incorporated by reference in its entirety). After one hour, the experiment was repeated, with one of the two objects replaced by a novel object. 4) Pre pulse inhibition. Each mouse was placed in a restraint chamber inside a larger isolation cabinet, equipped with sound, light, and air puff generators (SR-LAB, San Diego Instruments), and auditory PPI assessed as described (Geyer et al., "Measurement of Startle Response, Prepulse Inhibition, and Habituation," *Curr Protoc Neurosci*, Chapter 8, Unit 8, 7 (2001), which is hereby incorporated by reference in its entirety). 5) Sucrose preference. This experiment was always performed last, as mice were individually housed in order to measure liquid consumption. Sucrose preference was determined by the percentage of sucrose water consumed as a proportion of all water consumed (Willner et al., "Reduction of Sucrose Preference by Chronic Unpredictable Mild Stress, and its Restoration by a Tricyclic Antidepressant," *Psychopharmacology (Berl)* 93:358-364 (1987), which is hereby incorporated by reference in its entirety). Water is delivered in the colony by Hydropac (Lab Products, Inc.), so an additional Hydropac containing sucrose water was added to the cage and the two packs were weighed daily.

Activity and sleep assessment. Individually-housed mice were video recorded in 12"×12"×13.5" acrylic chambers, using infra-red cameras during the dark phase, for 72 continuous hours under 12/12 light/dark conditions. The distance traveled in meters per hour was calculated by Noldus Ethovision software, and averaged across 8 CTRL mice (gray fill, lines 22 and 17) and 10 SCZ mice (purple fill, line 52). In addition, transitions between phases of the light cycle (measured 30 minutes before and 30 minutes after light changes) were analyzed in terms of the number of consecutive seconds of immobility as a percentage of total immobility (AnyMaze, Stoelting), per 30 min measurement block as described (McShane et al., "Characterization of the Bout Durations of Sleep and Wakefulness," *J. Neurosci. Methods* 193:321-333 (2010); Pack et al., "Novel Method for High-Throughput Phenotyping of Sleep in Mice," *Physiol. Genomics* 28:232-238 (2007), which are hereby incorporated by reference in their entirety).

Statistical analysis. Unless otherwise noted, analyses were done in GraphPad Prism v.7. Individual tests were performed as noted for each experiment. All data are presented as mean±SEMs.

RNA-seq and bioinformatics. hGPCs assessed for gene expression were first sorted by fluorescence-activated cell sorting on the basis of the cell surface marker CD140a (BD Pharmingen) as described (FIG. 3) (Sim et al., "CD140a Identifies a Population of Highly Myelinogenic, Migration-Competent and Efficiently Engrafting Human Oligodendrocyte Progenitor Cells," *Nature Biotechnology* 29:934-941 (2011), which is hereby incorporated by reference in its entirety). Using polyA-selection, mRNA was isolated from these PDGFRα+ hGPCs, which were derived from iPSCs made from 4 patients with juvenile-onset schizophrenia (SCZ line numbers 8 [n=4 independent cell preparations], 29 [n=3], 51 [n=7], and 164 [n=8]); and 3 demographically similar healthy controls (CTR lines 22 [n=3], 37 [n=4], and 205 [n=7]). Sequencing libraries were prepared using the TruSeq RNA v2 kit, and sequenced on an Illumina HiSeq 2500 platform for approximately 45 million 1×100 bp reads per sample. The sequencing reads were pre-processed by trimming off adapter and low-quality sequences from the 3' end using Trimmomatic (Bolger et al., "Trimmomatic: A Flexible Trimmer for Illumina Sequence Data," *Bioinformatics* 30:2114-2120 (2014), which is hereby incorporated by reference in its entirety). The quality of reads before and after pre-processing was assessed with FastQC (D'Antonio et al., "RAP: RNA-Seq Analysis Pipeline, A New Cloud-Based NGS Web Application," *BMC Genomics* 16:S3 (2015), which is hereby incorporated by reference in its entirety), and the pre-processed reads were then aligned to the RefSeq NCBI reference human genome version GRCh38 (Pruitt et al., "NCBI Reference Sequences (RefSeq): A Curated Non-Redundant Sequence Database of Genomes, Transcripts and Proteins," *Nucleic Acids Research* 35:D61-65 (2007), which is hereby incorporated by reference in its entirety) with Subread read aligner (Liao et al., "The Subread Aligner: Fast, Accurate and Scalable Read Mapping by Seed-and-Vote," *Nucleic Acids Research* 41:e108 (2013), which is hereby incorporated by reference in its entirety) using Hamming distance to break ties between more than one optimal mapping locations. Raw gene counts were obtained from BAM alignment files with the featureCounts tool (Liao et al., "Feature Counts: An Efficient General Purpose Program for Assigning Sequence Reads to Genomic Features," *Bioinformatics* 30:923-930 (2014), which is hereby incorporated by reference in its entirety). After eliminating lowly expressed transcripts with a count <5 reads in more than 5 samples across the dataset, the count data was normalized using the RUVSeq (Risso et al., "Normalization of RNA-Seq Data Using Factor Analysis of Control Genes or Samples," *Nat Biotechnol* 32:896-902 (2014), which is hereby incorporated by reference in its entirety) R Bioconductor package (Gentleman et al., "Bioconductor: Open Software Development for Computational Biology and Bioinformatics," *Genome Biology* 5:R80 (2004), which is hereby incorporated by reference in its entirety) to account for variance. As described in the RUVSeq manual, the normalization was accomplished in the following three-step procedure: 1) in silico negative control genes were determined by first-pass differential expression analysis by the edgeR (Robinson et al., "EdgeR: A Bioconductor Package for Differential Expression Analysis of Digital Gene Expression Data," *Bioinformatics* 26:139-140 (2010), which is hereby incorporated by reference in its entirety) and DESeq2 (Love et al., "Moderated Estimation of Fold Change and Dispersion for RNA-Seq Data with DESeq2," *Genome Biology* 15:550 (2014), which is hereby incorporated by reference in its entirety) R Bioconductor packages, taking genes with FDR-adjusted P values >0.75, as calculated by both methods (approximately 7000 genes were unaffected by the condition of interest); 2) the negative control genes were then used in the RUVs function of the RUVSeq package, for calculation of variance factors; and, 3) the second-pass differential expression analysis (5% FDR and log 2 fold change >1) for determining disease-dysregulated genes was performed using the original counts, adjusting for RUVs-calculated variance factors by multi-factor GLM models implemented in the edgeR and DESeq2 packages.

This three-step analysis, with filtering for low-expressed transcripts, was used to compare each SCZ-derived hGPC cell line to the pooled CTR-derived hGPCs. The intersection of the resulting 4 individual lists of differentially expressed genes was taken as the conserved representative list of SCZ-dysregulated genes. In the normalization procedure for each comparison, the number of RUVs-calculated variance factors was limited to 1 for line 29, 3 for lines 8 and 164, and 7 for line 51, as determined by principal component and hierarchical clustering analyses performed with native R functions. To obtain average fold changes and P values for dysregulated genes in all 4 SCZ hGPC lines, a differential expression comparison of pooled SCZ to pooled CTR lines was performed by the same filtering and analysis workflow with the number of variance factors limited to 9.

For all differential expression comparisons, only the significant results that agreed between edgeR and DESeq2 methods were used in downstream analysis. Once individual fold changes and P values for dysregulated genes in all 4 SCZ hGPC lines were established relative to control lines, the differential expression of pooled SCZ to pooled CTR lines was performed. For each SCZ cell line, separate DE comparisons were performed against each control line and the intersection of the DE genes was taken as a representative list for that SCZ line against the control population. Fold changes and FDR-adjusted P values reported were calculated by edgeR. Functional annotation of the conserved set of SCZ-dysregulated genes was done using ToppCluster (Kaimal et al., "ToppCluster: A Multiple Gene List Feature Analyzer for Comparative Enrichment Clustering and Network-Based Dissection of Biological Systems," *Nucleic Acids Research* 38:W96-102 (2010), which is hereby incorporated by reference in its entirety) and Ingenuity Pathway Analysis (IPA). Network visualization and analysis of the results of functional annotation were performed in Gephi (Jacomy et al., "ForceAtlas2, A Continuous Graph Layout Algorithm for Handy Network Visualization Designed for the Gephi Software," *PloS one* 9:e98679 (2014), which is hereby incorporated by reference in its entirety) graph visualization software.

For streamlined execution of the above data processing and analysis routines, a set of Python and R scripts was developed. All genomic data have been deposited to GEO, accession number GSE86906.

Real-Time PCR. Expression levels in SCZ- and control derived GPCs of selected target genes identified by RNA-seq were assayed by TaqMan Low Density Array (TLDA)

Real-Time PCR. The raw data were analyzed in Espression-Suite Software version 1.1 supplied by Applied Biosystems and exported into HTqPCR R package (Chambers et al., "Highly Efficient Neural Conversion of Human ES and iPS cElls by Dual Inhibition of SMAD Signaling," *Nat Biotechnol* 27:275-280 (2009), which is hereby incorporated by reference in its entirety) for relative quantification analysis.

Example 1

Generation of iPSCs from Patients with Juvenile-Onset Schizophrenia

Patients with juvenile-onset schizophrenia, as well as healthy young adult controls free of known mental illness, were recruited and skin biopsies were obtained from each. Patient identifiers were not available to investigators besides the treating psychiatrist, although age, gender, race, diagnosis and medication history accompanied cell line identifiers. Fibroblasts were then isolated from each sample; from these, 11 new independent hiPS cell lines were derived from 8 patient samples (5 juvenile-onset schizophrenia patients and 3 healthy gender-matched and age-analogous controls (Table 1).

c-Myc (Takahashi et al., "Induction of Pluripotent Stem Cells from Adult Human Fibroblasts by Defined Factors," *Cell* 131:861-872 (2007); Welstead et al., "Generating iPS Cells from MEFS Through Forced Expression of Sox-2, Oct-4, c-Myc, and Klf4," *J Vis Exp* (2008), which are hereby incorporated by reference in their entirety). All lines were initially characterized and validated as pluripotent using global transcriptome profiling by RNA sequencing to assess pluripotent gene expression, as well as immunostaining for Oct4, Nanog, and SSEA4. The identity of each iPSC line was confirmed to match the parental donor fibroblasts using short tandem repeat (STR)-based DNA fingerprinting. iPSC line isolates were also karyotyped concurrently with these experiments to confirm genomic integrity. An additional well-characterized hiPSC control line, C27 (Chambers et al., "Highly Efficient Neural Conversion of Human ES and iPS Cells by Dual Inhibition of SMAD Signaling," *Nat Biotechnol* 27:275-280 (2009), which is hereby incorporated by reference in its entirety), was also used, to ensure that the control engraftment and differentiation data were consistent with prior studies (Wang et al., "Human iPSC-Derived Oligodendrocyte Progenitor Cells Can Myelinate and Rescue a Mouse Model of Congenital Hypomyelination," *Cell*

TABLE 1

| Subject number | hiPSC Line(s) | Age of subject | Gender | Ethnicity | RNA-Seq of CD140a+ GPCs | Anatomic assessment N = shiverer mice | Behavioral assessment N = myelin w/t mice |
|---|---|---|---|---|---|---|---|
| Control Subjects ||||||||
| Cntrl 1 | 19, 22 | 26 | M | C | √ | √ | √ |
| Cntrl 2 | 37 | 32 | F | AA | √ | √ | √ |
| Cntrl 3 | 205 | 25 | M | C | √ | √ | √ |
| Cntrl 4 | C27 | NA | NA | NA | √ | √ | |
| Schizophrenic Subjects ||||||||
| SCZ 1 | 8 | 10 | F | C | √ | √ | |
| SCZ 2 | 51, 52 | 16 | M | C | √ | √ | √ |
| SCZ 3 | 29, 31 | 12 | M | C | √ | | √ |
| SCZ 4 | 164 | 14 | F | AA | √ | √ | |
| SCZ 5 | 193 | 15 | F | NA | | √ | √ |

Patients and cell lines used in this study. A total of 11 new independent iPS cell lines were derived from 8 subjects; 5 juvenile-onset schizophrenic patients and 3 healthy controls; an established control line (C27) from an additional normal subject was published previously (Wang et al., "Human iPSC-Derived Oligodendrocyte Progenitor Cells can Myelinate and Rescue a Mouse Model of Congenital Hypomyelination," *Cell Stem Cell* 12:252-264 (2013); Chambers et al., "Highly Efficient Neural Conversion of Human ES and iPS cElls by Dual Inhibition of SMAD Signaling," *Nat Biotechnol* 27:275-280 (2009), which are hereby incorporated by reference in their entirety). hGPCs derived from these cells were assigned to individual experiments as noted. C, Caucasian; AA, African-American; NA, not available.

iPSC were generated using excisable foxed polycistronic hSTEMCCA lentivirus (Zou et al., "Establishment of Transgene-Free Induced Pluripotent Stem Cells Reprogrammed from Human Stem Cells of Apical Papilla for Neural Differentiation," *Stem Cell Res Ther* 3:43 (2012); Somers et al., "Generation of Transgene-Free Lung Disease-Specific Human Induced Pluripotent Stem Cells Using a Single Excisable Lentiviral Stem Cell Cassette," *Stem Cells* 28:1728-1740 (2010), which are hereby incorporated by reference in their entirety) encoding Oct4, Sox2, Klf4 and

*Stem Cell* 12:252-264 (2013), which is hereby incorporated by reference in its entirety). Altogether, hGPC preparations were evaluated from 7 iPSC lines derived from 5 SCZ patients, and 5 iPSC lines derived from 4 control subjects (Table 1). The iPSC cells were then instructed to GPC fate as previously described (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety), and after ≥105 days in vitro (DIV) under glial differentiation conditions, validated the predominant GPC phenotype of each cell population using flow cytometry for CD140a/PDGFαR (FIG. 2) (Sim et al., "CD140a Identifies a Population of Highly Myelinogenic, Migration-Competent and Efficiently Engrafting Human Oligodendrocyte Progenitor Cells," *Nature Biotechnology* 29:934-941 (2011), which is hereby incorporated by reference in its entirety). To optimize glial differentiation in vivo, transplants were limited to those preparations in which most cells were CD140a+ GPCs, with the remainder astroglial.

It was first asked whether SCZ hGPCs differed from wild-type hGPCs in myelination competence. To this end, SCZ hGPCs were implanted into neonatal immunodeficient shiverer mice (rag2$^{-/-}$×MBP$^{shi/shi}$), a congenitally hypomyelinated mutant lacking myelin basic protein (MBP) (Rosenbluth, J., "Central Myelin in the Mouse Mutant Shiverer," *J Comp Neurol* 194:639-648 (1980); Roach et al., "Characterization of Cloned cDNA Representing Rat Myelin Basic Protein: Absence of Expression in Brain of Shiverer Mutant Mice," *Cell* 34:799-806 (1983), which are hereby incorporated by reference in their entirety). As these otherwise myelin-deficient mice matured, their engrafted hGPCs differentiated into both astrocytes and myelinogenic oligodendrocytes yielding mice chimeric for individual patient-derived glia (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008); Windrem et al., "A Competitive Advantage by Neonatally Engrafted Human Glial Progenitors Yields Mice Whose Brains are Chimeric for Human Glia," *The Journal of Neuroscience: The Official Journal of the Society for Neuroscience* 34:16153-16161 (2014), which are hereby incorporated by reference in their entirety). By this means, mice with patient-specific, largely humanized forebrain white matter, derived from SCZ or control subjects were established (FIGS. 3A-3D).

Example 2

SCZ Glial Chimeric Mice were Uniformly Hypomyelinated

Figure 3E:
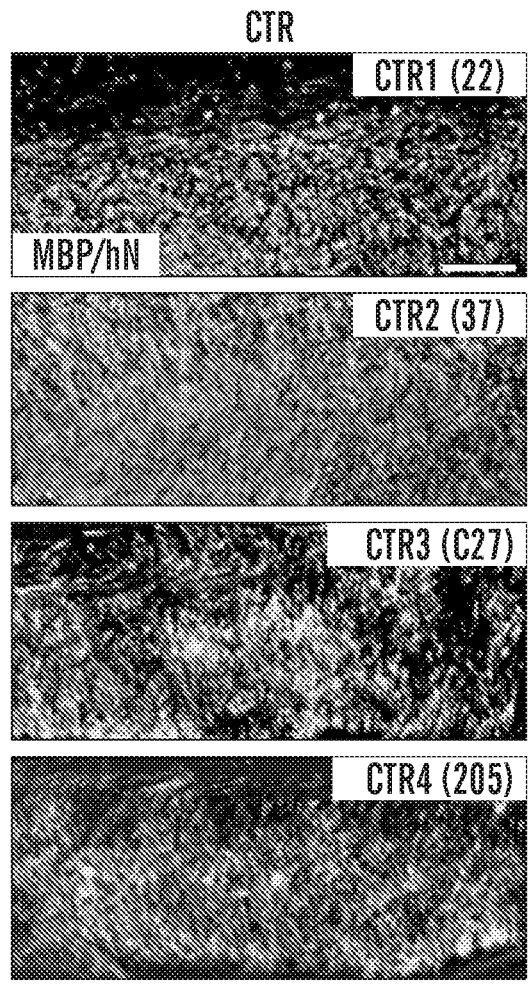
Figure 3F:
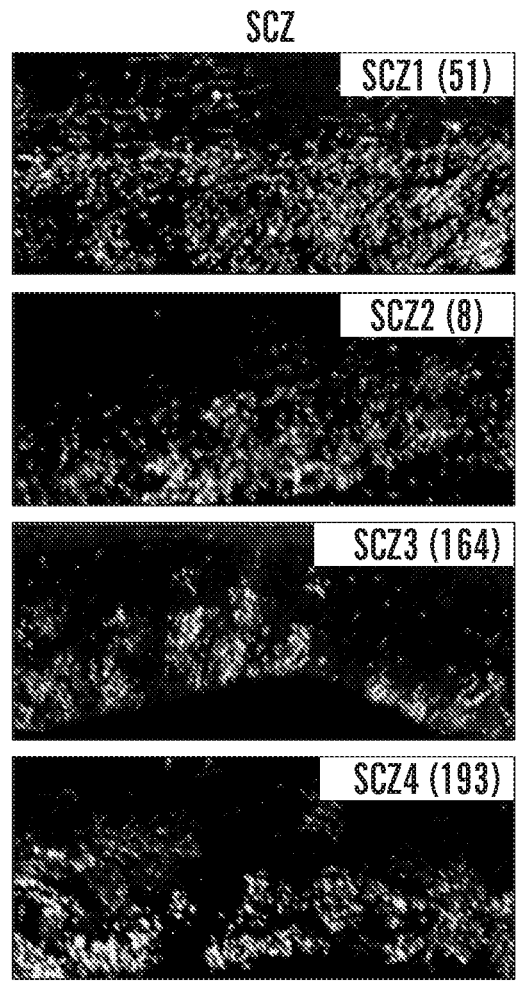
Figure 3G:
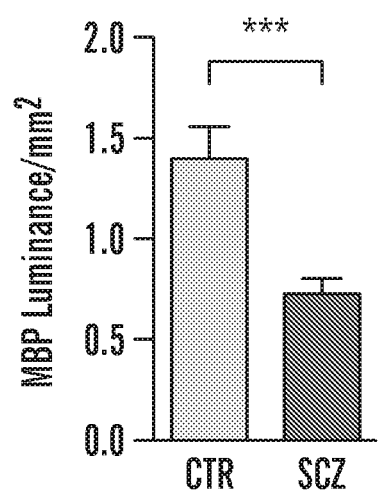
Figure 3H:
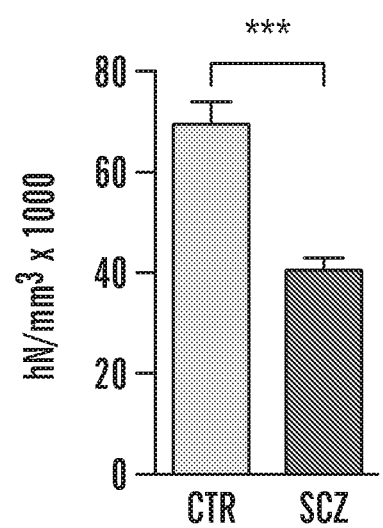
Figure 3I:
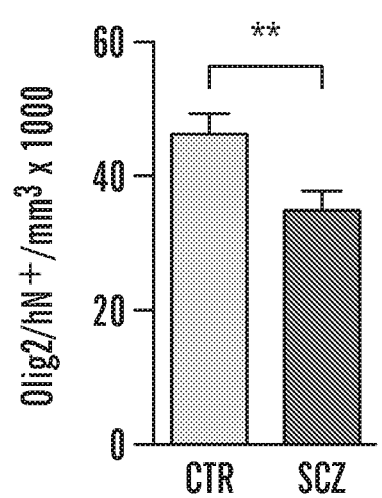
Figures 4A, 4B:
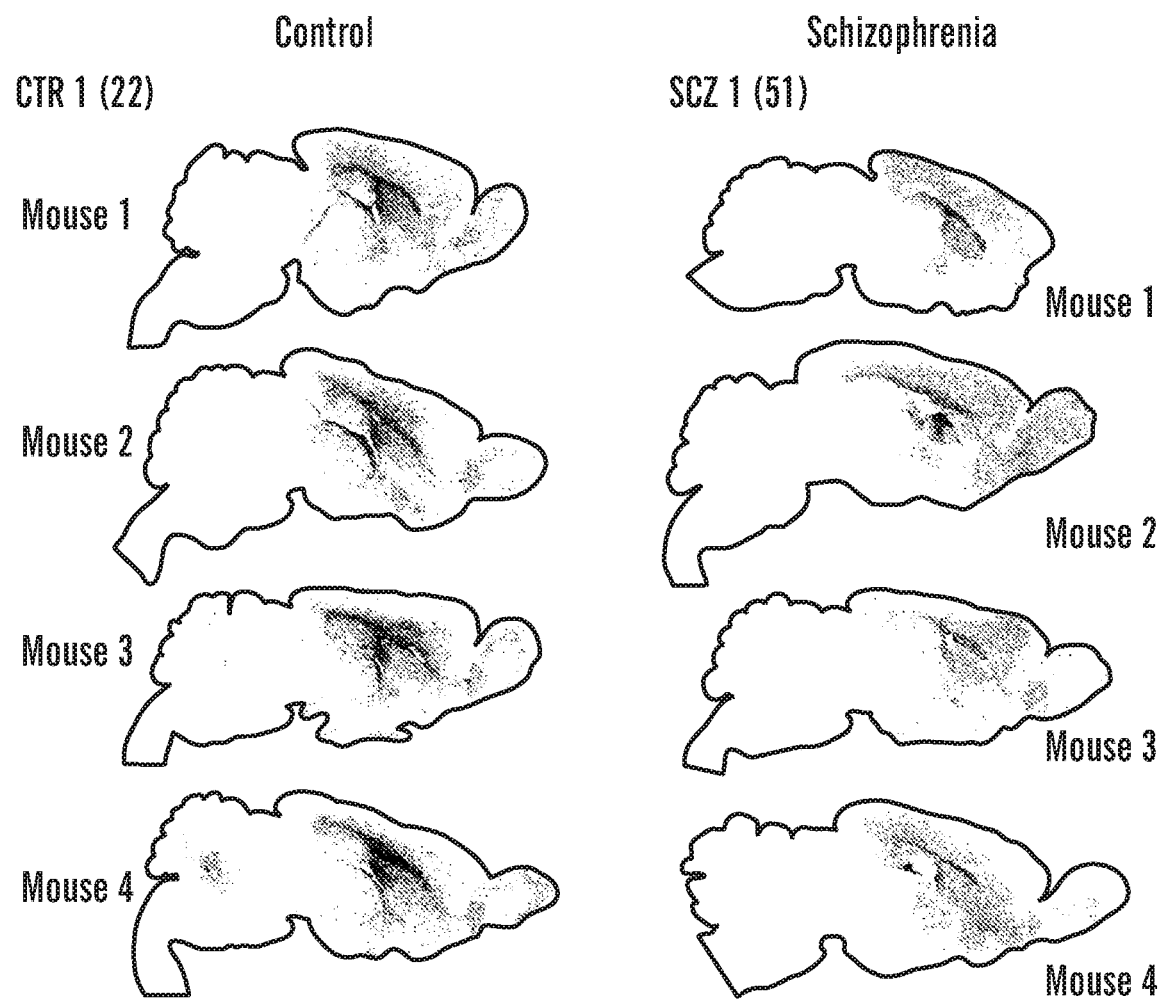
FIGS. 4A-4B show schizophrenia-derived GPCs exhibit aberrant dispersal in vivo. The dispersal patterns of GPCs produced from SCZ patients typically differed from that of iPSC hGPCs derived from normal patients, in that SCZ GPCs did not remain and expand within the white matter before progressing to cortical infiltration, as was otherwise invariably the case with normal GPCs.

It was first noted that the SCZ hGPCs manifested an aberrant pattern of migration upon neonatal transplantation. Normal control hGPCs invariably expanded through the white matter before colonizing the cortical gray matter (FIG. 3A), as was previously noted in both fetal tissue- and hiPSC GPC-engrafted shiverer mice (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008); Wang et al., "Human iPSC-Derived Oligodendrocyte Progenitor Cells Can Myelinate and Rescue a Mouse Model of Congenital Hypomyelination," *Cell Stem Cell* 12:252-264 (2013), which are hereby incorporated by reference in their entirety). In contrast, SCZ GPCs preferentially migrated earlier into the gray matter in shiverer mice, with large numbers traversing without stopping in the callosal white matter (n=4 lines from 4 different patients, each with >3 mice/patient, each vs. paired controls) (FIG. 3B and FIG. 4). This resulted in significantly fewer donor hGPCs in the white matter of shiverers engrafted with SCZ GPCs (FIGS. 3H-3I and FIG. 4). Importantly, this was associated with substantially diminished central myelination in these mice, as reflected by both MBP immunostaining (FIGS. 3C-3D and 3E-3F) and myelin luminance (FIG. 3G).

Figure 3J:
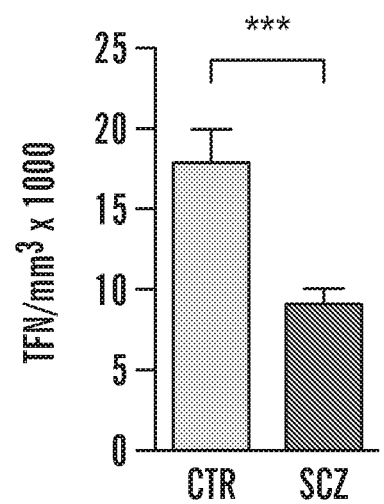

Since the SCZ hGPC-engrafted shiverers manifested deficient myelination, it was asked whether this was due to a relative failure of SCZ hGPCs to remain within white matter, or rather to a cell-intrinsic failure in myelinogenesis. Examining 19 wk-old SCZ and control hGPC-engrafted shiverer mice, significantly fewer human nuclear antigen (hNA)-defined donor-derived cells were found in SCZ hGPC-engrafted shiverer white matter (40,615±2,189×10³ hNA+ cells/mm3·n=18) than in mice identically transplanted with control hGPCs (69,970±4,091/mm³; n=32; p<0.0001 by 2-tailed t test (Fagerland et al., "Performance of five Two-Sample Location Tests For Skewed Distributions with Unequal Variances," *Contemp Clin Trials* 30:490-496 (2009); Merman, D. W., "A Note on Preliminary Tests of Equality of Variances," *Br J Math Stat Psychol* 57:173-181 (2004), which are hereby incorporated by reference in their entirety) (FIG. 3H). Moreover, the numbers of hNA+ donor cells co-expressing the oligodendroglial lineage marker Olig2 were similarly depressed in the SCZ hGPC-engrafted mice (33,619±2,435/mm³, n=26), relative to control hGPC-engrafted mice (46,139±2,858/mm³, n=17; p<0.002) (FIG. 3I). On that basis, it was next found that the density of transferrin-defined human oligodendroglia was similarly lower in the callosal white matter of SCZ hGPC chimeras, than in control hGPC chimeras (8,778±892.2/mm³, n=25; vs. 17,754±2,023/mm³, n=17, respectively; p=0.0006, Mann-Whitney) (FIG. 3J). These data indicate that SCZ GPCs are deficient not only in their colonization of the forebrain white matter, but also in their oligodendrocytic differentiation, with a resultant suppression of central myelinogenesis. Together, these findings suggest that SCZ hGPCs migrate aberrantly, traversing rather than homing to developing white matter, thus yielding relatively poor white matter engraftment, deficient myelin formation, and premature cortical entry relative to normal GPCs.

Example 3

Figure 5A:
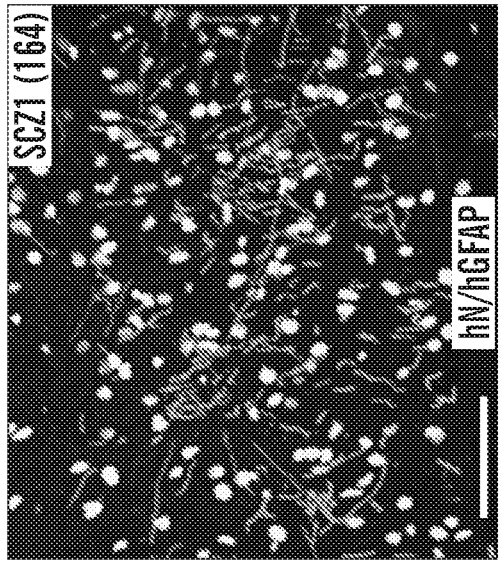
FIG. 5A-5J show astrocytic differentiation is impaired in schizophrenia hGPC chimeric brain. Human iPSC GPC chimeras were established in immunodeficient shiverer hosts and sacrificed at 19 weeks, for astrocytic differentiation assessment.
Figure 5B:
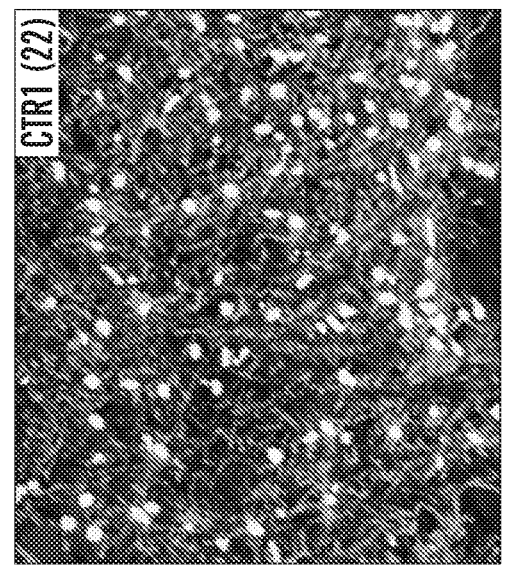
Figure 5C:
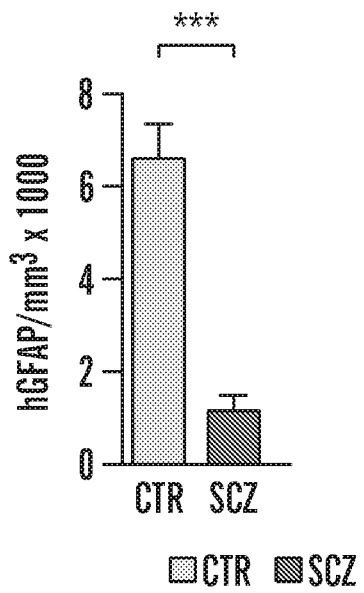
Figure 5D:
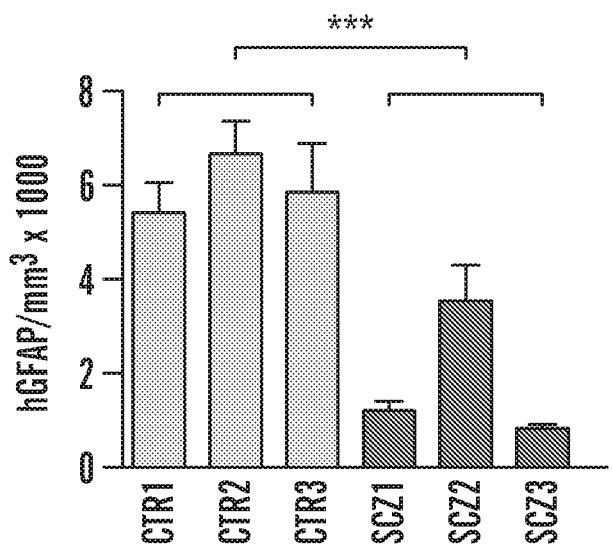
Figure 5E:
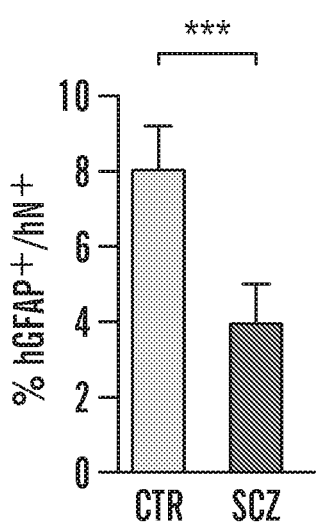
Figure 5F:
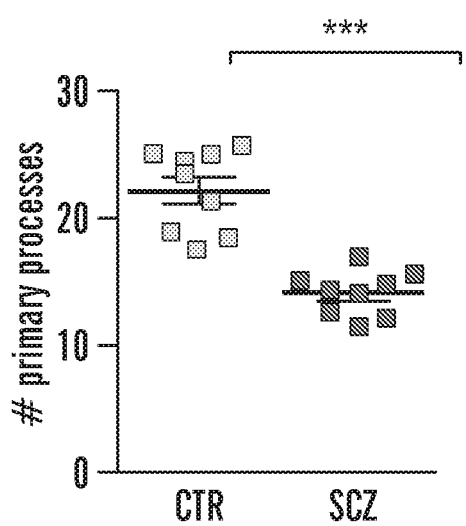
Figure 5I:
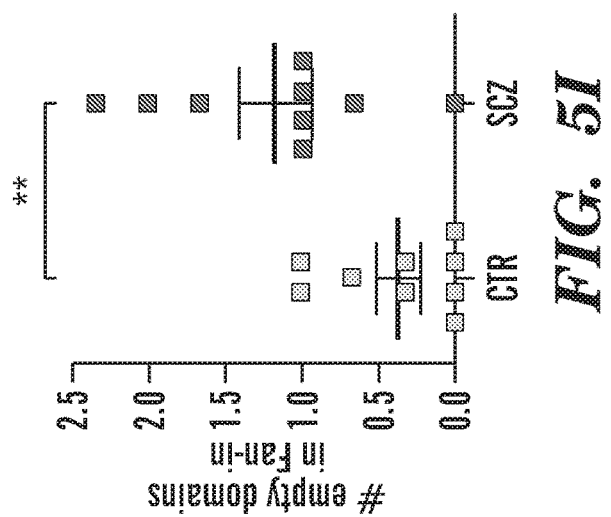
Figure 5H:
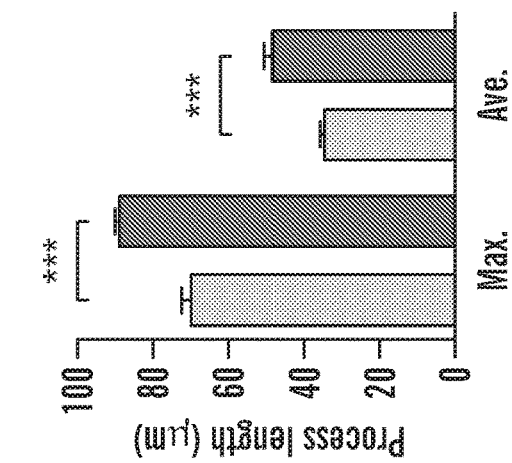
Figure 5G:
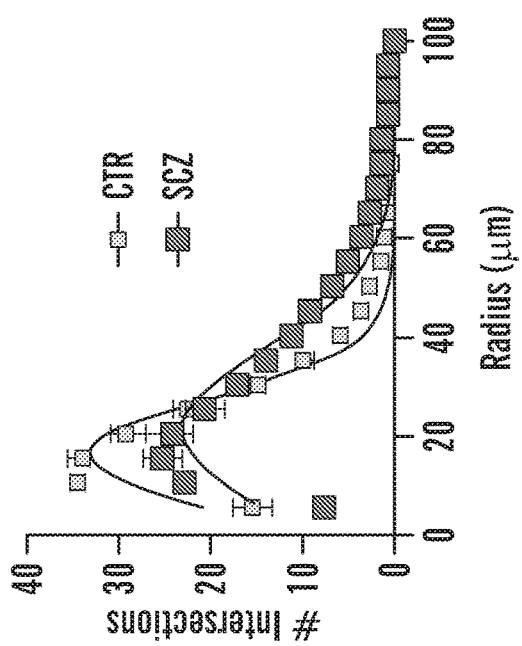
Figure 5J:
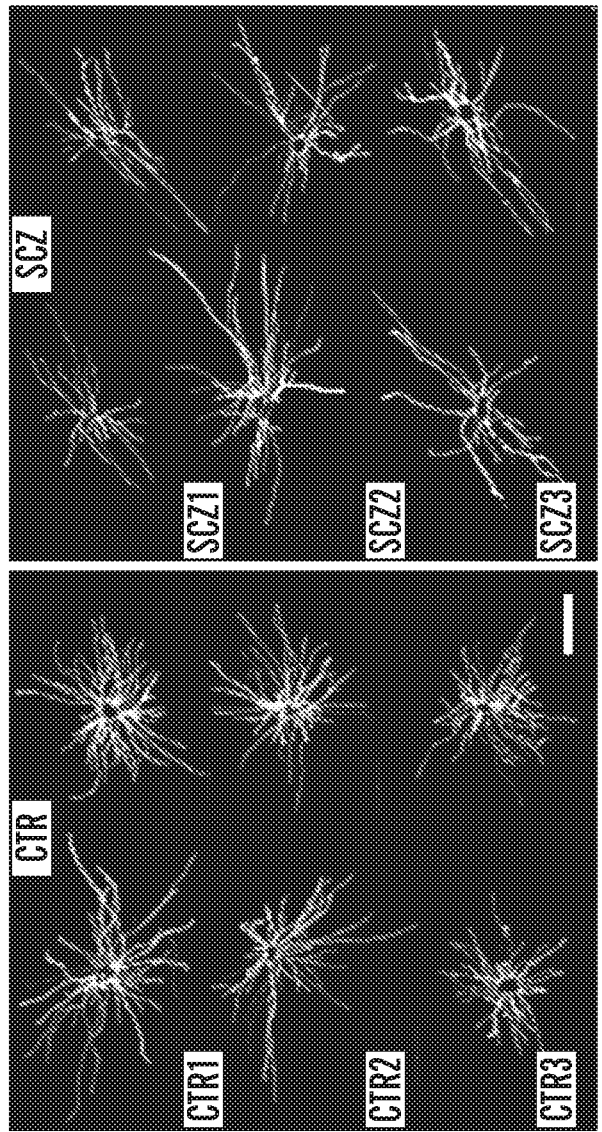

SCZ Glial Chimeric Mice Manifested Developmentally-Delayed Astrocytic Maturation It was next asked whether the SCZ hGPCs that prematurely entered the gray matter differentiated instead into astrocytes in that environment, or whether they rather manifested an impairment in lineage progression that prevented their astrocytic differentiation as well. Both SCZ and control hGPC-engrafted shiverer brains were immunostained for astrocytic glial fibrillary acidic protein (GFAP) at 19 weeks after neonatal graft, using a species-specific anti-human GFAP antibody. It was found that astrocytic maturation from engrafted hGPCs was markedly deficient in the SCZ hGPC-engrafted brains (n=19, derived from 3 SCZ patient lines, and n=12 control mice, from 3 control patients) (FIGS. 5A-5B). In the callosal white matter, as well as in both the striatal and cortical gray matter, astrocytic differentiation by SCZ hGPCs was significantly less than that of control GPCs, such that whereas all control hGPC forebrains showed dense human GFAP+ astrocytic maturation, far fewer SCZ hGPCs manifested hGFAP expression and astrocytic phenotype (controls: 6,616±672.3 GFAP+ cells/mm³ in callosum, n=12; SCZ: 1,177±276.6 GFAP+ callosal cells/mm³, n=19; p<0.0001 by 2-way t-test (FIG. 5C). This defect in astrocytic differentiation was consistently observed in all mice (n=19) derived from the 3 SCZ patients assessed, compared to the control GPC-engrafted mice (n=12) derived from 3 normal subjects (FIG. 5D), and reflected in part the lower proportion of GFAP+ astrocytes that developed among engrafted human cells in the SCZ HGPC-engrafted brains (FIG. 5E). Furthermore, Sholl analysis of individual astroglial morphologies (Sholl, D. A., "Dendritic Organization in the Neurons of the Visual and Motor Cortices of the Cat," *J. Anat.* 87:387-406 (1953), which is hereby incorporated by reference in its entirety), as imaged in 150 μm sections and reconstructed in Neurolucida (FIG. 5J), revealed that astrocytes in SCZ hGPC chimeras differed significantly from their control hGPC-derived counterparts, with fewer primary processes (FIG. 5F), less proximal branching (FIG. 5G), longer distal fibers (FIG. 5H), and less coherent domain structure (FIG. 5I). Thus, SCZ hGPCs derived from multiple patients exhibited a common defect in phenotypic maturation, and hence proved deficient in astrocytic differentiation as well as myelination.

Example 4

Figure 6A:
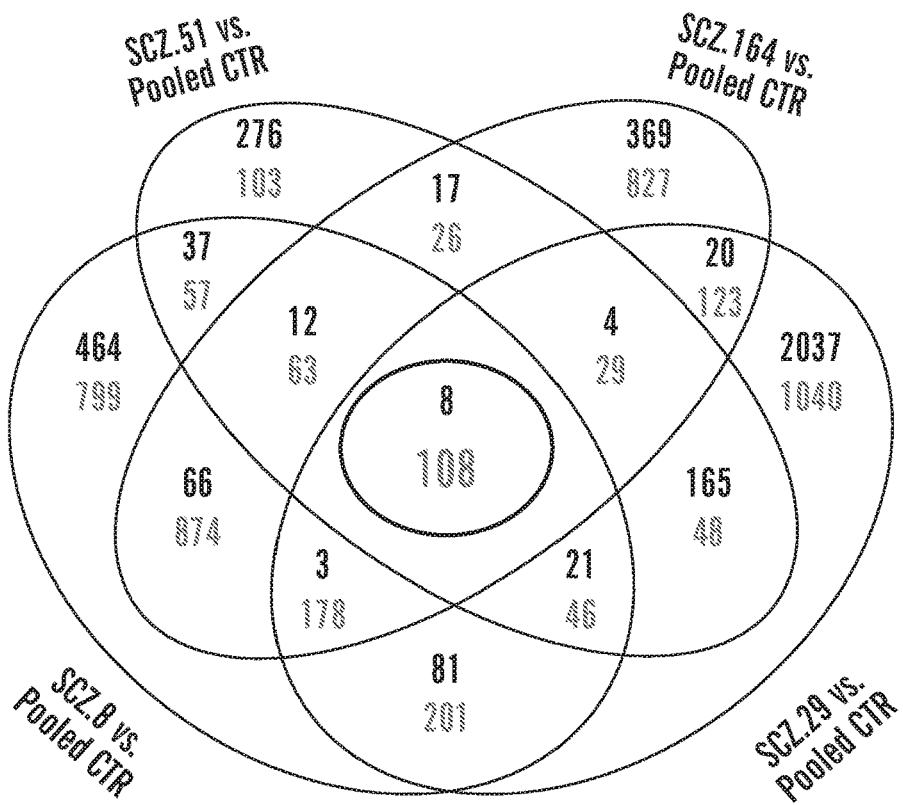
Figure 6B:
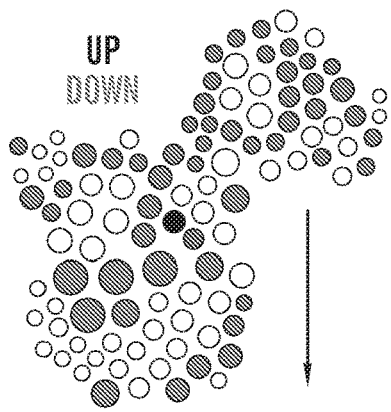
Figure 6B:
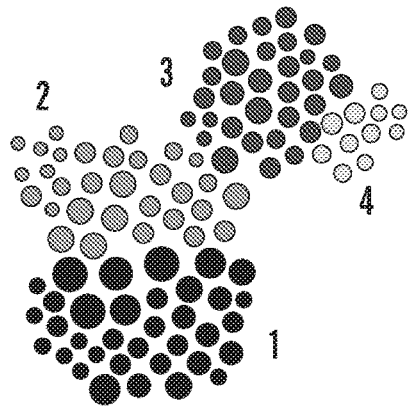
Figure 6D:
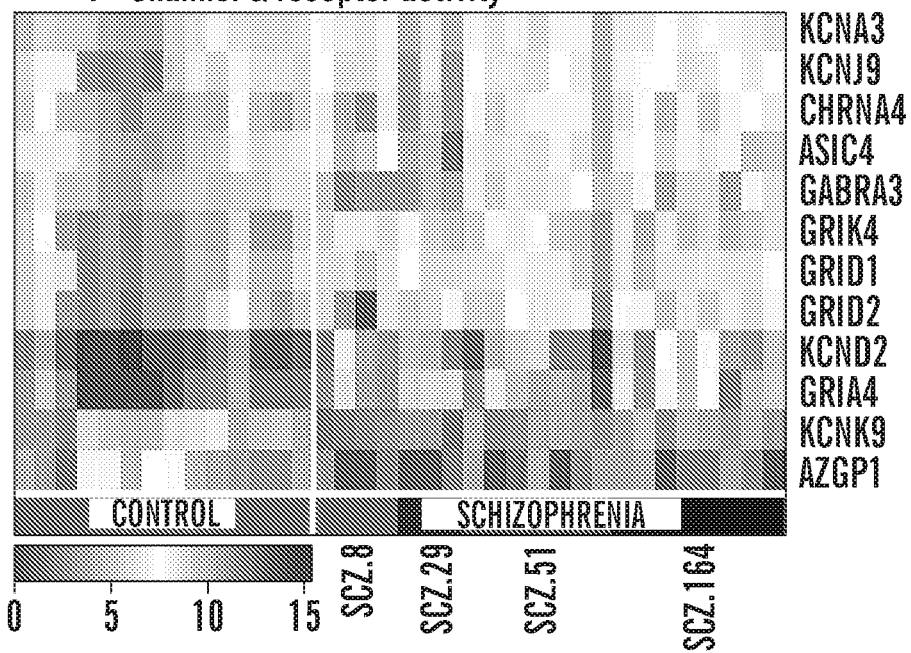
Figure 6E:
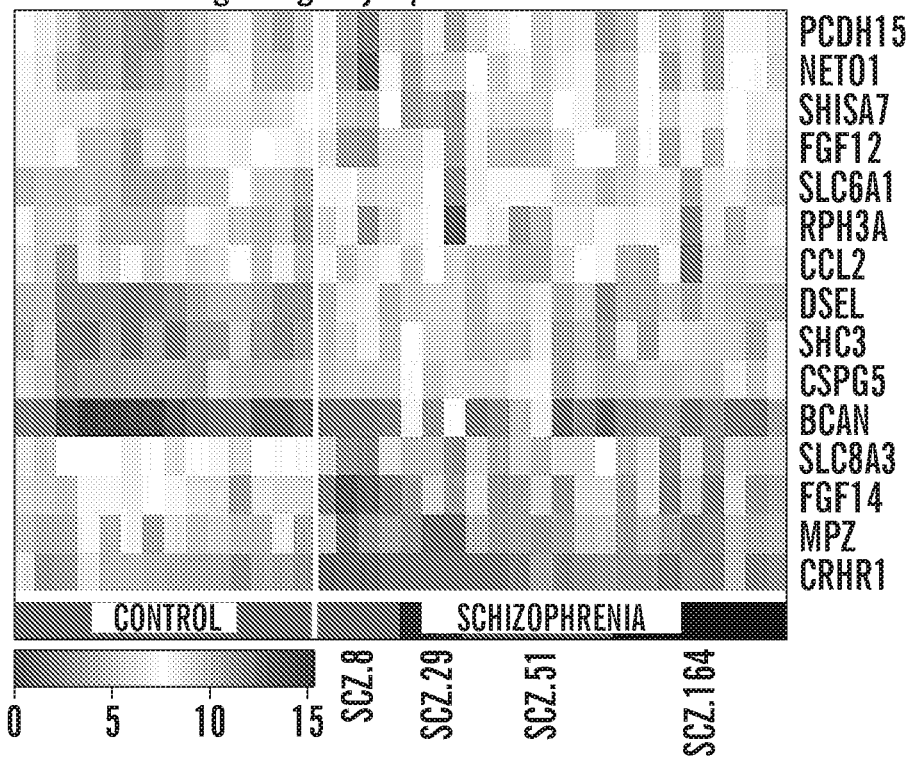
Figure 6F:
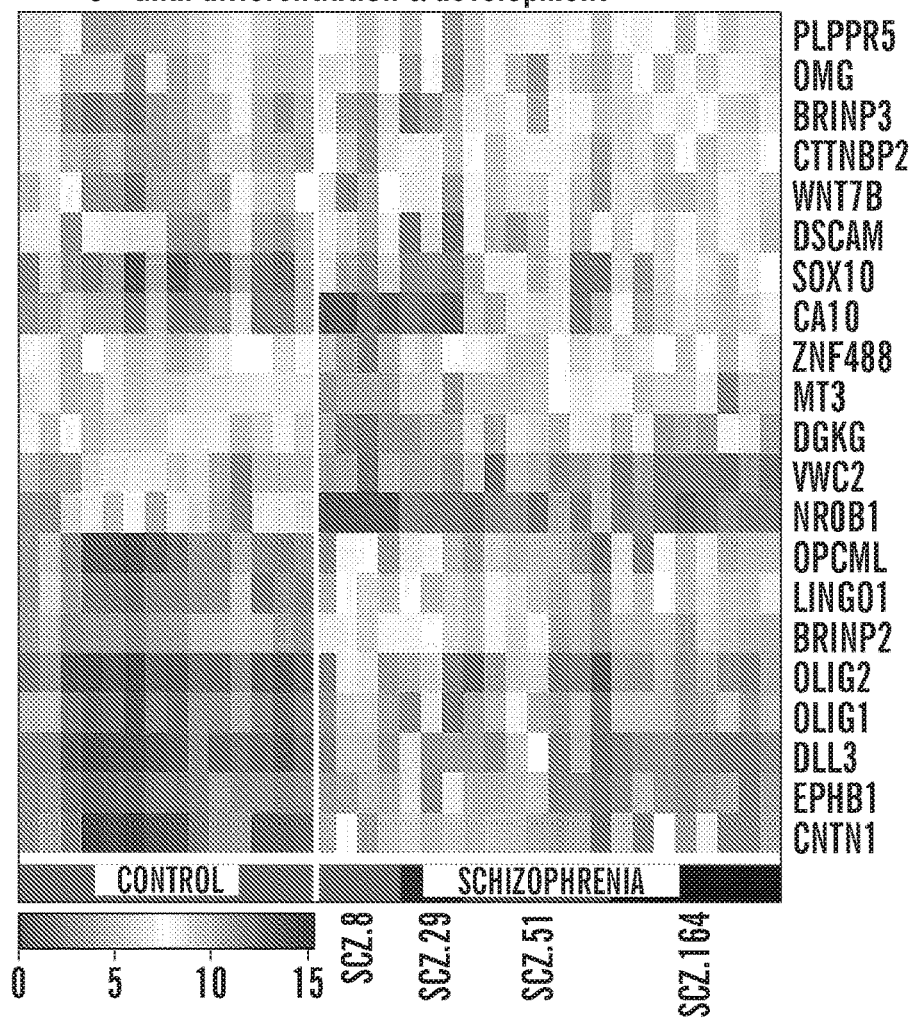
Figure 6G:
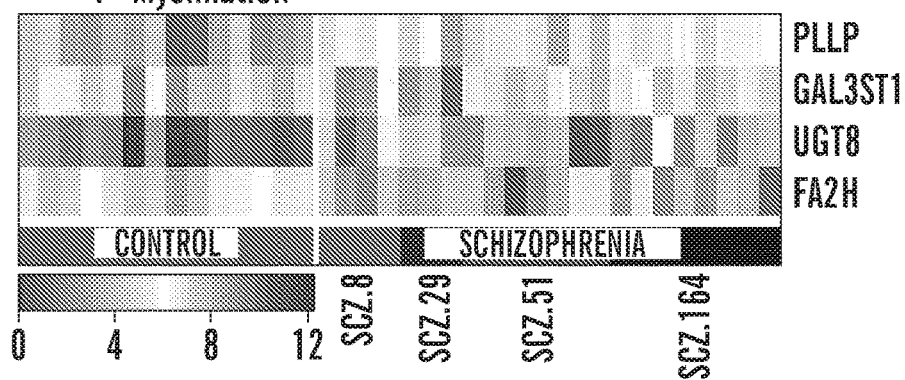
Figure 7A:
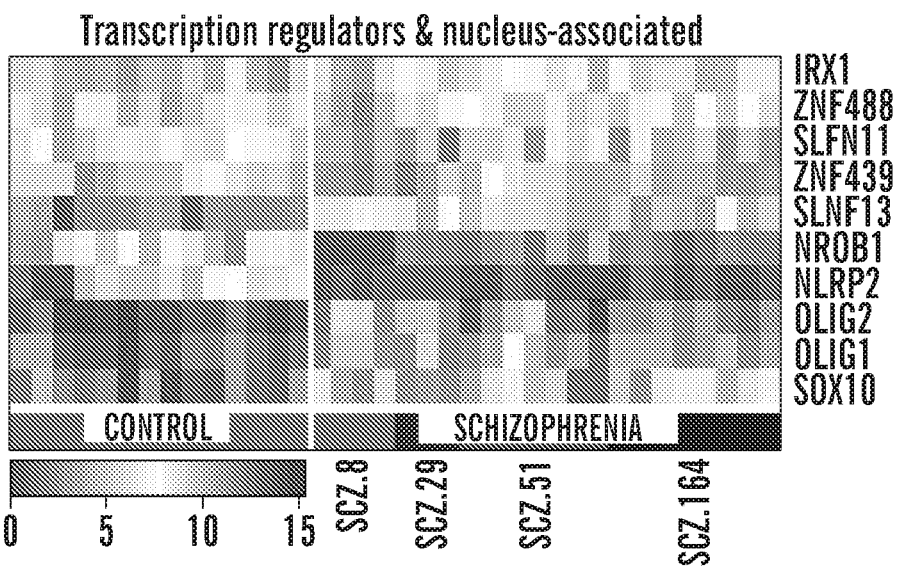
FIGS. 7A-7R show heat maps of significantly dysregulated genes in schizophrenic relative to control hiPSC GPCs. Expression patterns for shared genes differentially expressed by hiPSC GPCs derived from 4 schizophrenic patients, relative to the pooled gene expression pattern of hGPCs derived from 3 control-derived iPSCs (log 2 fold change >1.0, FDR 5%, 118 genes total) are shown. The dysregulated genes were manually annotated and grouped into relevant sets based on their function and cellular localization. Each heat map visualizes UQ-normalized, log 2-transformed counts of genes grouped into the following functional categories, comprising genes encoding.
Figure 7B:
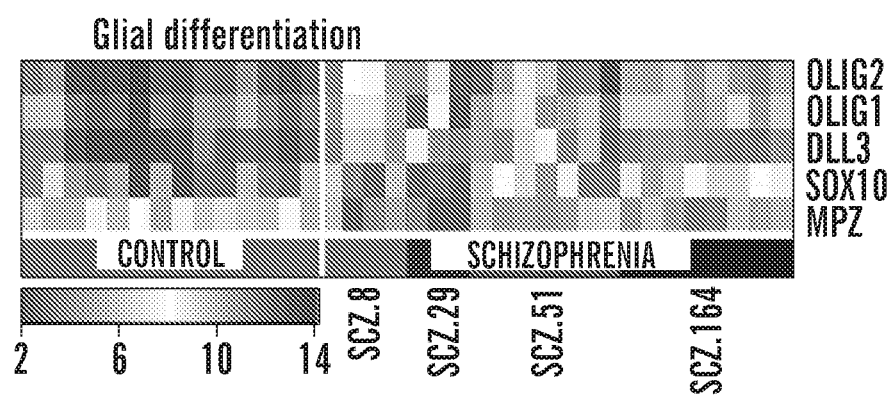
(FIG. 7B) glial differentiation-associated proteins.
Figure 7C:
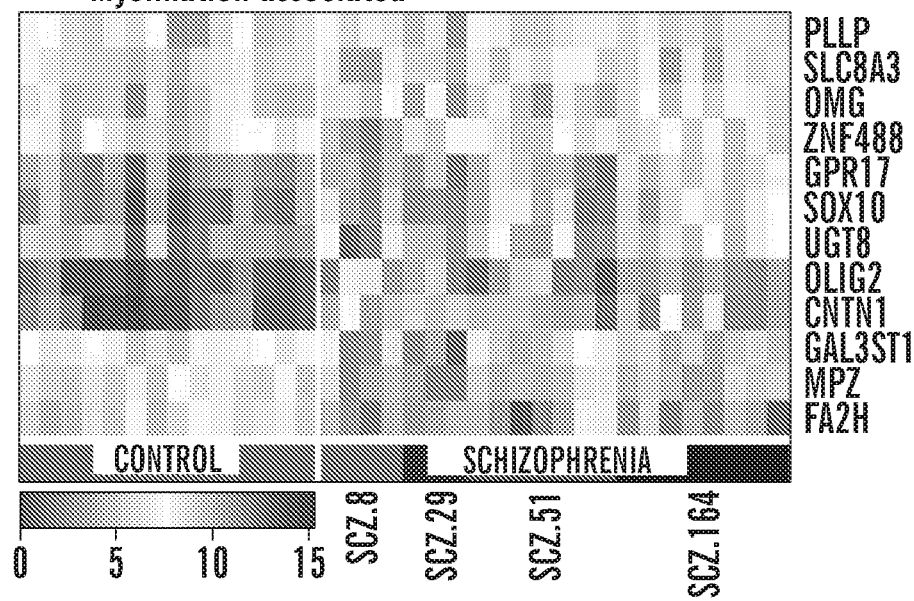
(FIG. 7C) myelin-related genes and transcription factors.
Figure 7D:
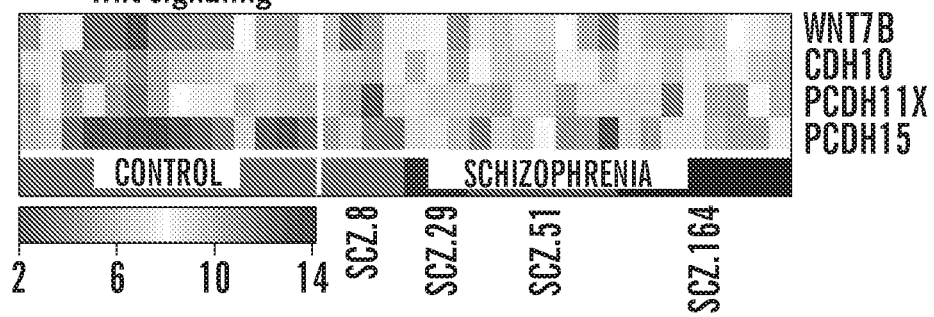
(FIG. 7D) Wnt pathway effectors.
Figure 7E:
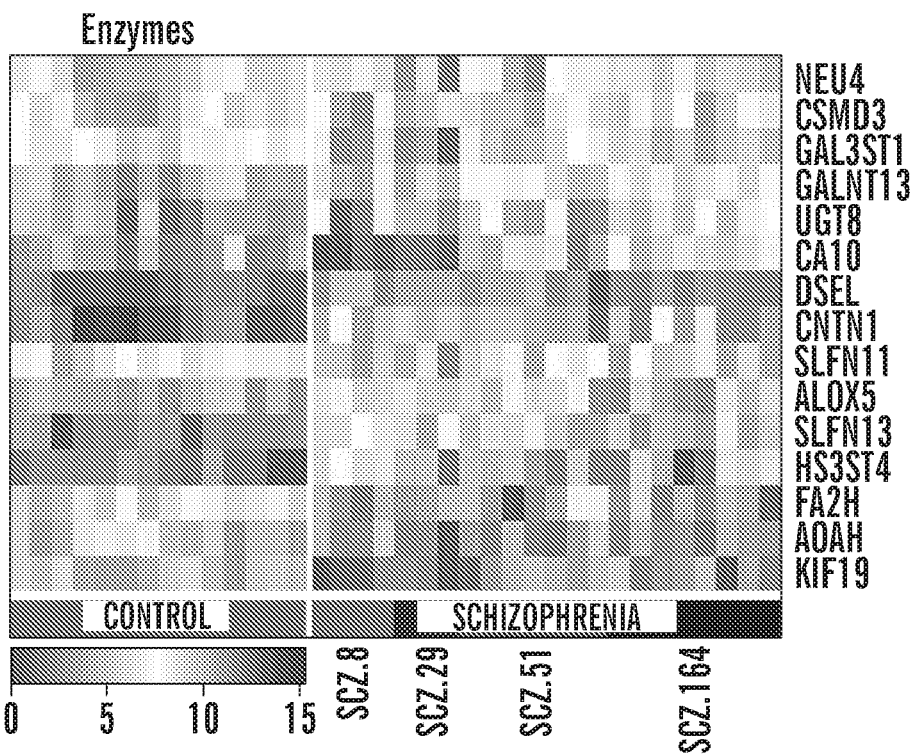
(FIG. 7E) metabolic enzymes.
Figure 7F:
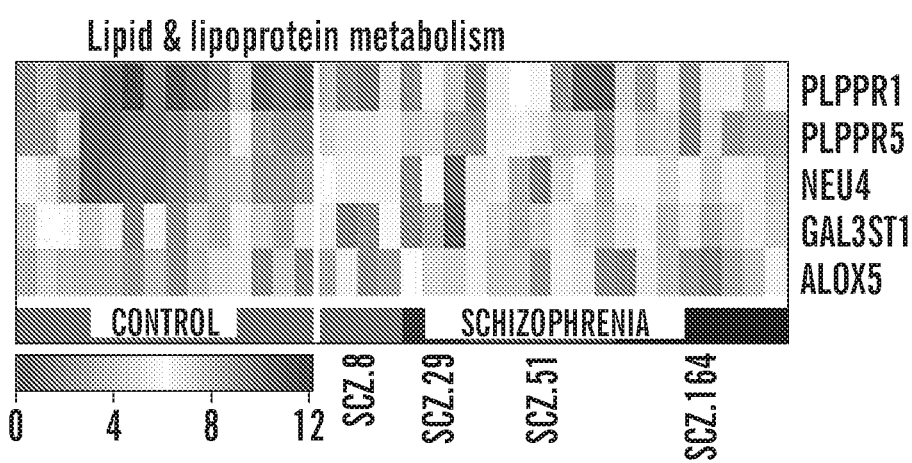
(FIG. 7F) lipid and lipoprotein metabolism.
Figure 7G:
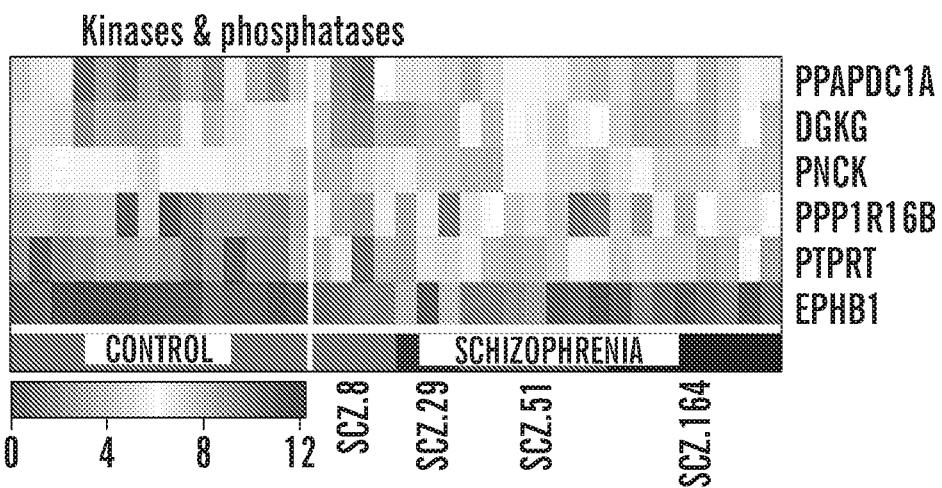
(FIG. 7G) kinases and phosphatases.
Figure 7H:
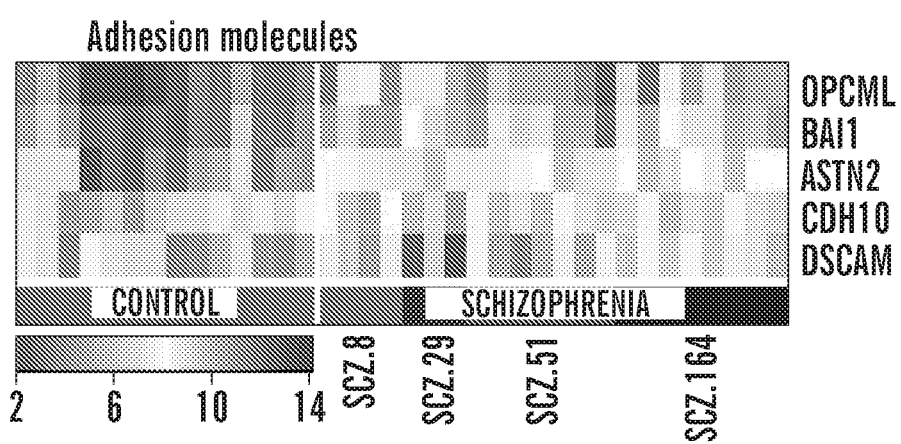
(FIG. 7H) adhesion molecules, cadherins, and astrotactins.
Figure 7I:
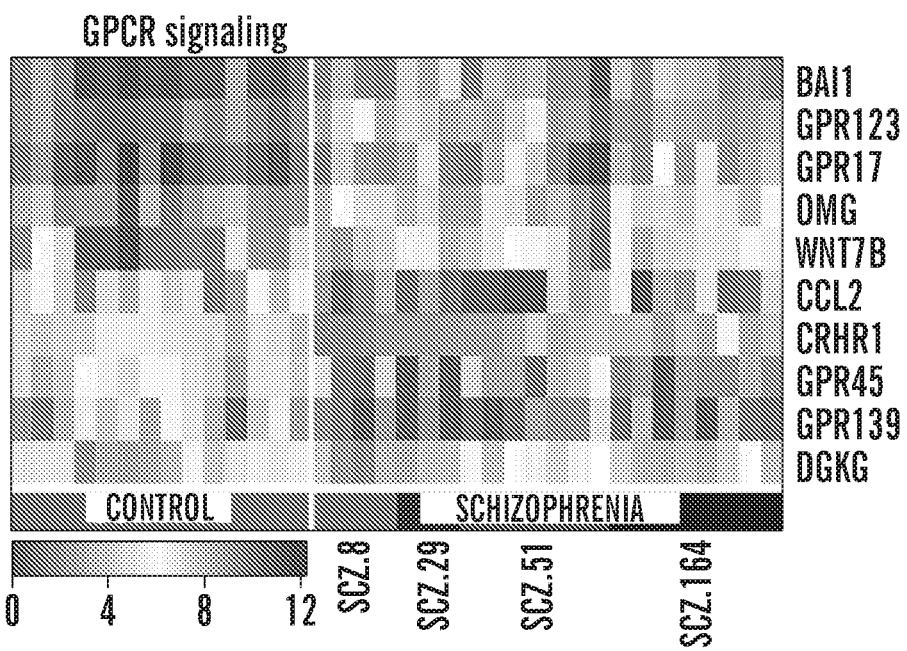
(FIG. 7I) GPCR signal intermediates.
Figure 7J:
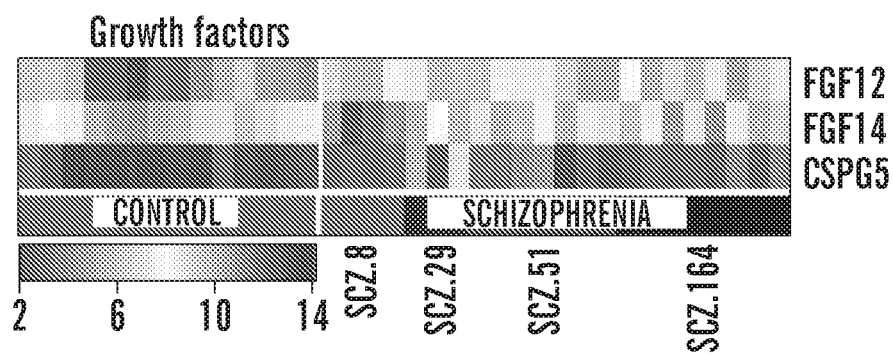
(FIG. 7J) growth factors.
Figure 7K:
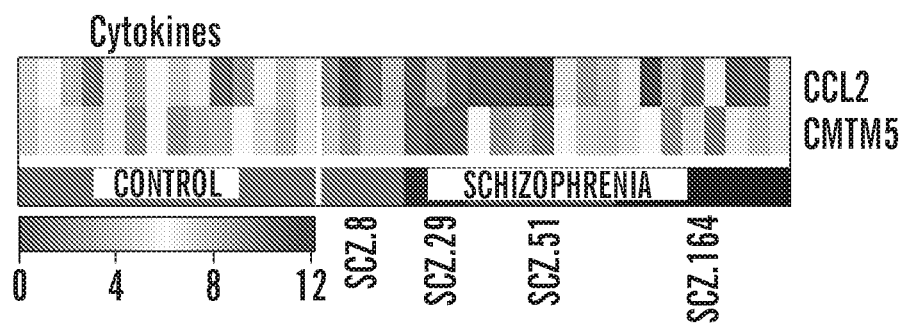
(FIG. 7K) cytokines.
Figure 7L:
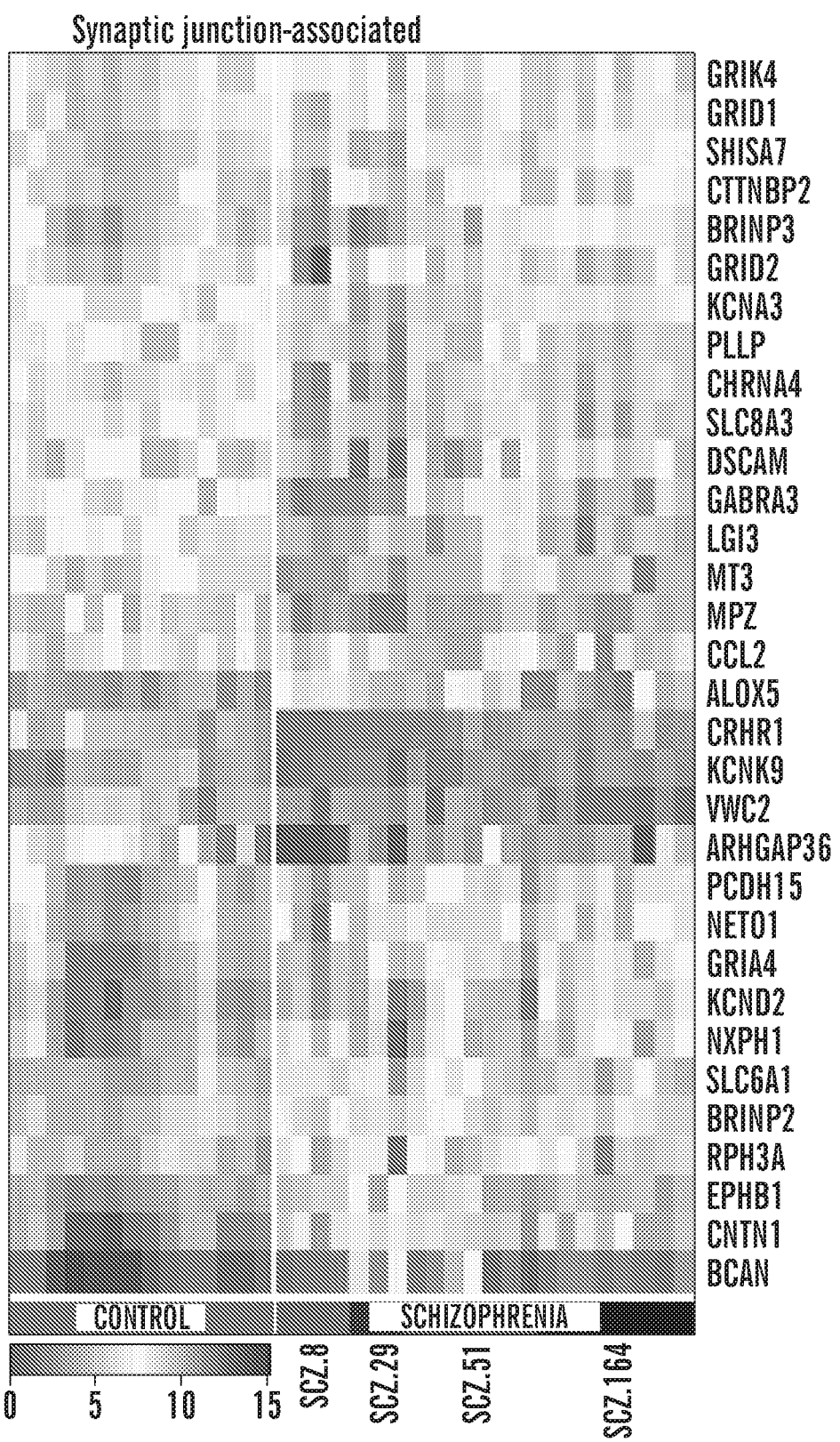
(FIG. 7L) cell signaling and synaptic proteins.
Figure 7M:
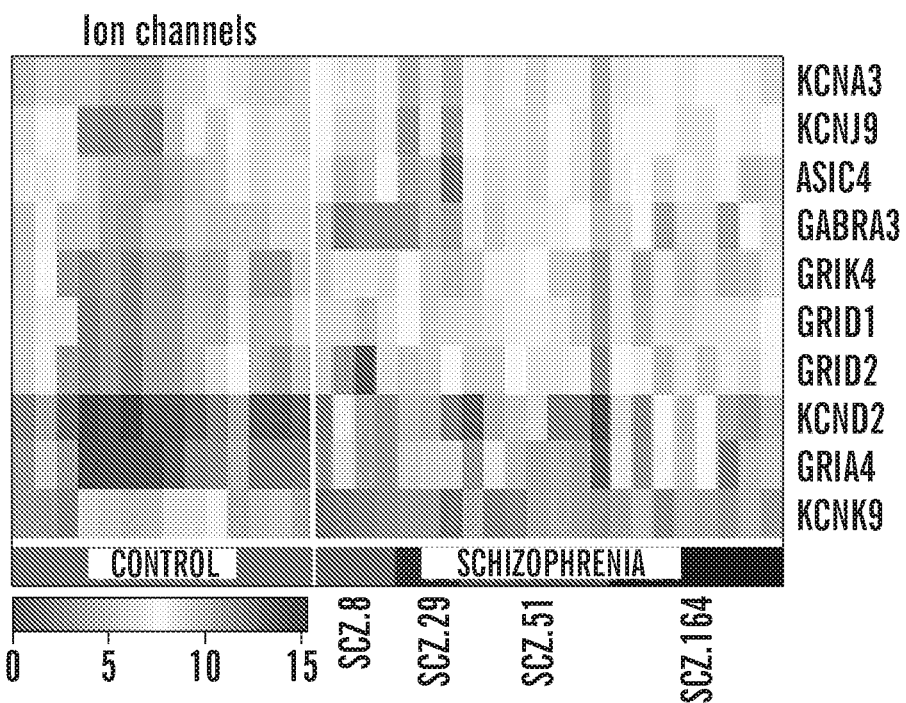
(FIG. 7M) ion channels.
Figure 7N:
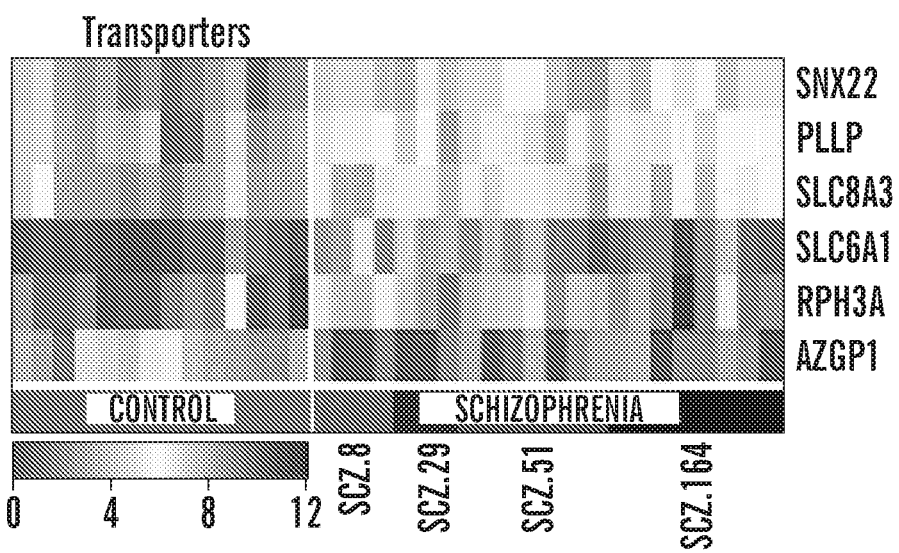
(FIG. 7N) transporters.
Figure 7O:
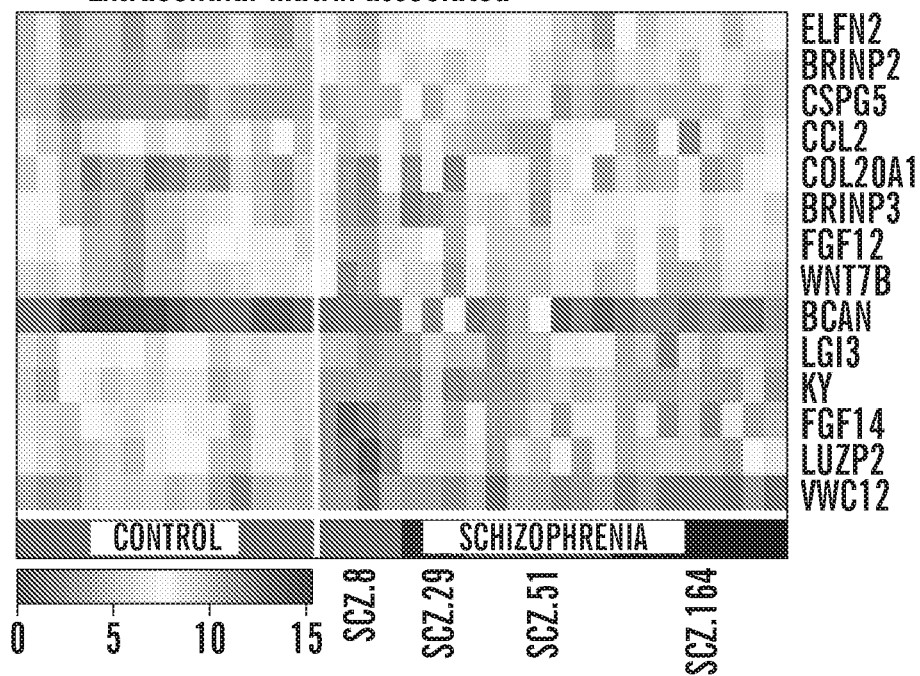
(FIG. 7O) extracellular matrix constituents.
Figure 7P:
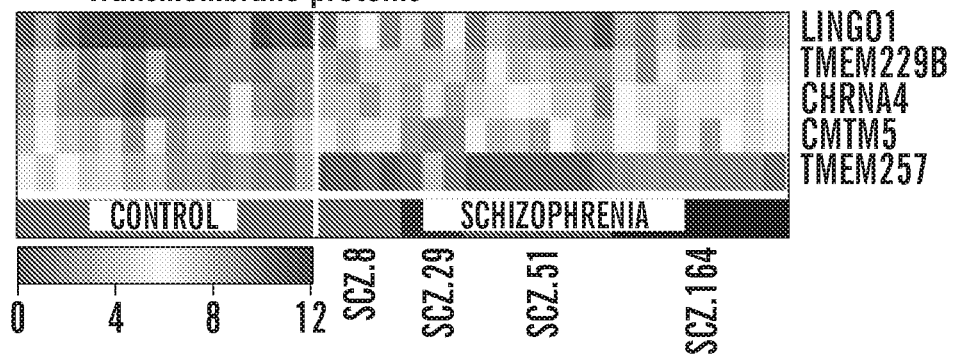
(FIG. 7P) other transmembrane proteins.
Figure 7Q:
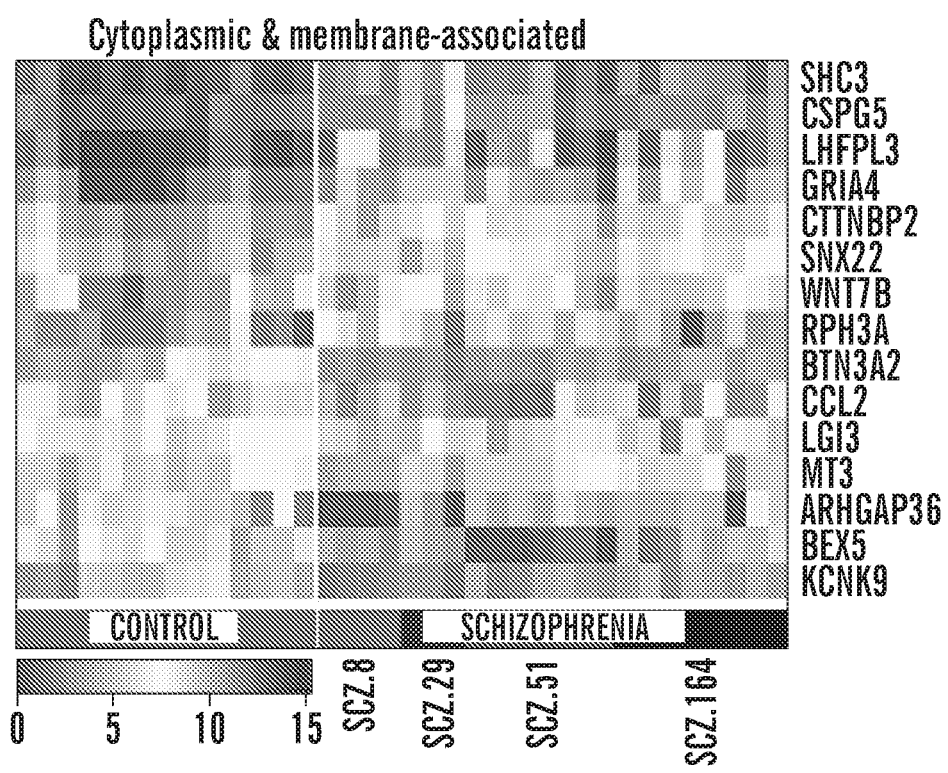
(FIG. 7Q) other cytoplasmic and membrane-bound proteins.
Figure 7R:
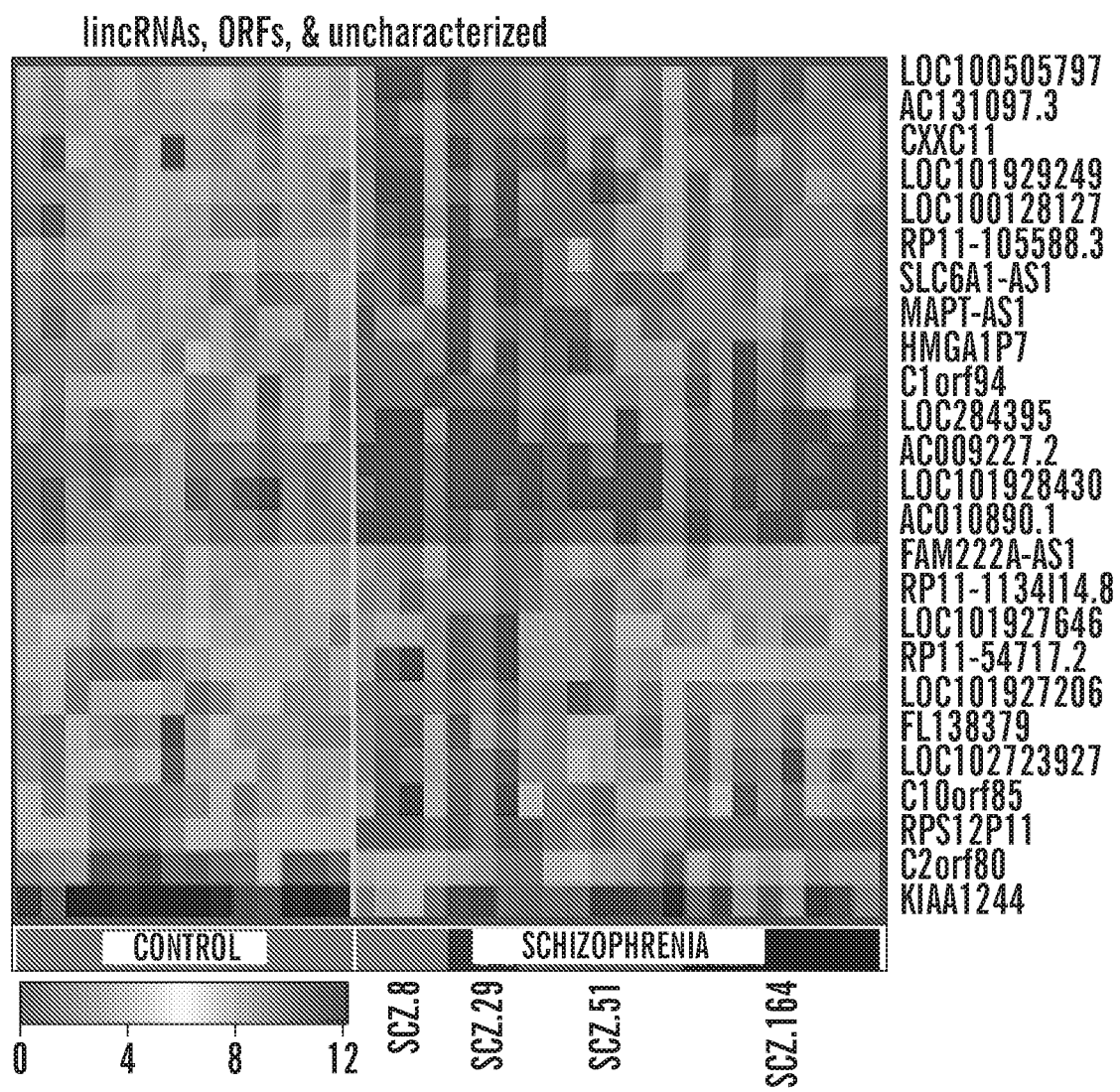

SCZ hGPCs Showed Cell-Autonomous Misexpression of Differentiation-Associated Genes To better define the molecular basis for the apparent impediment to terminal glial differentiation in SCZ GPC-engrafted mice, and to define which aspects of that deficit might be cell-autonomous, RNA-seq analysis was used to identify the differentially expressed genes of SCZ iPSC-derived GPCs, relative to those of control-derived glia. Sequencing data was used to reconstruct the transcriptional patterns of hGPCs derived from 4 different SCZ and 3 control patients. hGPCs were derived at time points ranging from 154 to 242 days in vitro, and sorted for hGPCs using CD140a-targeted FACS. Using a 5% FDR and a fold-change threshold of 2, a total of 118 mRNAs were identified that were differentially expressed by CD140a-sorted SCZ hGPCs relative to their control iPSC hGPCs (FIGS. 6A-6B). Among those genes most differentially expressed by CD140a-sorted SCZ hGPCs were a host of glial differentiation-associated genes, in particular those associated with early oligodendroglial and astroglial lineage progression, which were uniformly down-regulated in the SCZ hGPCs relative to their normal controls (FIGS. 6C and 6F). These included a coherent set of the key GPC lineage transcription factors OLIG1, OLIG2, SOX10, and ZNF488, as well as genes encoding stage-regulated proteins involved in myelination such as GPR17, UGT8, OMG, and FA2H (FIG. 6G; see Table 2 and FIG. 7 for detailed gene expression data).

TABLE 2

Significantly dysregulated genes in SCZ-derived relative to control-derivedOPCs
Table 2. Significantly dysregulated genes in SCZ relative to control GPCs. These tables list shared genes differentially expressed by hiPSC GPCs derived from 4 schizophrenic patients, relative to the pooled gene expression pattern of hGPCs derived from 3 control-derived iPSCs (log2 fold change > 1.0, FDR 5%, 116 genes total, red, upregulated in SCZ vs CTRL; green, downregulated in SCZ GPCs; color intensity proportionate to differential dysregulation). The fold-changes (FC) and FDR-adjusted p values shown here were derived from the comparison of the pooled schizophrenia-derived GPC cell lines to the pooled control-derived GPC lines. The dysregulated genes were grouped into functional sets according to their cellular roles and localizations.

| Gene ID | Log2 FC | P Value | Entrez Gene Name |
|---|---|---|---|
| Transcription regulators, & nucleus-associated (10 genes) | | | |
| SLFN13 | 2.832 | 2.18E−13 | schlafen family member 13 |
| SLFN11 | 2.193 | 6.47E−09 | schlafen family member 11 |
| NLRP2 | −7.208 | 4.24E−58 | NLR family, pyrin domain containing 2 |
| SOX10 | −4.448 | 8.37E−19 | SRY-box 10 |
| NR0B1 | −3.321 | 5.92E−27 | nuclear receptor subfamily 0 group B member 1 |
| OLIG2 | −3.196 | 4.23E−19 | oligodendrocyte lineage transcription factor 2 |
| OLIG1 | −3.146 | 5.72E−22 | oligodendrocyte transcription factor 1 |
| ZNF439 | −2.139 | 6.14E−08 | zinc finger protein 439 |
| IRX1 | −1.815 | 5.52E−06 | iroquois homeobox 1 |
| ZNF488 | −1.464 | 4.44E−07 | zinc finger protein 488 |
| Glial differentiation (5 genes) | | | |
| SOX10 | −4.448 | 8.37E−19 | SRY-box 10 |
| OLIG2 | −3.196 | 4.23E−19 | oligodendrocyte lineage transcription factor 2 |
| OLIG1 | −3.146 | 5.72E−22 | oligodendrocyte transcription factor 1 |
| DLL3 | −2.352 | 2.09E−24 | delta-like 3 (Drosophila) |
| MPZ | −2.105 | 7.66E−13 | myelin protein zero |
| Myelination-associated (12 genes) | | | |
| SOX10 | −4.448 | 8.37E−19 | SRY-box 10 |
| GPR17 | −3.357 | 1.94E−10 | G protein-coupled receptor 17 |
| UGT8 | −3.250 | 4.36E−09 | UDP glycosyltransferase 8 |
| OLIG2 | −3.196 | 4.23E−19 | oligodendrocyte lineage transcription factor 2 |
| GAL3ST1 | −2.681 | 4.01E−12 | galactose-3-O-sulfotransferase 1 |
| CNTN1 | −2.675 | 5.65E−15 | contactin 1 |
| PLLP | −2.581 | 1.21E−24 | plasmolipin |
| OMG | −2.561 | 5.09E−12 | oligodendrocyte myelin glycoprotein |
| FA2H | −2.440 | 4.45E−08 | fatty acid 2-hydroxylase |
| SLC8A3 | −2.224 | 2.00E−12 | solute carrier family 8 (sodium/calcium exchanger), member 3 |
| MPZ | −2.105 | 7.66E−13 | myelin protein zero |
| ZNF488 | −1.464 | 4.44E−07 | zinc finger protein 488 |
| Wnt signaling (4 genes) | | | |
| WNT7B | −2.626 | 1.46E−07 | wingless-type MMTV integration site family member 7B |
| PCDH15 | −2.530 | 1.42E−10 | protocadherin-related 15 |
| PCDH11X | −2.364 | 1.25E−08 | protocadherin 11 X-linked |
| CDH10 | −1.646 | 9.33E−07 | cadherin 10 |
| Enzymes (15 genes) | | | |
| SLFN13 | 2.832 | 2.18E−13 | schlafen family member 13 |
| SLFN11 | 2.193 | 6.47E−09 | schlafen family member 11 |
| HS3ST4 | 2.149 | 1.44E−04 | heparan sulfate-glucosamine 3-sulfotransferase 4 |
| ALOX5 | 1.777 | 2.35E−05 | arachidonate 5-lipoxygenase |
| CA10 | −3.550 | 3.07E−08 | carbonic anhydrase X |
| NEU4 | −3.361 | 8.31E−40 | neuraminidase 4 (sialidase) |

TABLE 2-continued

Significantly dysregulated genes in SCZ-derived relative to control-derivedOPCs
Table 2. Significantly dysregulated genes in SCZ relative to control GPCs. These tables list shared genes differentially expressed by hiPSC GPCs derived from 4 schizophrenic patients, relative to the pooled gene expression pattern of hGPCs derived from 3 control-derived iPSCs (log2 fold change > 1.0, FDR 5%, 116 genes total, red, upregulated in SCZ vs CTRL; green, downregulated in SCZ GPCs; color intensity proportionate to differential dysregulation). The fold-changes (FC) and FDR-adjusted p values shown here were derived from the comparison of the pooled schizophrenia-derived GPC cell lines to the pooled control-derived GPC lines. The dysregulated genes were grouped into functional sets according to their cellular roles and localizations.

| Gene ID | Log2 FC | P Value | Entrez Gene Name |
|---|---|---|---|
| UGT8 | −3.250 | 4.36E−09 | UDP glycosyltransferase 8 |
| GAL3ST1 | −2.681 | 4.01E−12 | galactose-3-O-sulfotransferase 1 |
| CNTN1 | −2.675 | 5.65E−15 | contactin 1 |
| CSMD3 | −2.560 | 5.78E−10 | CUB and Sushi multiple domains 3 |
| GALNT13 | −2.467 | 2.80E−11 | polypeptide N-acetylgalactosaminyltransferase 13 |
| FA2H | −2.440 | 4.45E−08 | fatty acid 2-hydroxylase |
| AOAH | −2.271 | 2.99E−12 | acyloxyacyl hydrolase |
| KIF19 | −1.644 | 5.10E−06 | kinesin family member 19 |
| DSEL | −1.151 | 1.35E−10 | dermatan sulfate epimerase-like |
| Lipid & lipoprotein metabolism (5 genes) | | | |
| ALOX5 | 1.777 | 2.35E−05 | arachidonate 5-lipoxygenase |
| NEU4 | −3.361 | 8.31E−40 | neuraminidase 4 (sialidase) |
| GAL3ST1 | −2.681 | 4.01E−12 | galactose-3-O-sulfotransferase 1 |
| PLPPR1 | −2.652 | 1.16E−09 | phospholipid phosphatase related 1 |
| PLPPR5 | −1.573 | 1.69E−09 | phospholipid phosphatase related 5 |
| Kinases & phosphatases (6 genes) | | | |
| PTPRT | 4.410 | 1.69E−17 | protein tyrosine phosphatase, receptor type T |
| PPP1R16B | −2.665 | 1.29E−09 | protein phosphatase 1 regulatory subunit 16B |
| PPAPDC1A | −2.357 | 6.76E−09 | phospholipid phosphatase 4 |
| DGKG | −2.306 | 9.29E−12 | diacylglycerol kinase gamma |
| EPHB1 | −1.344 | 3.89E−17 | EPH receptor B1 |
| PNCK | −1.226 | 4.25E−08 | pregnancy up-regulated nonubiquitous CaM kinase |
| Adhesion molecules (5 genes) | | | |
| DSCAM | −3.148 | 1.58E−12 | Down syndrome cell adhesion molecule |
| ASTN2 | −2.242 | 4.70E−21 | astrotactin 2 |
| OPCML | −2.099 | 7.87E−10 | opioid binding protein/cell adhesion molecule-like |
| BAI1 | −2.000 | 1.31E−12 | adhesion G protein-coupled receptor B1 |
| CDH10 | −1.646 | 9.33E−07 | cadherin 10 |
| GPCR signaling (10 genes) | | | |
| CCL2 | 1.832 | 1.97E−07 | chemokine (C-C motif) ligand 2 |
| GPR17 | −3.357 | 1.94E−10 | G protein-coupled receptor 17 |
| GPR45 | −2.895 | 2.95E−14 | G protein-coupled receptor 45 |
| WNT7B | −2.626 | 1.46E−07 | wingless-type MMTV integration site family member 7B |
| GPR139 | −2.589 | 1.32E−08 | G protein-coupled receptor 139 |
| OMG | −2.561 | 5.09E−12 | oligodendrocyte myelin glycoprotein |
| CRHR1 | −2.382 | 5.81E−12 | corticotropin releasing hormone receptor 1 |
| DGKG | −2.306 | 9.29E−12 | diacylglycerol kinase gamma |
| BAI1 | −2.000 | 1.31E−12 | adhesion G protein-coupled receptor B1 |
| GPR123 | −1.807 | 1.76E−18 | adhesion G protein-coupled receptor A1 |
| Growth factors (3 genes) | | | |
| FGF14 | −2.021 | 5.14E−07 | fibroblast growth factor 14 |
| FGF12 | −1.988 | 5.47E−09 | fibroblast growth factor 12 |
| CSPG5 | −1.285 | 6.38E−17 | chondroitin sulfate proteoglycan 5 |
| Cytokines (2 genes) | | | |
| CCL2 | 1.832 | 1.97E−07 | chemokine (C-C motif) ligand 2 |
| CMTM5 | −3.023 | 3.69E−15 | CKLF-like MARVEL transmembrane domain containing 5 |
| Synaptic-junction associated (32 genes) | | | |
| CCL2 | 1.832 | 1.97E−07 | chemokine (C-C motif) ligand 2 |
| ALOX5 | 1.777 | 2.35E−05 | arachidonate 5-lipoxygenase |
| BRINP3 | −3.433 | 4.70E−22 | bone morphogenetic protein/retinoic acid inducible neural-specific 3 |
| DSCAM | −3.148 | 1.58E−12 | Down syndrome cell adhesion molecule |
| KCND2 | −3.145 | 5.67E−11 | potassium channel, voltage gated Shal related subfamily D, member 2 |
| NXPH1 | −2.892 | 3.11E−15 | neurexophilin 1 |
| CHRNA4 | −2.755 | 4.45E−14 | cholinergic receptor, nicotinic alpha 4 |
| ARHGAP36 | −2.686 | 1.21E−05 | Rho GTPase activating protein 36 |
| CNTN1 | −2.675 | 5.65E−15 | contactin 1 |
| NETO1 | −2.633 | 2.52E−12 | neuropilin and tolloid like 1 |
| PLLP | −2.581 | 1.21E−24 | plasmolipin |
| PCDH15 | −2.530 | 1.42E−10 | protocadherin-related 15 |
| GRIA4 | −2.519 | 1.84E−09 | glutamate receptor, ionotropic, AMPA 4 |
| BCAN | −2.473 | 7.35E−32 | brevican |
| GABRA3 | −2.450 | 1.08E−12 | gamma-aminobutyric acid (GABA) A receptor, alpha 3 |

TABLE 2-continued

Significantly dysregulated genes in SCZ-derived relative to control-derivedOPCs
Table 2. Significantly dysregulated genes in SCZ relative to control GPCs. These tables list shared genes differentially expressed by hiPSC GPCs derived from 4 schizophrenic patients, relative to the pooled gene expression pattern of hGPCs derived from 3 control-derived iPSCs (log2 fold change > 1.0, FDR 5%, 116 genes total, red, upregulated in SCZ vs CTRL; green, downregulated in SCZ GPCs; color intensity proportionate to differential dysregulation). The fold-changes (FC) and FDR-adjusted p values shown here were derived from the comparison of the pooled schizophrenia-derived GPC cell lines to the pooled control-derived GPC lines. The dysregulated genes were grouped into functional sets according to their cellular roles and localizations.

| Gene ID | Log2 FC | P Value | Entrez Gene Name |
|---|---|---|---|
| CRHR1 | −2.382 | 5.81E−12 | corticotropin releasing hormone receptor 1 |
| SHISA7 | −2.302 | 1.43E−14 | shisa family member 7 |
| SLC8A3 | −2.224 | 2.00E−12 | solute carrier family 8 (sodium/calcium exchanger), member 3 |
| MPZ | −2.105 | 7.66E−13 | myelin protein zero |
| GRID2 | −2.055 | 3.65E−06 | glutamate receptor, ionotropic, delta 2 |
| RPH3A | −2.014 | 1.01E−06 | rabphilin 3A |
| VWC2 | −2.003 | 9.67E−13 | von Willebrand factor C domain containing 2 |
| CTTNBP2 | −1.904 | 7.21E−08 | cortactin binding protein 2 |
| MT3 | −1.795 | 5.27E−09 | metallothionein 3 |
| KCNA3 | −1.719 | 3.03E−12 | potassium channel, voltage gated shaker related subfamily A, member 3 |
| BRINP2 | −1.625 | 2.03E−12 | bone morphogenetic protein/retinoic acid inducible neural-specific 2 |
| LGI3 | −1.614 | 4.07E−08 | leucine-rich repeat LGI family member 3 |
| SLC6A1 | −1.596 | 5.52E−11 | solute carrier family 6 (neurotransmitter transporter), member 1 |
| GRID1 | −1.562 | 7.61E−07 | glutamate receptor, ionotropic, delta 1 |
| GRIK4 | −1.547 | 2.73E−07 | glutamate receptor, ionotropic, kainate 4 |
| KCNK9 | −1.460 | 4.40E−06 | potassium channel, two pore domain subfamily K, member 9 |
| EPHB1 | −1.344 | 3.89E−17 | EPH receptor B1 |
| Ion channels (10 genes) | | | |
| KCND2 | −3.145 | 5.67E−11 | potassium channel, voltage gated Shal related subfamily D, member 2 |
| GRIA4 | −2.519 | 1.84E−09 | glutamate receptor, ionotropic, AMPA 4 |
| GABRA3 | −2.450 | 1.08E−12 | gamma-aminobutyric acid (GABA) A receptor, alpha 3 |
| ASIC4 | −2.321 | 4.13E−14 | acid sensing ion channel subunit family member 4 |
| KCN39 | −2.187 | 2.85E−21 | potassium channel, inwardly rectifying subfamily 3, member 9 |
| GRID2 | −2.055 | 3.65E−06 | glutamate receptor, ionotropic, delta 2 |
| KCNA3 | −1.719 | 3.03E−12 | potassium channel, voltage gated shaker related subfamily A, member 3 |
| GRID1 | −1.562 | 7.61E−07 | glutamate receptor, ionotropic, delta 1 |
| GRIK4 | −1.547 | 2.73E−07 | glutamate receptor, ionotropic, kainate 4 |
| KCNK9 | −1.460 | 4.40E−06 | potassium channel, two pore domain subfamily K, member 9 |
| Transporters (6 genes) | | | |
| AZGP1 | −3.323 | 1.66E−08 | alpha-2-glycoprotein 1, zinc-binding |
| PLLP | −2.581 | 1.21E−24 | plasmolipin |
| SNX22 | −2.297 | 3.53E−20 | sorting nexin 22 |
| SLC8A3 | −2.224 | 2.00E−12 | solute carrier family 8 (sodium/calcium exchanger), member 3 |
| RPH3A | −2.014 | 1.01E−06 | rabphilin 3A |
| SLC6A1 | −1.596 | 5.52E−11 | solute carrier family 6 (neurotransmitter transporter), member 1 |
| Extracellular matrix-associated (14 genes) | | | |
| CCL2 | 1.832 | 1.97E−07 | chemokine (C-C motif) ligand 2 |
| COL20A1 | −3.476 | 7.33E−14 | collagen, type XX, alpha 1 |
| BRINP3 | −3.433 | 4.70E−22 | bone morphogenetic protein/retinoic acid inducible neural-specific 3 |
| WNT7B | −2.626 | 1.46E−07 | wingless-type MMTV integration site family member 7B |
| BCAN | −2.473 | 7.35E−32 | brevican |
| FGF14 | −2.021 | 5.14E−07 | fibroblast growth factor 14 |
| VWC2 | −2.003 | 9.67E−13 | von Willebrand factor C domain containing 2 |
| FGF12 | −1.988 | 5.47E−09 | fibroblast growth factor 12 |
| LUZP2 | −1.948 | 7.22E−06 | leucine zipper protein 2 |
| ELFN2 | −1.943 | 1.47E−06 | extracellular Leu-rich repeat and fibronectin type III domain containing 2 |
| KY | −1.873 | 2.41E−13 | kyphoscoliosis peptidase |
| BRINP2 | −1.625 | 2.03E−12 | bone morphogenetic protein/retinoic acid inducible neural-specific 2 |
| LGI3 | −1.614 | 4.07E−08 | leucine-rich repeat LGI family member 3 |
| CSPG5 | −1.285 | 6.38E−17 | chondroitin sulfate proteoglycan 5 |
| Transmembrane proteins (5 genes) | | | |
| TMEM257 | −4.018 | 5.58E−23 | transmembrane protein 257 |
| CMTM5 | −3.023 | 3.69E−15 | CKLF-like MARVEL transmembrane domain containing 5 |
| CHRNA4 | −2.755 | 4.45E−14 | cholinergic receptor, nicotinic alpha 4 |
| LINGO1 | −2.139 | 3.56E−14 | leucine-rich repeat and Ig domain containing 1 |
| TMEM229B | −1.187 | 7.76E−06 | transmembrane protein 229B |

TABLE 2-continued

Significantly dysregulated genes in SCZ-derived relative to control-derivedOPCs
Table 2. Significantly dysregulated genes in SCZ relative to control GPCs. These tables list shared genes
differentially expressed by hiPSC GPCs derived from 4 schizophrenic patients, relative to the pooled gene
expression pattern of hGPCs derived from 3 control-derived iPSCs (log2 fold change > 1.0, FDR 5%, 116 genes
total, red, upregulated in SCZ vs CTRL; green, downregulated in SCZ GPCs; color intensity proportionate to
differential dysregulation). The fold-changes (FC) and FDR-adjusted p values shown here were derived from the
comparison of the pooled schizophrenia-derived GPC cell lines to the pooled control-derived GPC lines. The
dysregulated genes were grouped into functional sets according to their cellular roles and localizations.

| Gene ID | Log2 FC | P Value | Entrez Gene Name |
|---|---|---|---|
| Cytoplasmic & membrane-associated (15 genes) | | | |
| CCL2 | 1.832 | 1.97E−07 | chemokine (C-C motif) ligand 2 |
| BTN3A2 | 1.355 | 8.10E−20 | butyrophilin subfamily 3 member A2 |
| BEX5 | −3.885 | 2.55E−21 | brain expressed X-linked 5 |
| ARHGAP36 | −2.686 | 1.21E−05 | Rho GTPase activating protein 36 |
| WNT7B | −2.626 | 1.46E−07 | wingless-type MMTV integration site family member 7B |
| GRIA4 | −2.519 | 1.84E−09 | glutamate receptor, ionotropic, AMPA 4 |
| SNX22 | −2.297 | 3.53E−20 | sorting nexin 22 |
| LHFPL3 | −2.250 | 1.71E−07 | lipoma HMGIC fusion partner-like 3 |
| RPH3A | −2.014 | 1.01E−06 | rabphilin 3A |
| CTTNBP2 | −1.904 | 7.21E−08 | cortactin binding protein 2 |
| SHC3 | −1.830 | 7.88E−19 | SHC (Src homology 2 domain containing) transforming protein 3 |
| MT3 | −1.795 | 5.27E−09 | metallothionein 3 |
| LGI3 | −1.614 | 4.07E−08 | leucine-rich repeat LGI family member 3 |
| KCNK9 | −1.460 | 4.40E−06 | potassium channel, two pore domain subfamily K, member 9 |
| CSPG5 | −1.285 | 6.38E−17 | chondroitin sulfate proteoglycan 5 |
| lincRNAs, ORFs, & uncharacterized (25 genes) | | | |
| RPS12P11 | 1.647 | 9.02E−30 | not available |
| LOC101927206 | −3.592 | 2.74E−63 | not available |
| LOC100505797 | −3.266 | 3.10E−27 | myosin heavy chain IB-like |
| C10orf85 | −3.081 | 3.52E−10 | long intergenic non-protein coding RNA 1561 |
| CXXC11 | −2.814 | 7.70E−19 | receptor (chemosensory) transporter protein 5 (putative) |
| LOC284395 | −2.792 | 1.20E−10 | uncharacterized LOC284395 |
| RP11-547I7.2 | −2.779 | 4.81E−34 | not available |
| AC009227.2 | −2.758 | 3.05E−13 | not available |
| LOC101928430 | −2.691 | 5.56E−10 | not available |
| FLJ38379 | −2.389 | 1.25E−15 | not available |
| LOC102723927 | −2.363 | 7.74E−21 | uncharacterized LOC102723927 |
| RP11-1055B8.3 | −2.336 | 1.02E−16 | not available |
| AC131097.3 | −2.180 | 5.80E−16 | not available |
| C1orf94 | −2.077 | 7.03E−11 | chromosome 1 open reading frame 94 |
| HMGA1P7 | −2.057 | 4.49E−09 | high mobility group AT-hook 1 pseudogene 7 |
| LOC101929249 | −2.003 | 1.52E−06 | uncharacterized LOC101929249 |
| LOC101927646 | −2.001 | 1.22E−10 | uncharacterized LOC101927646 |
| AC010890.1 | −1.937 | 3.53E−10 | not available |
| C2orf80 | −1.924 | 6.74E−18 | chromosome 2 open reading frame 80 |
| MAPT-AS1 | −1.844 | 5.40E−07 | MAPT antisense RNA 1 |
| LOC100128127 | −1.814 | 1.43E−09 | not available |
| RP11-1134I14.8 | −1.783 | 5.72E−22 | not available |
| SLC6A1-AS1 | −1.706 | 1.31E−09 | SLC6A1 antisense RNA 1 |
| KIAA1244 | −1.643 | 1.63E−10 | ARFGEF family member 3 |
| FAM222A-AS1 | −1.297 | 1.10E−11 | FAM222A antisense RNA 1 |

These expression data suggest that the diminished myelination of SCZ hGPC-transplanted shiverer brains reflected aberrant oligodendrocytic differentiation from the engrafted SCZ hGPCs. Similarly, since hGPCs give rise to astrocytes as well as oligodendrocytes, the RNA expression data suggest an analogous impediment to astrocytic differentiation. The functional consequences of the latter are especially profound, given the critical role for astrocytes in synaptic development and function; indeed, the relative suppression of astrocytic differentiation by SCZ hGPCs suggests a glial contribution to the impaired synaptic function noted in schizophrenia. In that regard, further functional analysis of SCZ-associated dysregulated hGPC genes identified channel and receptor activity, as well as synaptic transmission, as the most differentially affected functions besides glial differentiation (FIGS. 6D-6E). These disease-linked channel and synapse-associated genes were largely down-regulated in the SCZ hGPCs, and included a number of potassium channel genes (FIG. 6D), including KCND2, KCNJ9, KCNK9 and KCNA3, as well as a number of transcripts associated with synaptic development and function (FIG. 6E and Table 2). The latter included NXPH1, NLGN3, and LINGO1, among others (Table 3), synaptic genes whose dysregulation has been previously linked to both SCZ and the autism spectrum disorders (Sudhof, T. C., "Neuroligins and Neurexins Link Synaptic Function to Cognitive Disease," *Nature* 455:903-911 (2008); Andrews et al., "A Decade From Discovery to Therapy: Lingo-1, the Dark Horse in Neurological and Psychiatric Disorders," *Neurosci Biobehav Rev* 56:97-114 (2015); Fernandez-Enright et al., "Novel Implications of Lingo-1 and its Signaling Partners in Schizophrenia," *Translational psychiatry* 4:e348 (2014); Mackowiak et al., "Neuroligins, Synapse Balance and Neuropsychiatric Disorders," *Pharmacol Rep* 66:830-835 (2014); Salyakina et al., "Copy Number Variants in Extended Autism Spectrum Disorder Families Reveal Candidates Potentially Involved in Autism Risk," *PloS one* 6:e26049 (2011), which are hereby incorporated by reference in their entirety).

associated transcript closely linked to schizophrenia (Sudhof, T. C., "Neuroligins and Neurexins Link Synaptic Function to Cognitive Disease," *Nature* 455:903-911

TABLE 3

Genomic analysis of SCZ-derived hGPCs from 4 different patients revealed the significant and shared down-regulation in these cells of a number of synaptic genes, including neuroligin-3, neuroexophilin-1, LINGO1 and DSCAML1, relative to their normal controls (red, upregulated in SCZ vs CTRL; green, downregulated in SCZ GPCs; color intensity proportionate to differential dysregulation). Other synapse-associated genes, such as the SLITRKs 2-5, were significantly and sharply downregulated in GPCs derived from 3 of the 4 patients (lines 8, 51 and 164). Lines 08, 29, 51 and 164: schizophrenia-derived, different patients; pooled controls, 3 lines, each from a different patient. Individual SCZ line data shown as well as pooled SCZ data, to highlight both commonalities and distinctions between SCZ GPCs derived from different patients. Log2FC: $\log_2$ fold-change in expression. NS: not significant.

| | SCZ.08 vs. Pooled CTR | | SCZ.29 vs. Pooled CTR | | SCZ.51 vs. Pooled CTR | | SCZ.164 vs. Pooled CTR | | SCZ.08 + 29 + 51 + 164 vs. Pooled CTR | |
|---|---|---|---|---|---|---|---|---|---|---|
| Gene ID | Log2 FC | P Value | Log2 FC | P Value | Log2 FC | P Value | Log2 FC | P Value | Log2 FC | P Value |
| DSCAML1 | −1.971 | 8.83E−07 | −2.968 | 1.31E−04 | −1.089 | 8.32E−05 | NS | NS | −0.982 | 5.34E−08 |
| LINGO1 | −2.320 | 3.29E−04 | −2.885 | 2.26E−04 | −1.452 | 3.36E−06 | −2.523 | 9.19E−12 | −2.139 | 3.56E−14 |
| NLGN1 | −1.249 | 3.37E−04 | −1.014 | 4.32E−02 | NS | NS | −0.545 | 3.88E−02 | −0.625 | 3.15E−04 |
| NLGN2 | NS | NS | −0.767 | 1.74E−02 | −0.384 | 3.01E−03 | −0.408 | 1.47E−02 | −0.452 | 3.37E−06 |
| NLGN3 | −0.563 | 3.98E−02 | −1.669 | 3.07E−03 | −1.011 | 1.63E−09 | −0.958 | 3.67E−05 | −1.143 | 1.61E−19 |
| NRP1 | −1.362 | 1.15E−03 | 1.409 | 5.00E−04 | NS | NS | NS | NS | NS | NS |
| NRP2 | NS | NS | 1.548 | 2.07E−03 | NS | NS | −0.733 | 3.65E−02 | NS | NS |
| NRXN1 | −3.259 | 5.93E−06 | −2.984 | 5.55E−03 | −1.176 | 1.35E−02 | NS | NS | −1.161 | 2.04E−04 |
| NRXN2 | NS | NS | −2.179 | 9.04E−06 | −1.252 | 2.71E−11 | −0.720 | 3.33E−03 | −1.102 | 6.82E−17 |
| NRXN3 | 1.874 | 1.60E−04 | NS | NS | NS | NS | 1.198 | 1.20E−02 | 0.909 | 6.89E−04 |
| NTNG2 | −0.874 | 7.99E−03 | −1.814 | 3.51E−04 | NS | NS | NS | NS | NS | NS |
| NXPE3 | NS | NS | NS | NS | NS | NS | 0.410 | 1.74E−02 | 0.248 | 2.79E−02 |
| NXPH1 | −3.019 | 3.98E−07 | −3.666 | 1.84E−03 | −1.338 | 1.06E−02 | −2.317 | 2.46E−09 | −2.892 | 3.11E−15 |
| NXPH2 | −2.288 | 5.62E−04 | NS | NS | NS | NS | NS | NS | NS | NS |
| NXPH3 | NS | NS | −2.225 | 1.49E−03 | −1.084 | 7.92E−03 | NS | NS | −0.675 | 2.66E−02 |
| NXPH4 | −2.186 | 5.96E−03 | 4.095 | 4.08E−14 | NS | NS | −1.560 | 1.09E−02 | NS | NS |
| PTPRZ1 | NS | NS | −2.967 | 2.60E−05 | −0.792 | 4.13E−03 | −0.870 | 5.38E−03 | −1.296 | 2.41E−11 |
| RGS4 | −1.982 | 6.80E−05 | 2.184 | 3.97E−04 | 1.105 | 7.04E−04 | −1.419 | 2.64E−03 | NS | NS |
| SLITRK2 | −6.812 | 1.35E−04 | NS | NS | −7.307 | 7.51E−25 | −9.321 | 5.54E−06 | −6.138 | 5.52E−14 |
| SLITRK3 | −2.958 | 2.68E−03 | NS | NS | −1.698 | 6.37E−04 | −3.490 | 1.61E−11 | −2.502 | 6.76E−07 |
| SLITRK4 | −4.157 | 7.12E−05 | NS | NS | −3.713 | 5.02E−05 | −2.678 | 1.20E−02 | −2.457 | 5.86E−05 |
| SLITRK5 | −2.047 | 3.87E−07 | NS | NS | −1.184 | 1.54E−06 | −1.734 | 9.31E−08 | −1.152 | 1.05E−08 |
| SPARCL1 | −2.314 | 6.14E−06 | NS | NS | NS | NS | −0.843 | 3.87E−02 | NS | NS |
| TNR | −3.082 | 8.83E−06 | −5.108 | 1.89E−07 | −2.227 | 8.81E−13 | NS | NS | −2.137 | 5.56E−12 |

Whereas the expression of these latter genes was suppressed in hGPCs derived from all 4 SCZ patients, other synapse-associated genes, such as NRXN1, NLGN1, DSCAML1, and the SLITRKs 2-5, were sharply down-regulated in hGPCs derived from 3 of the 4 patients, but not in the fourth (Table 3). Yet other synapse-associated transcripts, like NXPH3 and NTRNG2, were similarly down-regulated in some patients, but not others. TaqMan low density arrays were used for quantitative real-time PCR validation of these and other dysregulated transcripts of interest, and validated the significant differential down-regulation of these differentiation and synaptic function-associated genes (Table 4 and FIG. 8).

Figure 9:
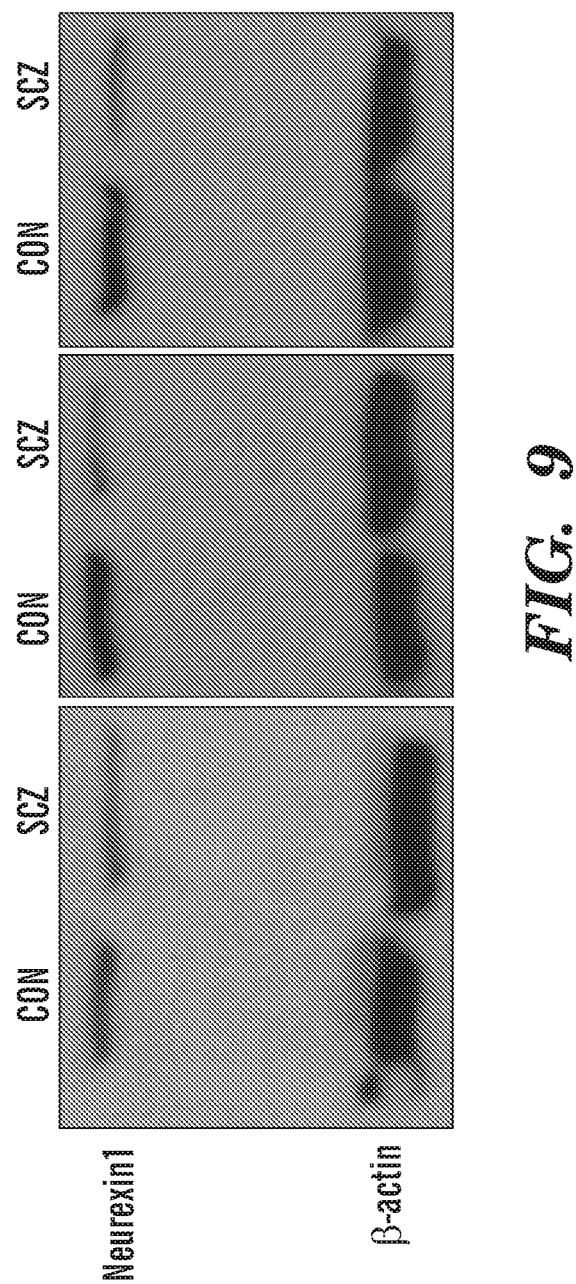
FIG. 9 shows neurexin-1 expression was suppressed in SCZ hGPCs. Western blots revealed that neurexin-1 protein was abundantly expressed by human GPCs purified by CD140a-directed FACS, and that neurexin-1 levels were lower in otherwise matched SCZ hGPCs (line 51 SCZ hGPCs vs. line 22 CTRL hGPCs).

Together, these data suggest the importance of glial-associated synaptic gene expression in schizophrenia, while emphasizing the heterogeneity of pathways that might be mechanistically complicit in its dysregulation. These data also highlight the point that while the neuronal localization of these synaptic proteins has long been recognized, their synthesis by glia and synaptic contributions thereof have not been specifically discussed, although cell type-specific transcriptional databases have noted significant glial expression of these genes (Zhang et al., "An RNA-Sequencing Transcriptome and Splicing Database of Glia, Neurons, and Vascular Cells of the Cerebral Cortex," *The Journal of Neuroscience: The Official Journal of the Society for Neuroscience* 34:11929-11947 (2014), which is hereby incorporated by reference in its entirety). Since NRXN1, a synapse- (2008), which is hereby incorporated by reference in its entirety), was one of the most strongly and consistently down-regulated glial genes across the patients, the down-regulation of its expression by SCZ glia was verified, by immunoblotting CD140a-sorted, neuron-free isolates of SCZ and control hGPCs. Western blots revealed that neurexin-1 was indeed abundantly expressed by human GPCs, and that neurexin-1 protein levels were sharply lower in otherwise matched SCZ hGPCs (FIG. 9).

TABLE 4

Table 4. Expression of selected genes identified by RNA-seq analysis as dysregulated in SCZ-derived GPCs was assessed by TaqMan Low Density Array (TLDA) RT-qPCR, and compared to that of control GPCs. Expression data were normalized to GAPDH endogenous control. Mean expression ratios calculated from 4 pooled SCZ GPC lines (n =19) against 3 pooled control GPC lines (n = 10) are shown. The difference of expression in SCZ and control GPCs was assessed by paired t-test followed by multiple testing correction by Benjamini-Hochberg (BH) procedure. BH-corrected P values are shown (* = P < 0.01,  = P < 0.05, * = P < 0.1). 48 genes were assessed.

| | Gene Symbol | qPCR Ratio (min-max; P Value) |
|---|---|---|
| Transcription regulators | LINGO1*** | 0.105 (0.064-0.174; P = 2.20E−03) |
| | MYRF | 0.263 (0.092-0.754; P = 1.11E−01) |
| | NKX2-2** | 0.253 (0.115-0.556; P = 2.17E−02) |
| | OLIG1*** | 0.170 (0.076-0.381; P = 4.83E−03) |
| | OLIG2*** | 0.119 (0.053-0.268; P = 1.09E−03) |
| | SOX10*** | 0.049 (0.013-0.178; P = 1.09E−03) |

TABLE 4-continued

Table 4. Expression of selected genes identified by RNA-seq analysis as dysregulated in SCZ-derived GPCs was assessed by TaqMan Low Density Array (TLDA) RT-qPCR, and compared to that of control GPCs. Expression data were normalized to GAPDH endogenous control. Mean expression ratios calculated from 4 pooled SCZ GPC lines (n =19) against 3 pooled control GPC lines (n = 10) are shown. The difference of expression in SCZ and control GPCs was assessed by paired t-test followed by multiple testing correction by Benjamini-Hochberg (BH) procedure. BH-corrected P values are shown (* = P < 0.01,  = P < 0.05, * = P < 0.1). 48 genes were assessed.

|  | Gene Symbol | qPCR Ratio (min-max; P Value) |
|---|---|---|
|  | SOX9* | 0.692 (0.524-0.914; P = 7.76E−02) |
|  | TCF7L2* | 0.639 (0.451-0.906; P = 7.70E−02) |
|  | ZNF488** | 0.130 (0.042-0.397; P = 2.12E−02) |
| Myelination- | CNTN1*** | 0.076 (0.046-0.127; P = 9.83E−04) |
| associated | FA2H*** | 0.040 (0.010-0.171; P = 1.34E−03) |
|  | GPR17** | 0.094 (0.019-0.467; P = 2.18E−02) |
|  | MPZ | 0.482 (0.211-1.103; P = 4.99E−01) |
|  | OMG*** | 0.154 (0.082-0.287; P = 1.09E−03) |
|  | SIRT2*** | 0.401 (0.307-0.524; P = 4.54E−03) |
|  | UGT8*** | 0.045 (0.012-0.160; P = 1.09E−03) |
| Synaptic | ATP2B2*** | 0.209 (0.113-0.385; P = 2.49E−03) |
| junction- | BCAN*** | 0.191 (0.113-0.323; P = 2.49E−03) |
| associated | CD44** | 2.397 (1.435-4.007; P = 3.19E−02) |
|  | CRHR1** | 0.183 (0.058-0.583; P = 2.24E−02) |
|  | DSCAML1*** | 0.302 (0.190-0.480; P = 2.49E−03) |
|  | LGI1 | 0.821 (0.228-2.957; P = 8.10E−01) |
|  | NETO1*** | 0.095 (0.042-0.214; P = 9.83E−04) |
|  | NRXN1** | 0.252 (0.124-0.510; P = 2.12E−02) |
|  | NTNG1** | 0.348 (0.149-0.817; P = 4.69E−02) |
|  | NTNG2 | 0.569 (0.223-1.451; P = 3.66E−01) |
|  | NXPH1*** | 0.085 (0.034-0.216; P = 1.30E−03) |
|  | RPH3A*** | 0.205 (0.130-0.324; P = 3.24E−03) |
|  | SLC6A1*** | 0.188 (0.094-0.378; P = 4.44E−03) |
|  | SLITRK2** | 0.010 (0.003-0.033; P = 3.19E−02) |
|  | SLITRK3*** | 0.074 (0.025-0.220; P = 1.33E−03) |
|  | SLITRK4* | 0.101 (0.030-0.335; P = 5.73E−02) |
|  | SPARCL1* | 0.507 (0.275-0.936; P = 9.14E−02) |
|  | TNR*** | 0.102 (0.045-0.228; P = 9.83E−04) |
| Ion channels | KCNA3** | 0.270 (0.166-0.439; P = 1.30E−02) |
|  | KCND2*** | 0.070 (0.025-0.196; P = 1.09E−03) |
|  | KCNH8 | 0.534 (0.261-1.093; P = 2.56E−01) |
|  | KCN39** | 0.257 (0.151-0.439; P = 2.24E−02) |
|  | KCNK9** | 0.159 (0.061-0.411; P = 1.28E−02) |
| Actin | ACTB | 1.365 (1.016-1.833; P = 1.27E−01) |
| Astrocyte-specific marker | GFAP | 1.479 (0.819-2.672; P = 4.25E−01) |
| Enzyme | ALDH1L1 | 0.596 (0.164-2.170; P = 5.67E−01) |
| Growth factor | FGF14*** | 0.085 (0.034-0.213; P = 1.33E−03) |
| RNA binding protein | ELAVL4 | 0.585 (0.374-0.915; P = 1.61E−01) |
| Wnt signaling | WNT7B* | 0.149 (0.042-0.527; P = 5.43E−02) |

45 genes are shown, excluding the endogenous control and genes that had high proportion of undetermined and unreliable reactions, LRFN1 and NEUROD6. The vast majority of genes were confirmed as dysregulated in SCZ-derived GPCs which reliably exhibited the significant differential down-regulation of differentiation, potassium channel and synapse function-associated genes. Analysis of TLDA data was performed in ExpressionSuite Software version 1.1 supplied by Applied Biosciences.

Example 5

SCZ Glial Chimerization Yielded Disease-Specific Behavioral Phenotype

It was next asked whether the alterations in glial distribution and differentiation observed in mice engrafted with SCZ hGPCs might alter the behavioral phenotype of the host mice. In particular, it was postulated that the aberrant infiltration of hGPCs and their derived astroglia into the developing cortex might influence information processing within the cortex once mature. As noted, past studies have reported both the influence of astrocytic networks on synaptic efficacy and plasticity, and the differential competence of hominid glia in this respect (Oberheim et al., "Uniquely Hominid Features of Adult Human Astrocytes," *J. Neurosci.* 29:3276-3287 (2009); Han et al., "Forebrain Engraftment by Human Glial Progenitor Cells Enhances Synaptic Plasticity and Learning in Adult Mice," *Cell Stem Cell* 12:342-353 (2013), which are hereby incorporated by reference in their entirety). Human glial chimeric mice manifest a lower threshold for hippocampal long-term potentiation (LTP) and learn more rapidly, with superior performance in a variety of learning tasks, which include auditory fear conditioning, novel object and place recognition, and Barnes maze navigation. In each of these tests—but not in any test of social interactivity or primary perception—human glial chimeras acquire new causal associations more quickly than do allografted or untransplanted controls (Han et al., "Forebrain Engraftment by Human Glial Progenitor Cells Enhances Synaptic Plasticity and Learning in Adult Mice," *Cell Stem Cell* 12:342-353 (2013), which is hereby incorporated by reference in its entirety). Thus, engrafted human GPCs and their daughter glia can integrate into, and substantially modify, developing neural networks (Franklin et al., "Do Your Glial Cells Make You Clever?," *Cell Stem Cell* 12:265-266 (2013), which is hereby incorporated by reference in its entirety). On that basis, it was postulated that the disruption in normal glial development noted in the SCZ glial chimeras might yield disease-associated changes in learning and behavior. To address this question, the behavioral phenotypes of immunodeficient but otherwise wild-type mice neonatally engrafted with SCZ GPCs were assessed, relative to matched hosts engrafted with control-derived GPCs. For these experiments, normally-myelinated hosts were used rather than shiverer mice, so as to produce mice chimeric only for human GPCs and astrocytes, and not for oligodendroglia, thus isolating any observed behavioral effects to SCZ hGPCs and astrocytes.

Figures 10A, 10B, 10C:
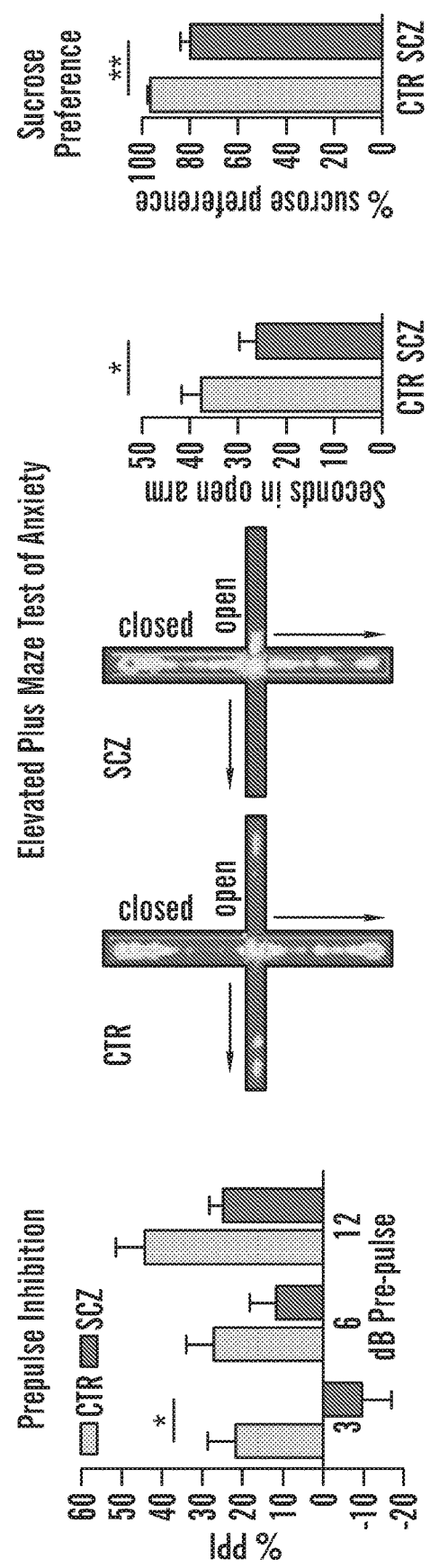
FIGS. 10A-10G show schizophrenia-derived human glial chimeras have significant behavioral abnormalities.
Figure 10D:
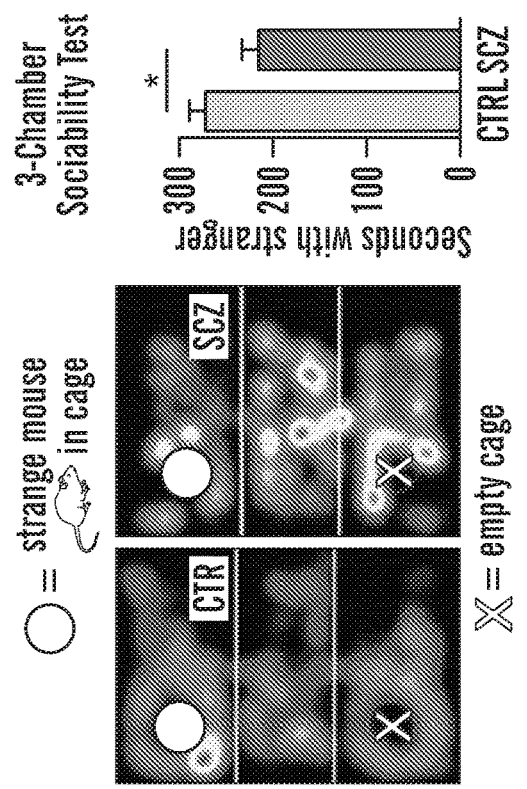
Figure 10E:
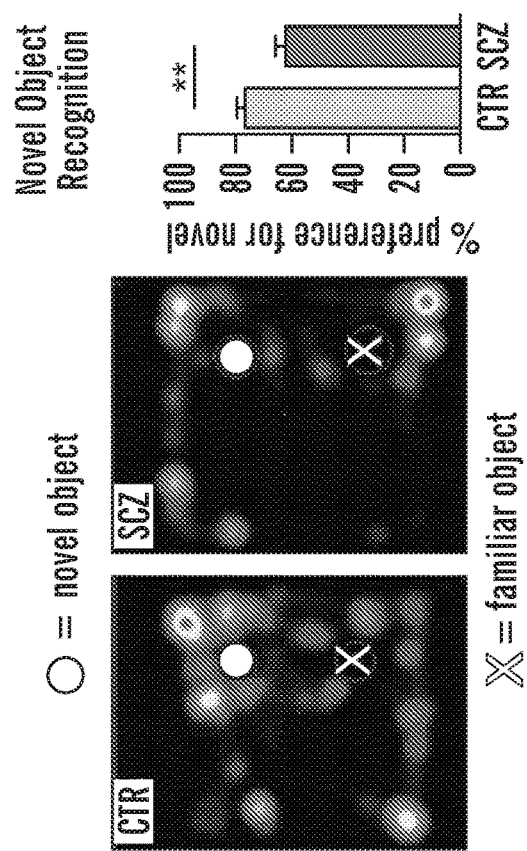

It was first asked whether schizophrenic derivation of engrafted glia affected prepulse inhibition (PPI), a behavioral hallmark of both clinical schizophrenics and animal models thereof (Ewing et al., "Evidence for Impaired Sound Intensity Processing During Prepulse Inhibition of the Startle Response in a Rodent Developmental Disruption Model of Schizophrenia," *Journal of Psychiatric Research* (2013), which is hereby incorporated by reference in its entirety). PPI reflects the coordination of sensorimotor gating in the CNS, and its diminution may predict aspects of schizophrenic phenotype (Ivleva et al., "Smooth Pursuit Eye Movement, Prepulse Inhibition, and Auditory Paired Stimuli Processing Endophenotypes Across the schizophrenia-Bipolar Disorder Dimension," *Schizophrenia Bulletin* (2013); Kohl et al., "Prepulse Inhibition in Psychiatric Disorders—Apart from Schizophrenia," *Journal of Psychiatric Research* 47:445-452 (2013), which is hereby incorporated by reference in its entirety). It was found that when assessed at 6 months of age—the latest time-point at which the C57Bl/6 background strain of the rag1$^{-/-}$ mice can be reliably assessed, since these mice suffer premature auditory loss which might otherwise diminish auditory PPI—that mice engrafted with SCZ hGPCs exhibited significantly diminished auditory prepulse inhibition (FIG. 10A), and did so at all volumes of pre-pulse. Given the strong effect of SCZ glial chimerization on PPI, it was next asked if SCZ glial chimerization might be associated with changes in behavior on cognitive and socialization tests. To that end, SCZ and control chimeras were compared on a battery of behavioral tests that included: 1) the elevated plus maze, a measure of anxiety (Walf et al., "The Use of the Elevated Plus Maze as an Assay of Anxiety-Related Behavior in Rodents," *Nat Protoc* 2:322-328 (2007), which is hereby incorporated by reference in its entirety); 2) the 3-chamber social challenge (Yang et al., "Automated Three-Chambered Social Approach Task for Mice," *Curr Protoc Neurosci*, Chapter 8, Unit 8, 26 (2011), which is hereby incorporated by reference in its entirety); 3) novel object recognition, a focused measure of executive memory (Bevins et al., "Object Recognition in Rats and Mice: A One-Trial Non-Matching-to-Sample Learning Task to Study 'Recognition Memory'," *Nat Protoc* 1:1306-1311 (2006), which is hereby incorporated by reference in its entirety), and 4) the preference for sucrose water, a test for anhedonia (Barnes et al., "Anhedonia, Avolition, and Anticipatory Deficits: Assessments in Animals with Relevance to the Negative Symptoms of Schizophrenia," *Eur Neuropsychopharmacol* 24:744-758 (2014); Willner et al., "Reduction of Sucrose Preference by Chronic Unpredictable Mild Stress, and its Restoration by a Tricyclic Antidepressant," *Psychopharmacology (Berl)* 93:358-364 (1987), which are hereby incorporated by reference in their entirety). In each, mice chimerized with one of 3 SCZ or 3 control patient-derived lines were compared; each line was derived from a different patient. Between 6-12 recipient mice were engrafted and tested per cell line, or 17-36 mice per group for each behavioral comparison, with a typically equal balance of male and female recipients. These animals were tested beginning between 30-36 weeks of age, and testing typically lasted 3 weeks. Over the tested age range, the SCZ GPC chimeric mice exhibited a number of significant differences in behavior relative to their control hGPC-engrafted counterparts. Normal control-engrafted mice are significantly more likely to explore the open arms (horizontal segments), whereas SCZ mice spent most of their time in the closed maze arms (vertical segments), consistent with greater anxiety (p=0.036, 2-tailed t test). The SCZ hGPC mice exhibited greater avoidance of the open arms in the elevated plus maze than did their normal hGPC-engrafted controls (n=36 mice/group, each including 12 mice engrafted with hGPCs from each of 3 patients; p=0.036, 2-tailed t test), suggesting that the SCZ hGPC mice were prone to higher anxiety when challenged (FIG. 10B). In addition, the SCZ hGPC mice showed less preference for sucrose water), consistent with relative anhedonia (FIG. 10C), less interest in stranger mice in the 3-chamber social test (FIG. 10D), and relatively poor novel object recognition (FIG. 10E), reflecting relative impairment in executive memory.

Figure 10G:
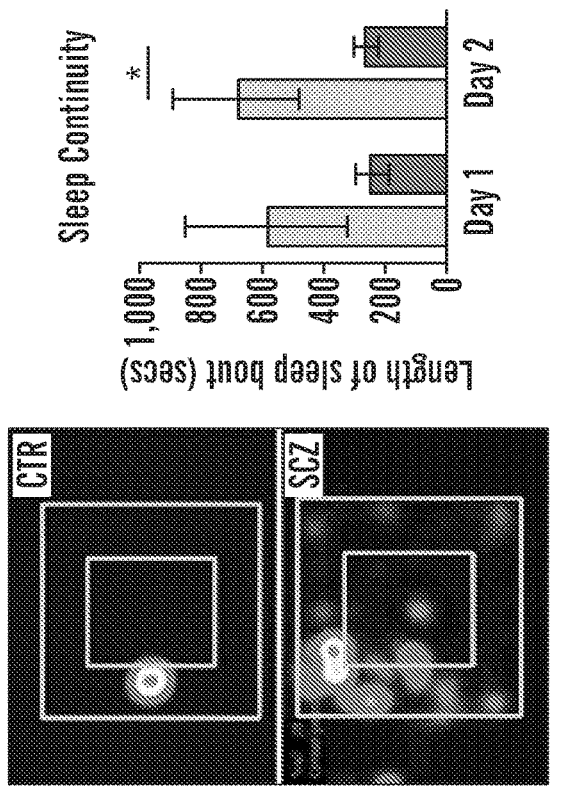
Figure 10F:
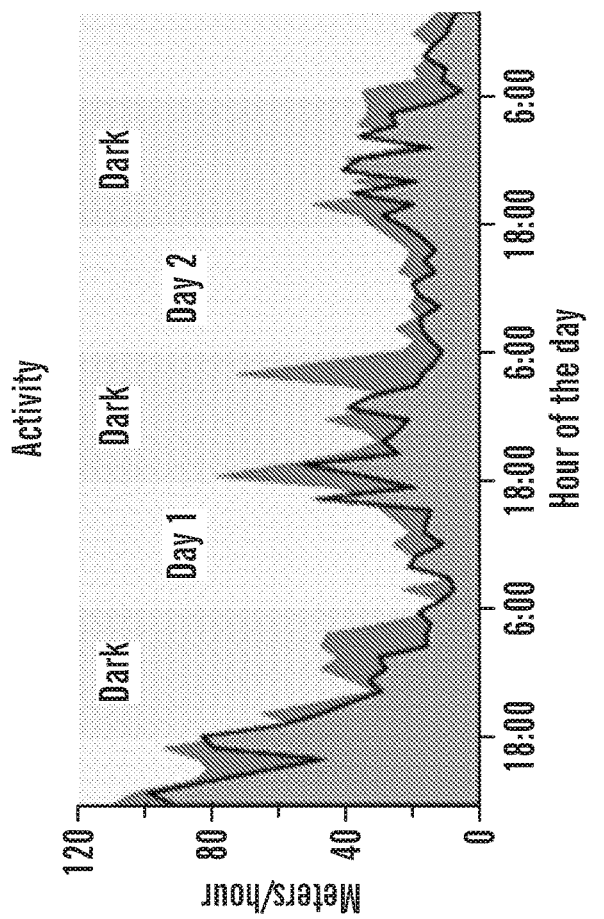

As an additional metric of SCZ-associated behavior, sleep and diurnal activity patterns of human SCZ and CTRL glial chimeras were then assessed, directly comparing mice engrafted with either SCZ (line 52) or matched control (line 22) hGPCs. It was found that mice engrafted with SCZ GPCs were significantly more active than control mice engrafted with normal hGPCs. As measured by meters moved per hour, over the course of a 72-hour video-recording (Noldus Ethovision), the SCZ hGPC chimeric mice moved significantly more than their normal hGPC-engrafted controls (2-way ANOVA, F=48.35; p<0.0001) (FIG. 10F). Interestingly, while the SCZ-associated increment in activity largely occurred during night-time periods of wakefulness, the SCZ mice also manifested disrupted sleep patterns, as measured by the duration of bouts of inactivity, a surrogate for EEG-validated sleep (Pack et al., "Novel Method for High-Throughput Phenotyping of Sleep in Mice," *Physiol. Genomics* 28:232-238 (2007); McShane et al., "Characterization of the Bout Durations of Sleep and Wakefulness," *J. Neurosci. Methods* 193:321-333 (2010), which are hereby incorporated by reference in their entirety) (FIG. 10G). Within the half-hour following the phase transition from dark to light (when mice normally sleep), the CTRL mice had more continuous, uninterrupted patterns of sleep, with an average sleep bout of 511.5±36.4 seconds (8.53 minutes), whereas SCZ mice were asleep for 306.2±43.7 seconds, or 5.1 minutes per bout (p<0.01 by 2-way ANOVA, with Boneferroni post hoc t tests). The shorter average periods of inactivity manifested by SCZ hGPC mice during the normal daytime transition to sleep suggests that SCZ hGPC chimerization disrupted normal daytime sleep patterns, while increasing night-time activity. Together, these results suggest that SCZ glial chimerization was sufficient to yield heightened anxiety and fear in engrafted recipients, as well as disease-associated deficits in socialization, cognition, and sleep patterning, all features associated with human schizophrenia.

Discussion of Examples 1-7

These data suggest a significant contribution of cell-autonomous glial pathology to the genesis and development of juvenile-onset schizophrenia. In these human glial chimeric mice, schizophrenia-derived iPSC hGPCs exhibited aberrant migration with deficient engraftment in the central white matter, relative to age and gender-matched control iPSC hGPCs. Although a fraction of those SCZ hGPCs that did remain within the white matter differentiated as normal myelinogenic oligodendroglia, the premature cortical influx and hence lower density of donor-derived cells in the white matter of SCZ hGPC-engrafted mice resulted in the latter's overt hypomyelination, relative to mice engrafted with control GPCs. Thus, SCZ hGPCs appeared to traverse rather than home in to the nascent white matter, resulting in sparse hGPC colonization and hence deficient forebrain myelination. The aberrant dispersal pattern of SCZ hGPCs suggests that SCZ GPCs may not recognize developmental stop signals that permit progenitors to dwell and expand within the presumptive white matter before colonizing the cortical mantle, and may instead be biased towards rapid entry into the cortical gray matter. These observations in human SCZ glial chimeric mice are especially intriguing given the well-described hypomyelination of schizophrenic patients (Voineskos et al., "Oligodendrocyte Genes, White Matter Tract Integrity, and Cognition in Schizophrenia," *Cereb Cortex* 23:2044-2057 (2013); Najjar et al., "Neuroinflammation and White Matter Pathology in Schizophrenia: Systematic Review," *Schizophrenia Research* 161:102-112 (2015); Davis et al., "White Matter Changes in Schizophrenia: Evidence for Myelin-Related Dysfunction," *Archives of General Psychiatry* 60:443-456 (2003); Sigmundsson et al., "Structural Abnormalities in Frontal, Temporal, and Limbic Regions and Interconnecting White Matter Tracts in Schizophrenic Patients with Prominent Negative Symptoms," *Am J Psychiatry* 158:234-243 (2001), which are hereby incorporated by reference in their entirety), particularly so in early onset disease (Gogtay et al., "Three-Dimensional Brain Growth Abnormalities in Childhood-Onset Schizophrenia Visualized by Using Tensor-Based Morphometry," *Proceedings of the National Academy of Sciences of the United States of America* 105:15979-15984 (2008); Samartzis et al., "White Matter Alterations in Early Stages of Schizophrenia: A Systematic Review of Diffusion Tensor Imaging Studies," *J Neuroimaging* 24:101-110 (2014); Gogtay et al., "Childhood-Onset Schizophrenia: Insights From Neuroimaging Studies," *Journal of the American Academy of Child and Adolescent Psychiatry* 47:1120-1124 (2008), which are hereby incorporated by reference in their entirety).

These anatomic observations were especially intriguing in light of the differential gene expression pattern of the SCZ hGPCs, which revealed that the cells were deficient not only in early glial differentiation—associated transcripts, but also in genes that encode for synaptic proteins typically associated with transducing activity-dependent signals (Sudhof, T. C., "Neuroligins and Neurexins Link Synaptic Function to Cognitive Disease," *Nature* 455:903-911 (2008), which is hereby incorporated by reference in its entirety). Together, these anatomic and transcriptional data suggest that SCZ hiP SC-derived GPCs might be subject to impaired phenotypic differentiation, that might result in their neglect of the local neuronal signals that typically regulate the expansion and maturation of GPCs (Barres et al., "Proliferation of Oligodendrocyte Precursor Cells Depends on Electrical Activity in Axons," *Nature* 361:258-260 (1993), which is hereby incorporated by reference in its entirety); this might account for their rapid transit through the white matter into the overlying cortex, and hence the diminished callosal GPC density and hypomyelination of SCZ chimeric shiverer mice (FIG. 3). Thus, the myelination defect in SCZ hGPC chimeras appeared due to both deficient oligodendrocytic differentiation and the relative dearth of SCZ hGPCs remaining within the white matter. Moreover, astrocytic differentiation from SCZ hGPCs was also impaired, and may have contributed further to hypomyelination in the SCZ glial chimeras, given the metabolic dependence of mature oligodendrocytes upon local astrocytes (Amaral et al., "Metabolic Aspects of Neuron-Oligodendrocyte-Astrocyte Interactions," *Front Endocrinol (Lausanne)* 4:54 (2013); John, G. R., "Investigation of Astrocyte—Oligodendrocyte Interactions in Human Cultures," *Methods Mol Biol* 814:401-414 (2012), which is hereby incorporated by reference in its entirety).

Importantly, the defective astrocytic maturation of SCZ hGPCs might also have profound effects on developmental synaptogenesis and circuit formation, as well as on myelinogenesis. Neural connectivity and synaptic development are both intimately dependent upon astrocytic guidance (Clarke et al., "Glia Keep Synapse Distribution Under Wraps," *Cell* 154:267-268 (2013); Ullian et al., "Control of Synapse Number by Glia," *Science* 291:657-661 (2001), which is hereby incorporated by reference in its entirety), and hence upon the appropriate timing of astrocytic appearance and maturation. As a result, any disruption in astrocytic maturation by SCZ hGPCs, as observed in each of the SCZ lines studied, might be expected to significantly confound the construction and functional architecture of those neural networks in which SCZ hGPCs are resident. Moreover, glial progenitors themselves may have significant interactions with local neurons (Sakry et al., "Oligodendrocyte Precursor Cells Modulate the Neuronal Network by Activity-Dependent Ectodomain Cleavage of Glial NG2," *PLoS Biol* 12:e1001993 (2014), which is hereby incorporated by reference in its entirety), such that their dysfunction might disrupt local neuronal response thresholds and circuit formation.

Figure 8:
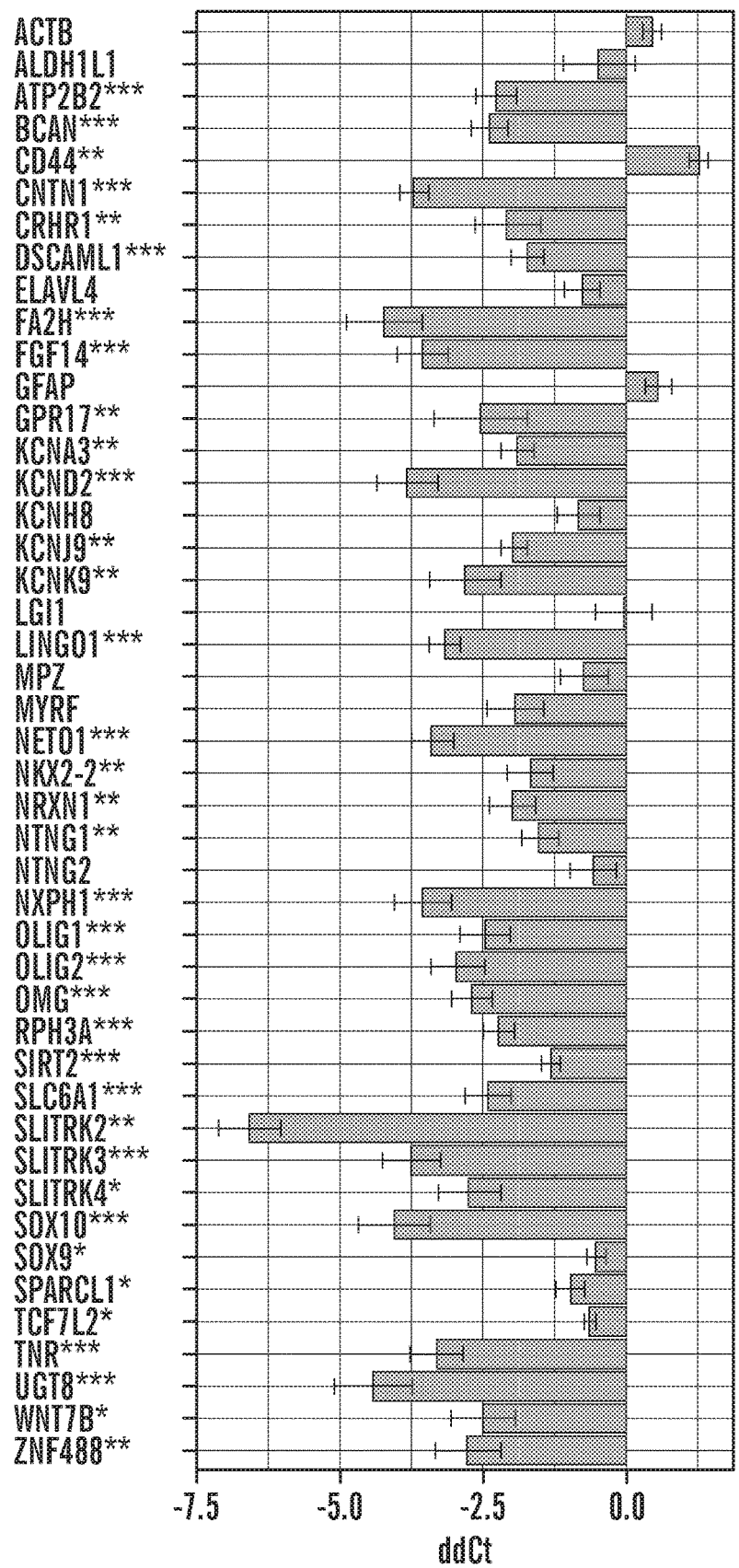
FIG. 8 shows expression of selected genes dysregulated in SCZ-derived GPCs as identified by RNA-seq analysis assessed by TaqMan Low Density Array (TLDA) RT-qPCR and compared against control GPCs. Expression data were normalized to GAPDH endogenous control. Mean ddCt values and standard error ranges calculated from 4 pooled SCZ GPC lines (n=19) against 3 pooled control GPC lines (n=10) are shown. The difference of expression in SCZ and control GPCs was assessed by paired t-test followed by multiple testing correction by Benjamini-Hochberg (BH) procedure (*=$p<0.01$, =$p<0.05$, *=$p<0.1$). 48 genes were assessed. 45 genes are shown, excluding the endogenous control and genes that had high proportion of undetermined and unreliable reactions, LRFN1 and NEUROD6. The vast majority of genes were confirmed as dysregulated in SCZ-derived GPCs. Analysis of TLDA data was performed in ExpressionSuite Software version 1.1 supplied by Applied Biosciences.

Besides the anatomic observation of deficient astrocytic maturation in SCZ hGPC chimeras, the genomic analysis of SCZ-derived hGPCs revealed the significant down-regulation in hGPCs derived from all 4 SCZ patients of a number of synaptic genes, including neuroligin-3, neuroexophilin-1, and LINGO1 relative to their normal controls (Tables 3 and Table 4; FIG. 8). Other synapse-associated genes, such as neurexin-1 and DSCAML1 were significantly and sharply down-regulated in GPCs derived from 3 patients (lines 8, 29, and 51) but not in the fourth (line 164). Similarly, SLITRKs 2-5 were significantly and sharply down-regulated in GPCs derived from 3 patients (lines 8, 51, and 164), but not in a fourth (line 29), which was instead associated with sharp down-regulation of LINGO1, DSCAML1, and several neurexins and neuroexophilins; these data suggesting the heterogeneity of transcriptional dysfunction that may lead to a final common pathway of glial-involved synaptic dysfunction in SCZ (Tables 2 and 3). These transcripts are critical contributors to synaptic stabilization and function (Sudhof, T. C., "Neuroligins and Neurexins Link Synaptic Function to Cognitive Disease," *Nature* 455:903-911 (2008), which is hereby incorporated by reference in its entirety), but while typically considered neuronal, may be produced significantly by glial cells as well (Zhang et al., "An RNA-Sequencing Transcriptome and Splicing Database of Glia, Neurons, and Vascular Cells of the Cerebral Cortex," *J. Neurosci.* 34:11929-11947 (2014), which is hereby incorporated by reference in its entirety). The relative down-regulation of these genes by SCZ hGPCs may reflect the suppression of mature glial transcripts in these cells, coincident with their relative block in glial differentiation. This in turn may lead to a relative failure of SCZ hGPCs and their derived astrocytes to provide these key proteins to their neuronal partners, as well as a potential failure on the part of glial progenitors receiving synaptic inputs to respond to afferent stimulation (De Biase et al., "Excitability and Synaptic Communication Within the Oligodendrocyte Lineage," *J Neurosci* 30:3600-3611 (2010); Lin et al., "Synaptic Signaling Between GABAergic Interneurons and Oligodendrocyte Precursor Cells in the Hippocampus," *Nat. Neurosci.* 7:24-32 (2004), which are hereby incorporated by reference in their entirety). Thus, besides the structural havoc that might be expected of a cortical connectome formed without normal astrocytic support, the synaptic structure of the resultant networks might be expected to be destabilized by poor SCZ glial provision to the synaptic cleft of key astrocytic proteins required for normal synaptic maintenance and function.

Schizophrenia is genetically heterogeneous, so that anatomic and behavioral pathology may vary significantly among animals chimerized with GPCs derived from different patients. It is thus critical that the results obtained from chimeras established with control hiPSC GPCs be stable across both distinct lines of donor cells, and among recipient mice. The chimeric brains established from the hGPCs of 3 different SCZ patients were thus compared anatomically to those established from GPCs derived from 3 control patients. None of the controls manifested the white matter-avoidant dispersal pattern of the SCZ hGPC chimeras. Similarly, this pattern of SCZ hGPC avoidance of the white matter had never been noted in any of several hundred human glial chimeras engrafted in other studies with either fetal tissue-derived (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008); Windrem et al., "A Competitive Advantage by Neonatally Engrafted Human Glial Progenitors Yields Mice Whose Brains are Chimeric for Human Glia," *J Neurosci.* 34:16153-16161 (2014), which are hereby incorporated by reference in their entirety) or normal iPSC-derived (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety) hGPCs.

Besides their clear anatomic phenotype, the SCZ hGPC-chimeric mice manifested robust behavioral phenotypes. They exhibited significantly attenuated prepulse inhibition relative to control-engrafted mice, relative anhedonia, excessive anxiety, deficient socialization with avoidance of conspecifics, and disrupted patterns of diurnal activity and sleep. These data establish that SCZ glial engraftment may yield an abnormal behavioral phenotype in recipient mice, along behavioral axes that typify selected aspects of schizophrenic behavioral pathology in humans. In that regard, while an extensive literature has implicated GPCs (De Biase et al., "Excitability and Synaptic Communication Within the Oligodendrocyte Lineage," *J Neurosci* 30:3600-3611 (2010); Bergles et al., "Neuron-Glia Synapses in the Brain," *Brain Res Rev* 63:130-137 (2010), which are hereby incorporated by reference in their entirety) as well as astroglia (Kang et al., "Astrocyte-Mediated Potentiation of Inhibitory Synaptic Transmission," *Nature Neuroscience* 1:683-692 (1998); Araque et al., "Glutamate-Dependent Astrocyte Modulation of Synaptic Transmission Between Cultured Hippocampal Neurons," *European J. Neurosci.* 10 (1998), which are hereby incorporated by reference in their entirety) in the modulation of synaptic plasticity and learning (Han et al., "Forebrain Engraftment by Human Glial Progenitor Cells Enhances Synaptic Plasticity and Learning in Adult Mice," *Cell Stem Cell* 12:342-353 (2013), which is hereby incorporated by reference in its entirety), these data do not implicate one phenotype over the other in the modulation of behavior by SCZ glial chimerization; the chimeric mice are colonized by both donor-derived human GPCs and their derived astrocytes. That said, the observations of significant defects in SCZ glial maturation shared by hGPCs derived from multiple independent patients, associated in each with hypomyelination and disrupted astrocytic differentiation, as well as with abnormal behavioral phenotypes in the resultant SCZ GPC chimeras, together suggest a strong causal contribution of glial pathology to schizophrenia. In addition, these data highlight the potential of disease-specific humanized chimeras in defining the respective contributions of glial and neuronal dysfunction in the genesis and course of neurological disease.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a neuropsychiatric disorder, said method comprising:
   selecting a subject having the neuropsychiatric disorder; and
   administering to the selected subject a preparation of glial progenitor cells at a dosage effective to treat the neuropsychiatric disorder in the subject.

2. The method of claim 1, wherein the preparation of glial progenitor cells are human glial progenitor cells.

3. The method of claim 1, wherein glial progenitor cells of the preparation are $A2B5^+$, $CD140a^+$, and/or $CD44^+$.

4. The method of claim 1, wherein said administering is carried out by intracerebral, intraventricular, intrathecal or intracisternal administration.

5. The method according to claim 1, wherein the neuropsychiatric disorder is selected from the group consisting of schizophrenia, autism spectrum disorder, and bipolar disorder.

6. The method according to claim 5, wherein the neuropsychiatric disorder is schizophrenia.

7. The method of claim 1, wherein the subject is human.

8. The method of claim 1, wherein the glial progenitor cells are derived from fetal tissue, embryonic stem cells, or induced pluripotent stem cells.

* * * * *